US012704514B2

(12) United States Patent
Sikes Johnson et al.

(10) Patent No.: US 12,704,514 B2
(45) Date of Patent: Aug. 11, 2026

(54) ENGINEERED BINDING PROTEINS FOR RECOGNITION OF BACTERIA

(71) Applicant: Massachusetts Institute of Technology, Cambridge, MA (US)

(72) Inventors: Hadley Sikes Johnson, Arlington, MA (US); Ki-Joo Sung, Minneapolis, MN (US); Yining Hao, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 340 days.

(21) Appl. No.: 18/028,195

(22) PCT Filed: Sep. 23, 2021

(86) PCT No.: PCT/US2021/051658
§ 371 (c)(1),
(2) Date: Mar. 23, 2023

(87) PCT Pub. No.: WO2022/066842
PCT Pub. Date: Mar. 31, 2022

(65) Prior Publication Data

US 2023/0358742 A1 Nov. 9, 2023

Related U.S. Application Data

(60) Provisional application No. 63/082,686, filed on Sep. 24, 2020.

(51) Int. Cl.

| | |
|---|---|
| ***G01N 33/569*** | (2006.01) |
| ***C07K 16/1232*** | (2026.01) |
| ***C07K 16/1235*** | (2026.01) |
| ***C07K 16/126*** | (2026.01) |
| ***C07K 16/1267*** | (2026.01) |

(52) U.S. Cl.
CPC ... *G01N 33/56916* (2013.01); *C07K 16/1232* (2013.01); *C07K 16/1235* (2013.01); *C07K 16/126* (2013.01); *C07K 16/1296* (2013.01); *C07K 2317/31* (2013.01); *C07K 2318/20* (2013.01); *C07K 2319/40* (2013.01); *C07K 2319/60* (2013.01); *C07K 2319/61* (2013.01); *G01N 2469/10* (2013.01)

(58) Field of Classification Search
CPC .......... G01N 33/56916; C07K 16/1235; C07K 16/1232; C07K 16/1296; C07K 14/195; C07K 2318/20
See application file for complete search history.

(56) References Cited

U.S. PATENT DOCUMENTS

2019/0113512 A1* 4/2019 Sikes Johnson ..... G01N 33/566
2020/0057058 A1 2/2020 Olsen et al.

FOREIGN PATENT DOCUMENTS

WO WO 2019/075306 A1 4/2019

OTHER PUBLICATIONS

Bowie et al. (Science, 1990, 257:1306-1310) (Year: 1990).*
Burgess et al. (J. Cell Biol. 111:2129-2138, 1990) (Year: 1990).*
Lazar et al. (Mol. Cell. Biol., 8:1247-1252, 1988) (Year: 1988).*
Bork (Genome Research, 2000, 10:398-400) (Year: 2000).*
International Search Report and Written Opinion mailed Feb. 4, 2022, for Application No. PCT/US2021/051658.
International Preliminary Report on Patentability mailed Apr. 6, 2023, for Application No. PCT/US2021/051658.
[No Author Listed], Testing methodology for *Listeria* species or *L. monocytogenes* in environmental samples. Oct. 2015. 11 pages, USDA.
Binz et al., Engineering novel binding proteins from nonimmunoglobulin domains. Nat Biotechnol. Oct. 2005;23(10):1257-68.
Boder et al., Yeast surface display for screening combinatorial polypeptide libraries. Nat Biotechnol. Jun. 1997;15(6):553-7.
Burgess et al., Beta-barrel proteins that reside in the *Escherichia coli* outer membrane in vivo demonstrate varied folding behavior in vitro. J Biol Chem. Sep. 26, 2008;283(39):26748-58. doi: 10.1074/jbc.M802754200. Epub Jul. 19, 2008.
Byrd-Bredbenner et al., Food safety in home kitchens: a synthesis of the literature. Int J Environ Res Public Health. Sep. 2, 2013;10(9):4060-85.
Chao et al., Isolating and engineering human antibodies using yeast surface display. Nat Protoc. 2006;1(2):755-68.
Freudl et al., Cloning and molecular characterization of the ompA gene from *Salmonella typhimurium*. Eur J Biochem. Aug. 15, 1983;134(3):497-502.
Gasanov et al., Methods for the isolation and identification of *Listeria* spp. and Listeria monocytogenes: a review. FEMS Microbiol Rev. Nov. 2005;29(5):851-75. doi: 10.1016/j.femsre.2004.12.002. Epub Dec. 22, 2004.
Isibasi et al., Protection against *Salmonella typhi* infection in mice after immunization with outer membrane proteins isolated from *Salmonella typhi* 9,12,d, Vi. Infect Immun. Nov. 1988;56(11):2953-9.
Ko Ferrigno et al., Non-antibody protein-based biosensors. Essays Biochem. Jun. 30, 2016;60(1):19-25.
Liu et al., Outer membrane vesicles derived from *Salmonella typhimurium* mutants with truncated LPS induce cross-protective immune responses against infection of *Salmonella enterica* serovars in the mouse model. Int J Med Microbiol. Dec. 2016;306(8):697-706. doi: 10.1016/j.ijmm.2016.08.004. Epub Aug. 25, 2016.
Miller et al., Activity-based assessment of an engineered hyperthermophilic protein as a capture agent in paper-based diagnostic tests. Mol Syst Des Eng. Dec. 1, 2016;1(4):377-381. doi: 10.1039/C6ME00032K. Epub Jun. 29, 2016.
Miller et al., Paper-based diagnostics in the antigen-depletion regime: High-density immobilization of rcSso7d-cellulose-binding domain fusion proteins for efficient target capture. Biosens Bioelectron. Apr. 15, 2018;102:456-463. doi: 10.1016/j.bios.2017.11.050. Epub Nov. 20, 2017.

(Continued)

*Primary Examiner* — Brian Gangle
*Assistant Examiner* — Lakia J Jackson-Tongue
(74) *Attorney, Agent, or Firm* — Wolf, Greenfield & Sacks, P.C.

(57) ABSTRACT

Described herein are antigen-binding molecules that bind to bacteria (e.g., *Listeria monocytogenes*) and methods of use thereof. Also described herein are compositions and kits comprising these antigen-binding molecules.

18 Claims, 23 Drawing Sheets

Specification includes a Sequence Listing.

(56) References Cited

OTHER PUBLICATIONS

Morales et al., Guide to Selecting a Biorecognition Element for Biosensors. Bioconjug Chem. Oct. 17, 2018;29(10):3231-3239. doi: 10.1021/acs.bioconjchem.8b00592. Epub Sep. 28, 2018.
Ortiz-Suarez et al., Full-Length OmpA: Structure, Function, and Membrane Interactions Predicted by Molecular Dynamics Simulations. Biophys J. Oct. 18, 2016;111(8):1692-1702.
Scallan et al., Foodborne illness acquired in the United States—major pathogens. Emerg Infect Dis. Jan. 2011;17(1):7-15.
Shamloo et al., Importance of Listeria monocytogenes in food safety: a review of its prevalence, detection, and antibiotic resistance. Iran J Vet Res. 2019 Fall;20(4):241-254.
Singh et al., The C-terminal domain of *Salmonella enterica* serovar typhimurium OmpA is an immunodominant antigen in mice but appears to be only partially exposed on the bacterial cell surface. Infect Immun. Jul. 2003;71(7):3937-46.
Sung et al., Engineering hyperthermostable RcSso7d as reporter molecule for in vitro diagnostic tests. Mol Syst Des Eng 2018; 3(6):877-82.
Sung et al., Functional comparison of paper-based immunoassays based on antibodies and engineered binding proteins. Analyst. Apr. 7, 2020;145(7):2515-2519. doi: 10.1039/d0an00299b. Epub Mar. 12, 2020.
Thaler et al., Highly sensitive immunodiagnostics at the point of care employing alternative recognition elements and smartphones: hype, trend, or revolution? Anal Bioanal Chem. Nov. 2019;411(29):7623-7635. doi: 10.1007/s00216-019-01974-0. Epub Jun. 24, 2019.
Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508.
Traxlmayr et al., Directed evolution of stabilized IgG1-Fc scaffolds by application of strong heat shock to libraries displayed on yeast. Biochim Biophys Acta. Apr. 2012;1824(4):542-9. doi: 10.1016/j.bbapap.2012.01.006. Epub Jan. 20, 2012.
Vázquez-Boland et al., Listeria pathogenesis and molecular virulence determinants. Clin Microbiol Rev. Jul. 2001;14(3):584-640.
Zhang et al., Identification of Surface Protein Biomarkers of Listeria monocytogenes via Bioinformatics and Antibody-Based Protein Detection Tools. Appl Environ Microbiol. Aug. 15, 2016;82(17):5465-76.
Zhang et al., Emulsion Agglutination Assay for the Detection of Protein-Protein Interactions: An Optical Sensor for Zika Virus. ACS Sens. Jan. 25, 2019;4(1):180-184. doi: 10.1021/acssensors.8b01202. Epub Jan. 9, 2019.
Banta et al., Replacing antibodies: engineering new binding proteins. Annu Rev Biomed Eng. 2013;15:93-113. doi: 10.1146/annurev-bioeng-071812-152412. Epub Apr. 29, 2013.
Catanzano et al., Differential scanning calorimetry study of the thermodynamic stability of some mutants of Sso7d from Sulfolobus solfataricus. Biochemistry. Jul. 21, 1998;37(29):10493-8.
Hameed et al., Conventional and emerging detection techniques for pathogenic bacteria in food science: a review. Trends Food Sci Tech. Nov. 2018; 81: 61-73.
Miller et al., Beyond Epitope Binning: Directed in Vitro Selection of Complementary Pairs of Binding Proteins. ACS Comb Sci. Jan. 13, 2020;22(1):49-60. doi: 10.1021/acscombsci.9b00176. Epub Dec. 24, 2019.
Oravcová et al., Limitation in the detection of Listeria monocytogenes in food in the presence of competing Listeria innocua. J Appl Microbiol. Feb. 2008;104(2):429-37. doi: 10.1111/j.1365-2672.2007.03554.x. Epub Sep. 21, 2007.
Traxlmayr et al., Directed evolution of proteins for increased stability and expression using yeast display. Arch Biochem Biophys. Oct. 15, 2012;526(2):174-80. doi: 10.1016/j.abb.2012.04.022. Epub May 3, 2012.
Välimaa et al., Rapid detection and identification methods for Listeria monocytogenes in the food chain—A review. Food Control. Sep. 2015; 55:103-14.

* cited by examiner

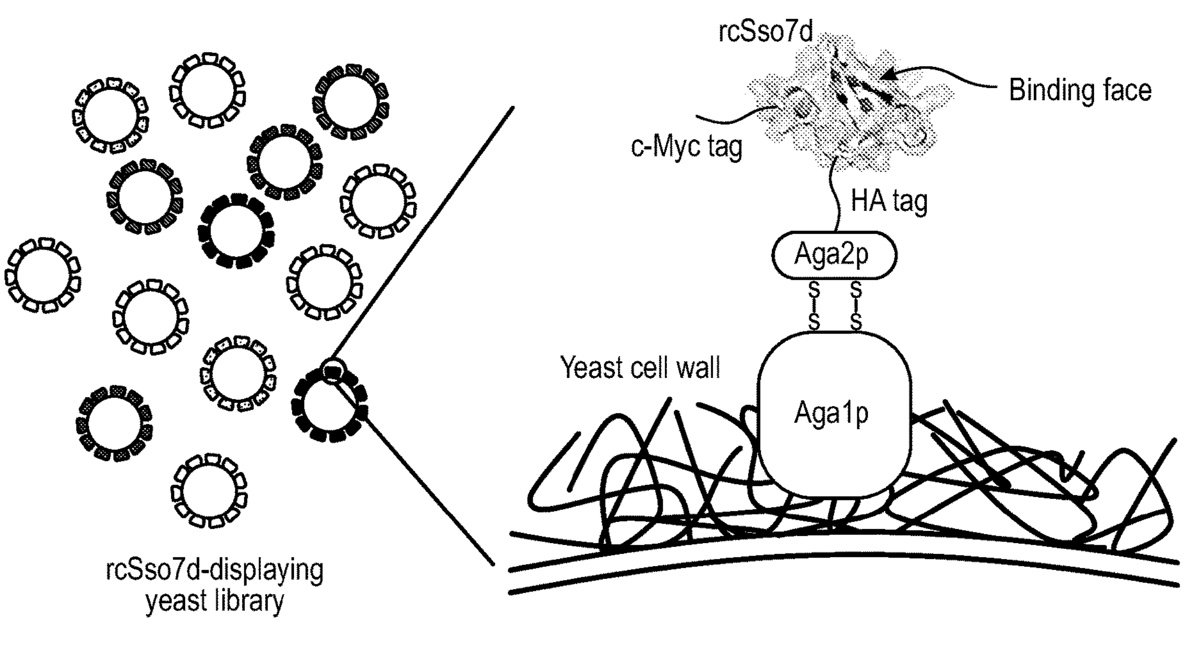
FIG. 1A FIG. 1B
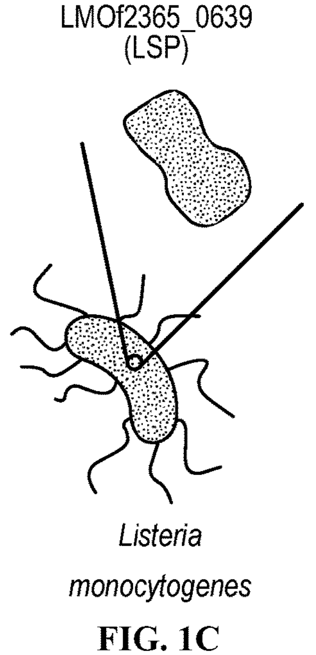
FIG. 1C

SEQ ID NO: 13 3:MATVKFTYQG EEKQVDISKI KIAKRYGQII DFSYDEGGGA RGWGIVSEKD APKELLQMLE KQ
SEQ ID NO: 14 5:MATVKFTYQG EEKQVDISKI KWVRRAGQWI DFAYDEGGGA KGYGIVSEKD APKELLQCWK S
SEQ ID NO: 15 7:MATVKFTYQG EEKQVDISKI KIAVYRYGQYIYFSYDEGGGA SGIGKVSEKD APKELLQMLE KQ

SEQ ID NO: 16 1:MATVKFTYQG EEKQVDISKI KDVGRSGQNI CFYL
SEQ ID NO: 17 2:MATVKFTYQG EEKQVDISKI KDVGRHGQKI CFLL
SEQ ID NO: 18 4:MATVKFTYQG EEKQVDISKI KDVGRYGQRI CFWL
SEQ ID NO: 19 6:MATVKFTYQG EEKQVDISKI KDVGRHGQHI CFWL

FIG. 4A

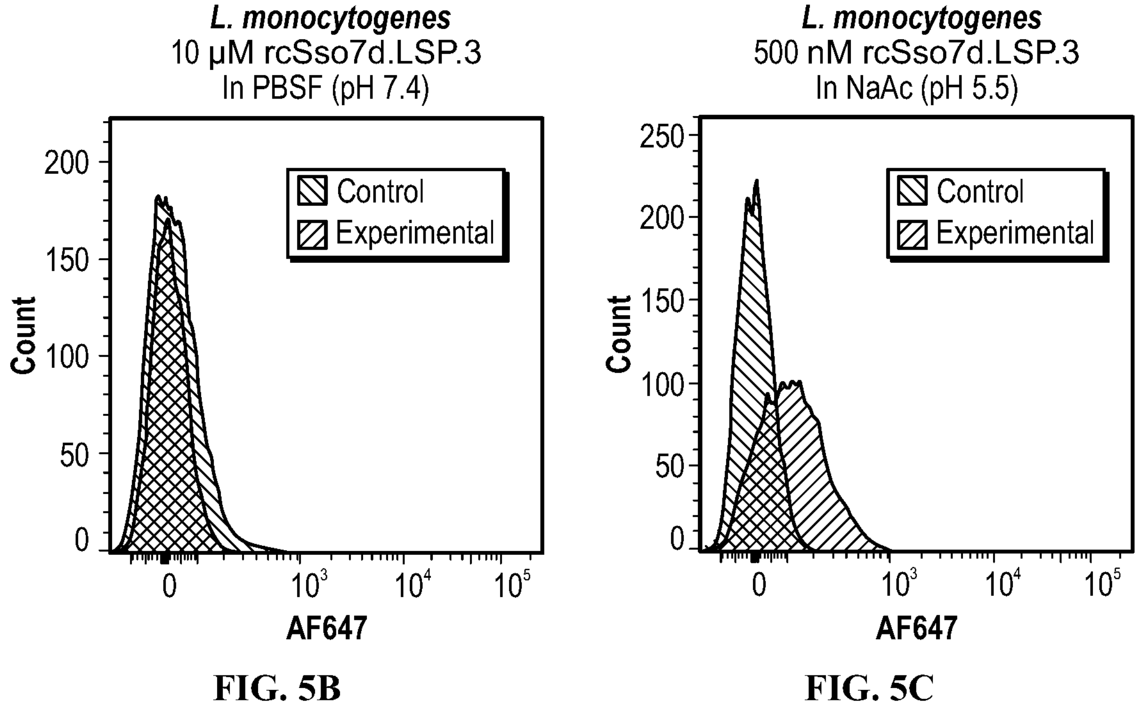
FIG. 5B
FIG. 5C
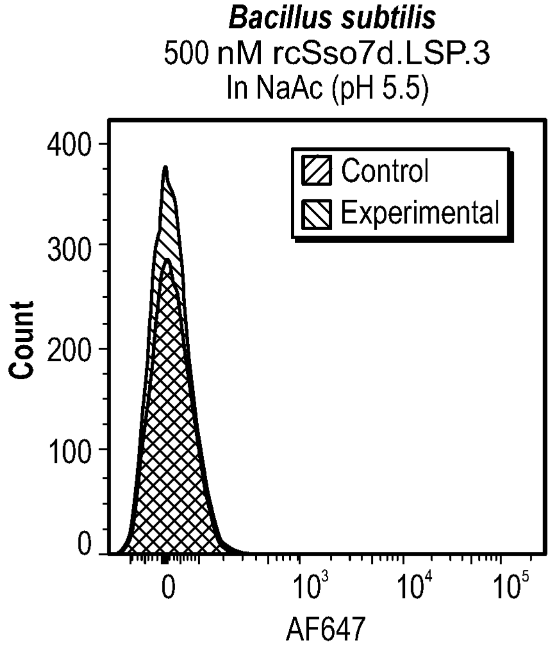
FIG. 5D

```
P02936 OMPA_SALTY  SEQ ID NO: 30    1  MKKTAIAIAVALAGFATVAQAAPKDNTWYAGAKLGWSQYHDTGFIHNDGPTHENQLGAGA   60
Q8Z7S0 OMPA_SALTI  SEQ ID NO: 31    1  MKKTAIAIAVALAGFATVAQAAPKDNTWYAGAKLGWSQYHDTGFIHNDGPTHENQLGAGA   60
P0A910 OMPA_ECOLI  SEQ ID NO: 32    1  MKKTAIAIAVALAGFATVAQAAPKDNTWYTGAKLGWSQYHDTGFINNNGPTHENQLGAGA   60
                                       *****************************:***************:*:************

P02936 OMPA_SALTY                   61  FGGYQVNPYVGFEMGYDWLGRMPYKGDNINGAYKAQGVQLTAKLGYPITDDLDVYTRLGG  120
Q8Z7S0 OMPA_SALTI                   61  FGGYQVNPYVGFEMGYDWLGRMPYKGDNTNGAYKAQGVQLTAKLGYPITDDLDVYTRLGG  120
P0A910 OMPA_ECOLI                   61  FGGYQVNPYVGFEMGYDWLGRMPYKGSVENGAYKAQGVQLTAKLGYPITDDLDIYTRLGG  120
                                       **************************:  ************************:******

P02936 OMPA_SALTY                  121  MVWRADTKSNVPGGPSTKDHDTGVSPVFAGGIEYAITPEIATRLEYQWTNNIGDANTIGT  180
Q8Z7S0 OMPA_SALTI                  121  MVWRADTKSNVPGGASTKDHDTGVSPVFAGGIEYAITPEIATRLEYQWTNNIGDANTIGT  180
P0A910 OMPA_ECOLI                  121  MVWRADTKSNVYG----KNHDTGVSPVFAGGVEYAITPEIATRLEYQWTNNIGDAHTIGT  176
                                       *********** *    *:************:***********************:****

P02936 OMPA_SALTY                  181  RPDNGLLSVGVSYRFGQQEAAPVVAPAPAPAPEVQTKHFTLKSDVLFNFNKSTLKPEGQQ  240
Q8Z7S0 OMPA_SALTI                  181  RPDNGLLSVGVSYRFGQQEAAPVVAPAPAPAPEVQTKHFTLKSDVLFNFNKSTLKPEGQQ  240
P0A910 OMPA_ECOLI                  177  RPDNGMLSLGVSYRFGQGEAAPVVAPAPAPAPEVQTKHFTLKSDVLFNFNKATLKPEGQA  236
                                       *****:**:******** *********************************:*******

P02936 OMPA_SALTY                  241  ALDQLYSQLSNLDPKDGSVVVLGFTDRIGSDAYNQGLSEKRAQSVVDYLISKGIPSDKIS  300
Q8Z7S0 OMPA_SALTI                  241  ALDQLYSQLSNLDPKDGSVVVLGFTDRIGSDAYNQGLSEKRAQSVVDYLISKGIPSDKIS  300
P0A910 OMPA_ECOLI                  237  ALDQLYSQLSNLDPKDGSVVVLGYTDRIGSDAYNQGLSERRAQSVVDYLISKGIPADKIS  296
                                       ***********************:***************:***************:****

P02936 OMPA_SALTY                  301  ARGMGESNPVTGNTCDNVKPRAALIDCLAPDRRVEIEVKGVKDVVTQPQA  350
Q8Z7S0 OMPA_SALTI                  301  ARGMGESNPVTGNTCDNVKPRAALIDCLAPDRRVEIEVKGVKDVVTQPQA  350
P0A910 OMPA_ECOLI                  297  ARGMGESNPVTGNTCDNVKQRAALIDCLAPDRRVEIEVKGIKDVVTQPQA  346
                                       ******************* ********************:*********
```

FIG. 13

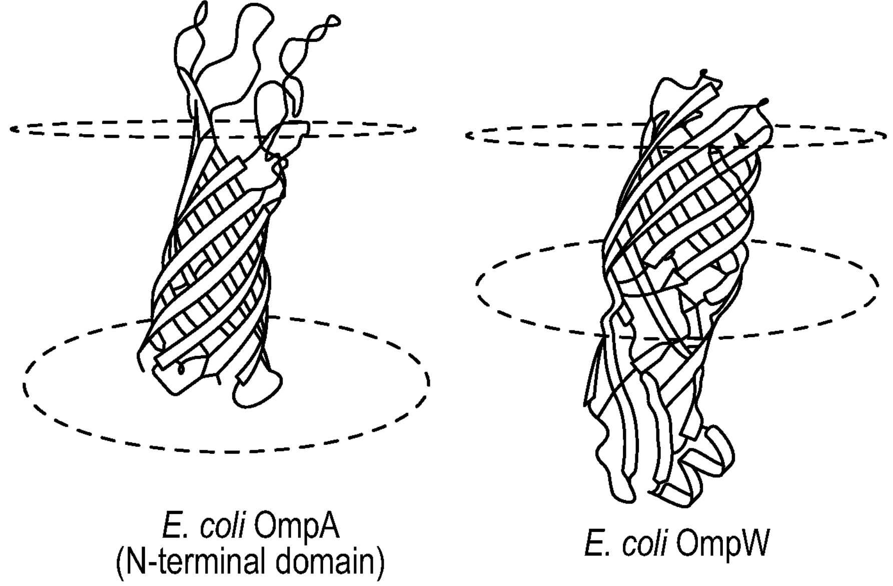
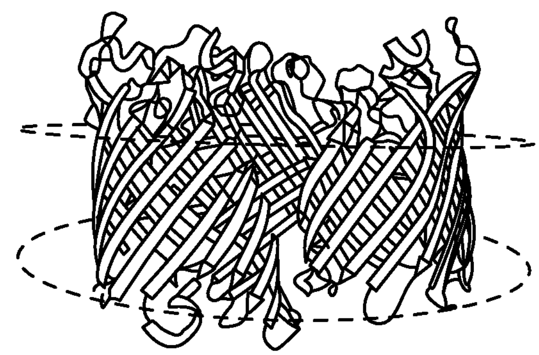
FIG. 14A

Magnetic bead sorts (MBS) to reduce library diversity from $1.4 \times 10^9$ to the upper limit for FACS ($1 \times 10^7$)

| | Nat. Omp | OmpW | OmpA |
|---|---|---|---|
| MBS round 1 | $5.5 \times 10^6$ | $3.5 \times 10^5$ | $2.5 \times 10^7$ |
| MBS round 2 | - | - | $1 \times 10^7$ |

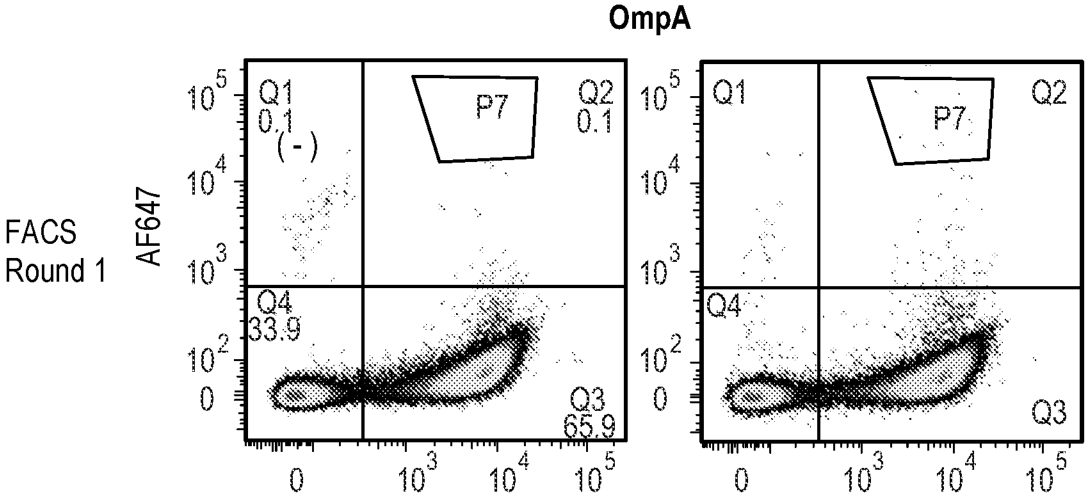
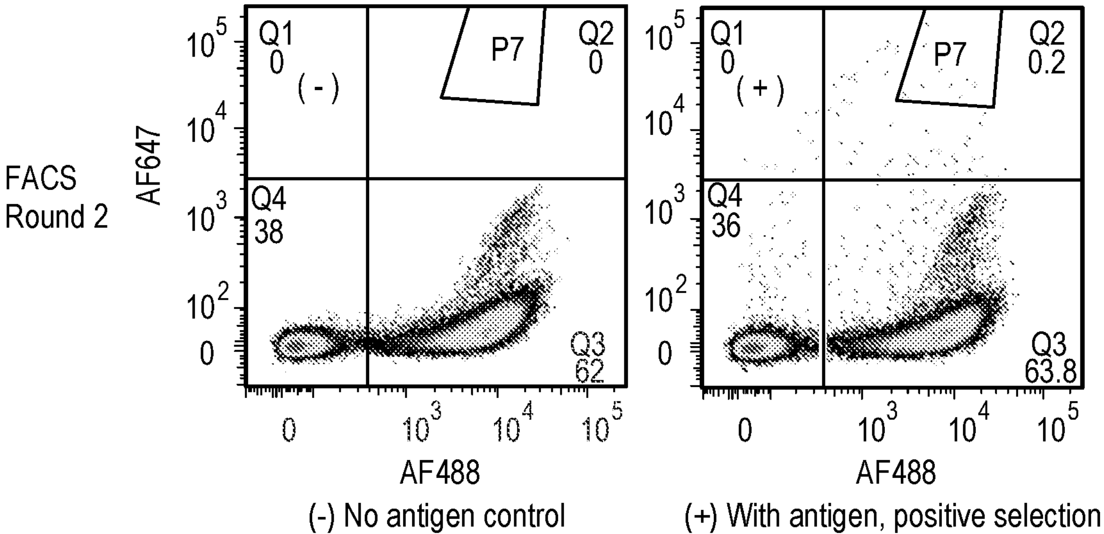
FIG. 16C

Nat.Omp.PF2.2 sequences

| | | |
|---|---|---|
| SEQ ID NO: 84 | Nat.Omp_1: | MATVKFTYQG EEKQVDISKI KWVKRDGQSI YFWYDEGGGA IGAGHVSEKD APKELLQMLE KQ |
| SEQ ID NO: 85 | Nat.Omp_2: | MATVKFTYQG EEKQVDISKI KSVSRRGQGI AFSYDEGGGA RGYGHVSEKD APKELLQMLE KQ |
| SEQ ID NO: 86 | Nat.Omp_3: | MATVKFTYQG EEKQVDISKI KIVARAGQWI WFWYDEGGGA HGRGGVSEKD APKELLQMLE KQ |
| SEQ ID NO: 87 | Nat.Omp_4: | MATVKFTYQG EEKQVDISKI KGVWRWGQWI WFWYDEGGGA AGRGYVSEKD APKELLQMLE KQ |
| SEQ ID NO: 88 | Nat.Omp_5: | MATVKFTYQG EEKQVDISKI KWVIRHGQGI YFSYDEGGGA IGGGSVSEKD APKELLQMLE KQ |
| SEQ ID NO: 89 | Nat.Omp_6: | MATVKFTYQG EEKQVDISKI KWVHRHGQWI GFDYDEGGGA IGDGSVSEKD APKELLKMLE KQ |
| SEQ ID NO: 90 | Nat.Omp_7: | MATVKFTYQG EEKQVDISKI KWVIRSGQRI NFAYDEGGGA GGYGGVSEKD APKELLQMLE KQ |
| SEQ ID NO: 91 | Nat.Omp_8: | MATVKFTYQG EEKQVDISKI KYVSRGGQDI SFRYDEGGGA IGIGYVSEKD APKELLQMLE KQ |
| SEQ ID NO: 92 | Nat.Omp_9: | MATVKFTYQG EEKQVDISKI KHVNRHGQNI DFRYDEGGGA NGRGIVSKKD APKELLQMLE KQ |
| SEQ ID NO: 93 | Nat.Omp_10: | MATVKFTYQG EEKQVDISKI KGVYRAGQHI KFRYDEGGGA GGHGGVSEKD APKELLQMLE KQ |
| SEQ ID NO: 94 | Nat.Omp_11: | MATVKFTYQG EEKQVDISKI KAVYRNGQKI IFIYDEGGGA YGHGHVSEKD APKELLQMLE KQ |
| SEQ ID NO: 95 | Nat.Omp_12: | MATVKFTYQG EEKQVDISKI KHVYRAGQYI KFGYDEGGGA AGGGHVSEKD APKELLQMLE KQ |
| SEQ ID NO: 96 | Nat.Omp_13: | MATVKFTYQG EEKQVDISKI KNVYRHGQYI KFRYDEGGGA SGYGSVSEKD APKELLQMLE KQ |
| SEQ ID NO: 97 | Nat.Omp_14: | MATVKFTYQG EEKQVDISKI KYVIRWGQHI WFYYDEGGGA WGSGNVSEKD APKELLQMLE KQ |

FIG. 17

SEQ ID NO: 98 OmpW.PF2-1: MATVKFTYQG EEKQVDISKI KWVSRWGQYI YFSYDEGGGA IGGGGVSEKD APKELLQMLE KQ
SEQ ID NO: 99 OmpW.PF2-2: MATVKFTYQG EE?QVDISKI KIVHRAGQWI GF?YDEGGGA WGSGIVSEKD APKELLQMLE KQ
SEQ ID NO: 100 OmpW.PF2-4: MATVKFTYQG EEKQVDISKI KHVSRGGQWI DFAYDEGGGA HGDGAVSEKD APKELLQMLE KQ
SEQ ID NO: 101 OmpW.PF2-6: MATVKFTYQG EEKQVDISKI KWVSRWGQYI YFSYDEGGGA SGGGSVSEKD APKELLQMLE KQ
SEQ ID NO: 102 OmpW.PF3-1: MATVKFTYQG EEKQVDISKI KWVWRWGQWI KFYYDEGGGA AGWGIVSEKD APKELLQMLE KQ
SEQ ID NO: 103 OmpW.PF3-2: MATVKFTYQG EEKQVDISKI KYVKRWGQYI WFIYDEGGGA AGYGNVSEKD APKELLQMLE KQ
SEQ ID NO: 104 OmpW.PF3-3: MATVKFTYQG EEKQVDISKI KWVWRWGQYI RFYYDEGGGA WGWGIVSEKD APKELLQMLE KQ
SEQ ID NO: 105 OmpW.PF3-7: MATVKFTYQG EEKQADISKI KIVWRWGQAI RFWYDEGGGA GGRGYVSEKD APKELLQMLE KQ

FIG. 18

SEQ ID NO: 106 OmpA.PF2-2 MATVKFTYQG EEKQVDISKI KRVWRWGQGI_YFWYDEGGGA_DGNGWVSEKD APKELLQMLEKQ
SEQ ID NO: 107 OmpA.PF2-3 MATVKFTYQG EEKQVDISKI KRVHRYGQWI_WFRYDEGGGA_RGHGHVSEKD APKELLQMLEKQ
SEQ ID NO: 108 OmpA.PF2-1 MATVKFTYQG EEKQVDISKI KHVHRWGQWI_WFWL

FIG. 19

ENGINEERED BINDING PROTEINS FOR RECOGNITION OF BACTERIA

RELATED APPLICATIONS

This application is a national stage filing under 35 U.S.C. § 371 of International Patent Application Serial Number PCT/US2021/051658, filed Sep. 23, 2021, which claims the benefit under 35 U.S.C. 119 (e) of U.S. provisional application No. 63/082,686, filed Sep. 24, 2020, the contents of each of which are incorporated by reference herein in their entireties.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Sep. 28, 2023, is named M065670499US01-SUBSEQ-CRP and is 72,726 bytes in size.

FIELD

Described herein are antigen-binding molecules that bind to bacteria (e.g., *Listeria monocytogenes, Salmonella typhi*, or *E. coli*) and methods of use thereof. Also described herein are compositions and kits comprising these antigen-binding molecules.

BACKGROUND

In the United States, there are an estimated 9.4 million cases of foodborne illnesses, resulting in approximately 56,000 hospitalizations and 1,350 deaths per year (1). *Listeria monocytogenes* is a Gram-positive foodborne pathogenic bacterium that can grow even in harsh environments (0.4 to 45° C., pH 4.0 to 9.6, and in aerobic or anaerobic conditions) (2). It is found in various food products, including fresh produce and milk. Other pathogenic bacteria such as *E. coli* and *Salmonella* also present health risks to society.

SUMMARY

*Listeria monocytogenes* causes a rare but serious disease called listeriosis. Although listeriosis is uncommon, it has a high fatality rate, encompassing an estimated 19% of deaths related to foodborne illnesses (1). Furthermore, *L. monocytogenes* results in a large economic burden—an estimated $2 billion annually—from health care costs, lost productivity, and reduced quality of life (3). Pregnant women and those with weak immune systems—including neonates, the elderly, and cancer patients—are particularly vulnerable to listeriosis (2, 4). It can result in abortion and premature birth, as well as meningoencephalitis (in 55-70% of cases) or septicemia (15-50% of cases) in the immunocompromised (4, 5). Therefore, timely detection of *L. monocytogenes* is vital to reduce the burden of this detrimental disease. Similarly *salmonellosis* is an infection caused by *Salmonella* and is a major health risk. Additionally *legionella* is another pathogenic organism that can cause sickness. Types of *E. coli* can also be pathogenic and cause sickness. Rapid diagnostic tests that can be used directly in the field site, manufacturing plants, and farms would allow for early detection of potential contaminants to reduce the current large burden of these foodborne pathogens.

Accordingly, in some aspects, the disclosure relates to antigen-binding molecules comprising a reduced charge Sso7d(rcSso7d) antigen-binding protein that binds to a bacterium. In some embodiments, an rcSso7d antigen-binding protein binds to a gram-positive bacterium. In some embodiments, an rcSso7d antigen-binding protein binds to a gram-negative bacterium. In some embodiments, an rcSso7d antigen-binding protein binds to a pathogenic bacterium. In some embodiments, an rcSso7d antigen-binding protein binds to a bacterium that causes food poisoning. In some embodiments, an rcSso7d antigen-binding protein binds to a bacterium that causes food spoilage. In some embodiments, an rcSso7d antigen-binding protein binds to a bacterium of the genus *Listeria, Escherichia, Salmonella*, and/or *Legionella*. In some embodiments, the rcSso7d antigen-binding protein binds to a *Listeria monocytogenes, Salmonella typhi*, and/or *E. coli*.

In some embodiments, the antigen-binding molecule binds to at least two antigens. In some embodiments, two or more of the at least two antigens are specific to different types of bacteria.

In some embodiments, the antigen-binding molecule binds to a protein antigen, a glycosylated protein antigen, and/or a carbohydrate antigen.

In some embodiments, an antigen-binding molecule comprises an rcSso7d antigen-binding protein that binds *Listeria monocytogenes* protein LMOf2365_0639, wherein the antigen-binding protein comprises a variable region having: (i) the amino acid sequence of any one of SEQ ID NOs: 1-8; or (ii) an amino acid sequence having 2 or 1 amino acid differences with any one of SEQ ID NOs: 1-8.

In some embodiments, the antigen-binding molecule comprises a variable region having: (i) the amino acid sequence of any one of SEQ ID NOs: 3, 5 or 7; or (ii) an amino acid sequence having no more than 2 or 1 amino acid differences with any one of SEQ ID NOs: 3, 5 or 7.

In some embodiments, the rcSso7d antigen-binding protein comprises: (i) the amino acid sequence of any one of SEQ ID NOs: 13-15; (ii) an amino acid sequence having no more than ten amino acid differences with any one of SEQ ID NOs: 13-15; or (iii) an amino acid sequence having at least 80% identity with any one of any one of SEQ ID NOs: 13-15. In some embodiments, the rcSso7d antigen-binding protein comprises the amino acid sequence of any one of SEQ ID NOs: 13-15.

In some embodiments, the antigen-binding protein comprises a variable region having: (i) the amino acid sequence of any one of SEQ ID NOs: 1, 2, 4, or 6; or (ii) an amino acid sequence no more than 2 or 1 amino acid differences with any one of SEQ ID NOs: 1, 2, 4, or 6.

In some embodiments, the rcSso7d antigen-binding protein comprises: (i) the amino acid sequence of any one of SEQ ID NOs: 16-19; (ii) an amino acid sequence having no more than seven amino acid differences with any one of SEQ ID NOs: 16-19; or (iii) an amino acid sequence having at least 80% identity with any one of any one of SEQ ID NOs: 16-19. In some embodiments, the rcSso7d antigen-binding protein comprises the amino acid sequence of any one of SEQ ID NOs: 16-19.

In some embodiments, the antigen-binding molecule further comprises an enzyme, a fluorescent protein, an immunoglobulin, a peptide tag, a small molecule, or a combination thereof.

In some embodiments, the antigen-binding molecule comprises an enzyme selected from the group consisting of alkaline phosphatase, horseradish peroxidase, and β-galactosidase.

In some embodiments, the antigen-binding molecule comprises a fluorescent protein selected from the group consisting of TagBFP, mTagBFP2, Azurite, EBFP2, EBFP2, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, Monomeric Azami Green, TagGFP2, mUKG, mWasabi, Clover, mNeonGreen, EYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, and NirFP.

In some embodiments, the antigen-binding molecule comprises a peptide tag selected from the group consisting of a His tag, a biotin acceptor tag, an HA tag, a c-Myc tag, a streptavidin tag, and a FLAG tag.

In some embodiments, the antigen-binding molecule comprises biotin.

In some embodiments, an antigen-binding molecule comprising a reduced charge Sso7d (rcSso7d) antigen-binding protein that binds *Salmonella typhi* Native Omp, said Native Omp comprising the amino acid sequence of *Salmonella typhi* membrane proteins OmpA, OmpW, OmpC, OmpF, OmpD, and phoE, wherein the antigen-binding protein comprises a variable region having: (i) the amino acid sequence of any one of SEQ ID NOs: 58-71; or (ii) an amino acid sequence having 2 or 1 amino acid differences with any one of SEQ ID NOs: 58-71.

In some embodiments, the rcSso7d antigen-binding protein comprises: (i) the amino acid sequence of any one of SEQ ID NOs: 33-46; (ii) an amino acid sequence having no more than ten amino acid differences with any one of SEQ ID NOs: 33-46; or (iii) an amino acid sequence having at least 80% identity with any one of any one of SEQ ID NOs: 33-46.

In some embodiments, the rcSso7d antigen-binding protein comprises the amino acid sequence of any one of SEQ ID NOs: 33-46.

In some embodiments, the antigen-binding molecule further comprises an enzyme, a fluorescent protein, an immunoglobulin, a peptide tag, a small molecule, or a combination thereof.

In some embodiments, the antigen-binding molecule comprises an enzyme selected from the group consisting of alkaline phosphatase, horseradish peroxidase, and β-galactosidase.

In some embodiments, the antigen-binding molecule comprises a fluorescent protein selected from the group consisting of TagBFP, mTagBFP2, Azurite, EBFP2, EBFP2, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, Monomeric Azami Green, TagGFP2, mUKG, mWasabi, Clover, mNeonGreen, EYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, and NirFP.

In some embodiments, the antigen-binding molecule comprises a peptide tag selected from the group consisting of a His tag, a biotin acceptor tag, an HA tag, a c-Myc tag, a streptavidin tag, and a FLAG tag.

In some embodiments, the antigen-binding molecule comprises biotin.

In some embodiments, an antigen-binding molecule comprising a reduced charge Sso7d (rcSso7d) antigen-binding protein that binds *E. coli* OmpW, wherein the antigen-binding protein comprises a variable region having: (i) the amino acid sequence of any one of SEQ ID NOs: 73-80; or (ii) an amino acid sequence having 2 or 1 amino acid differences with any one of SEQ ID NOs: 73-80.

In some embodiments, the rcSso7d antigen-binding protein comprises: (i) the amino acid sequence of any one of SEQ ID NOs: 47-54; (ii) an amino acid sequence having no more than ten amino acid differences with any one of SEQ ID NOs: 47-54; or (iii) an amino acid sequence having at least 80% identity with any one of any one of SEQ ID NOs: 47-54.

In some embodiments, the rcSso7d antigen-binding protein comprises the amino acid sequence of any one of SEQ ID NOs: 47-54.

In some embodiments, the antigen-binding molecule further comprises an enzyme, a fluorescent protein, an immunoglobulin, a peptide tag, a small molecule, or a combination thereof.

In some embodiments, the antigen-binding molecule comprises an enzyme selected from the group consisting of alkaline phosphatase, horseradish peroxidase, and β-galactosidase.

In some embodiments, the antigen-binding molecule comprises a fluorescent protein selected from the group consisting of TagBFP, mTagBFP2, Azurite, EBFP2, EBFP2, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, Monomeric Azami Green, TagGFP2, mUKG, mWasabi, Clover, mNeonGreen, EYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, and NirFP.

In some embodiments, the antigen-binding molecule comprises a peptide tag selected from the group consisting of a His tag, a biotin acceptor tag, an HA tag, a c-Myc tag, a streptavidin tag, and a FLAG tag.

In some embodiments, the antigen-binding molecule comprises biotin.

In some embodiments, an antigen-binding molecule comprising a reduced charge Sso7d (rcSso7d) antigen-binding protein that binds *E. coli* OmpA, wherein the antigen-binding protein comprises a variable region having: (i) the amino acid sequence of any one of SEQ ID NOs: 81-83; or (ii) an amino acid sequence having 2 or 1 amino acid differences with any one of SEQ ID NOs: 81-83.

In some embodiments, the rcSso7d antigen-binding protein comprises: (i) the amino acid sequence of any one of SEQ ID NOs: 55-57; (ii) an amino acid sequence having no more than ten amino acid differences with any one of SEQ ID NOs: 55-57; or (iii) an amino acid sequence having at least 80% identity with any one of any one of SEQ ID NOs: 55-57. In some embodiments, the rcSso7d antigen-binding protein comprises the amino acid sequence of any one of SEQ ID NOs: 55-57.

In some embodiments, the antigen-binding molecule further comprises an enzyme, a fluorescent protein, an immunoglobulin, a peptide tag, a small molecule, or a combination thereof.

In some embodiments, the antigen-binding molecule comprises an enzyme selected from the group consisting of alkaline phosphatase, horseradish peroxidase, and β-galactosidase.

In some embodiments, the antigen-binding molecule comprises a fluorescent protein selected from the group consisting of TagBFP, mTagBFP2, Azurite, EBFP2, EBFP2, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, Monomeric Azami Green, TagGFP2, mUKG, mWasabi, Clover, mNeonGreen, EYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, and NirFP.

In some embodiments, the antigen-binding molecule comprises a peptide tag selected from the group consisting of a His tag, a biotin acceptor tag, an HA tag, a c-Myc tag, a streptavidin tag, and a FLAG tag.

In some embodiments, the antigen-binding molecule comprises biotin.

In some aspects, the disclosure relates to compositions comprising an antigen-binding molecule described herein and a buffer, wherein the buffer has a pH≤6.0. In some embodiments, the buffer has a pH of 5.0-6.0. In some embodiments, the buffer has a pH of about 5.5.

In some embodiments, the buffer comprises sodium acetate and/or phosphate-buffered saline.

In some embodiments, the composition further comprises a LMOf2365_0639 protein, an OmpA protein, an OmpW protein, an OmpC protein, an OmpF protein, an OmpD protein, a phoE protein, or a combination thereof.

In some embodiments, the composition further comprises a *Listeria monocytogenes* cell, a *Salmonella typhi* cell, an *E. coli* cell, or a combination thereof.

In some aspects, the disclosure relates to methods of detecting a protein of interest in a sample.

In some embodiments, a method of detecting LMOf2365_0639 in a sample comprises: (a) contacting the sample with an antigen-binding molecule described herein that binds to LMOf2365_0639; and (b) detecting, if present, LMOf2365_0639 protein bound by the antigen-binding molecule.

In some embodiments, a method of detecting OmpA, OmpW, OmpC, OmpF, OmpD, phoE, or a combination thereof in a sample comprises: (a) contacting the sample with an antigen-binding molecule described herein that binds to OmpA, OmpW, OmpC, OmpF, OmpD, phoE, or a combination thereof; and (b) detecting, if present, OmpA, OmpW, OmpC, OmpF, OmpD, phoE, or a combination thereof bound by the antigen-binding molecule.

In some embodiments, a method of detecting OmpW in a sample comprises: (a) contacting the sample with an antigen-binding molecule described herein that binds to OmpW; and (b) detecting, if present, OmpW bound by the antigen-binding molecule.

In some embodiments, a method of detecting OmpA in a sample comprises: (a) contacting the sample with an antigen-binding molecule described herein that binds to OmpA; and (b) detecting, if present, OmpA bound by the antigen-binding molecule.

In some embodiments, the sample is from a food product. In some embodiments, the sample is from a subject. In some embodiments, the subject is a mammal. In some embodiments, the subject is a human. In some embodiments, the method further comprises treating the subject.

In some embodiments, the sample is contacted with the antigen-binding protein at a pH≤6.0. In some embodiments, the sample is contacted at a pH of 5.0-6.0. In some embodiments, the sample is contacted at a pH of about 5.5.

In some embodiments, the sample comprises sodium acetate and/or phosphate-buffered saline.

In some embodiments, step (a) further comprises contacting the sample with a detection agent, wherein the detection agent binds to or is bound by the antigen-binding molecule.

In some embodiments, the detection agent comprises an enzyme, a fluorescent protein, an immunoglobulin, a peptide tag, a small molecule, and/or a combination thereof.

In some embodiments, the detection enzyme comprises an enzyme selected from the group consisting of alkaline phosphatase, horseradish peroxidase, and β-galactosidase.

In some embodiments, the detection agent comprises a fluorescent protein selected from the group consisting of TagBFP, mTagBFP2, Azurite, EBFP2, EBFP2, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, Monomeric Azami Green, TagGFP2, mUKG, mWasabi, Clover, mNeonGreen, EYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, and NirFP.

In some embodiments, the detection agent comprises a peptide tag selected from the group consisting of a His tag, a biotin acceptor tag, an HA tag, a c-Myc tag, a streptavidin tag, and a FLAG tag.

In some embodiments, the detection agent comprises biotin.

In some aspects, the disclosure relates to methods of detecting bacteria in a sample.

In some embodiments, the method comprises: (a) contacting the sample with an antigen-binding molecule described herein that binds to LMOf2365_0639; and (b) detecting, if present, bacteria bound by the antigen-binding molecule. In some embodiments, the method is a method of detecting a *Listeria monocytogenes* cell in a sample comprising: (a) contacting the sample with an antigen-binding molecule described herein that binds to LMOf2365_0639; and (b) detecting, if present, *Listeria monocytogenes* bound by the antigen-binding molecule.

In some embodiments, the method comprises: (a) contacting the sample with an antigen-binding molecule described herein that binds to OmpA, OmpW, OmpC, OmpF, OmpD, phoE, or a combination thereof; and (b) detecting, if present, bacteria bound by the antigen-binding molecule. In some embodiments, the method is a method of detecting a *Salmonella typhi* cell in a sample comprising: (a) contacting the sample with an antigen-binding molecule described herein OmpA, OmpW, OmpC, OmpF, OmpD, phoE, or a combination thereof; and (b) detecting, if present, *Salmonella typhi* bound by the antigen-binding molecule.

In some embodiments, the method comprises: (a) contacting the sample with an antigen-binding molecule described herein that binds to OmpW; and (b) detecting, if present, bacteria bound by the antigen-binding molecule. In some embodiments, the method is a method of detecting a *E. coli* cell in a sample comprising: (a) contacting the sample with an antigen-binding molecule described herein that binds to OmpW or OmpA; and (b) detecting, if present, *E. coli* bound by the antigen-binding molecule.

In some embodiments, the sample is from a food product. In some embodiments, the sample is from a subject. In some embodiments, the subject is a mammal. In some embodiments, the subject is a human. In some embodiments, the method further comprises treating the subject.

In some embodiments, the sample is contacted with the antigen-binding protein at a pH≤6.0. In some embodiments, the sample is contacted at a pH of 5.0-6.0. In some embodiments, the sample is contacted at a pH of about 5.5.

In some embodiments, the sample comprises sodium acetate and/or phosphate-buffered saline.

In some embodiments, step (a) further comprises contacting the sample with a detection agent, wherein the detection agent binds to or is bound by the antigen-binding molecule.

In some embodiments, the detection agent comprises an enzyme, a fluorescent protein, an immunoglobulin, a peptide tag, a small molecule, and/or a combination thereof.

In some embodiments, the detection enzyme comprises an enzyme selected from the group consisting of alkaline phosphatase, horseradish peroxidase, and β-galactosidase.

In some embodiments, the detection agent comprises a fluorescent protein selected from the group consisting of TagBFP, mTagBFP2, Azurite, EBFP2, EBFP2, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, Monomeric Azami Green, TagGFP2, mUKG, mWasabi, Clover, mNeonGreen, EYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, and NirFP.

In some embodiments, the detection agent comprises a peptide tag selected from the group consisting of a His tag, a biotin acceptor tag, an HA tag, a c-Myc tag, a streptavidin tag, and a FLAG tag.

In some embodiments, the detection agent comprises biotin.

In some aspects, the disclosure relates to methods of killing a bacterial cell.

In some embodiments, the method comprises contacting a *Listeria monocytogenes* cell with an antigen-binding molecule described herein that binds to LMOf2365_0639, wherein the antigen-binding molecule further comprises a cytotoxic agent.

In some embodiments, the method comprises contacting a *Salmonella typhi* cell with an antigen-binding molecule described herein that binds to OmpA, OmpW, OmpC, OmpF, OmpD, phoE, or a combination thereof, wherein the antigen-binding molecule further comprises a cytotoxic agent.

In some embodiments, the method comprises contacting an *E. coli* cell with an antigen-binding molecule described herein that binds to OmpW or OmpA, wherein the antigen-binding molecule further comprises a cytotoxic agent.

In some embodiments, the sample is contacted with the antigen-binding protein at a pH≤6.0. In some embodiments, the sample is contacted at a pH of 5.0-6.0. In some embodiments, the sample is contacted at a pH of about 5.5.

In some embodiments, the sample comprises sodium acetate and/or phosphate-buffered saline.

In some aspects, the disclosure relates to methods of monitoring growth of a population of bacteria. In some embodiments, the method comprises: (a) contacting a sample comprising at least a subset of the population with an antigen-binding molecule described herein; and (b) repeating step (a) at least once.

In some embodiments, the method is a method of monitoring growth of *Listeria monocytogenes* comprising: (a) contacting a sample comprising at least a subset of the population with an antigen-binding molecule described herein that binds to LMOf2365_0639; and (b) repeating step (a) at least once.

In some embodiments, the method is a method of monitoring growth of *Salmonella typhi* comprising: (a) contacting a sample comprising at least a subset of the population with an antigen-binding molecule described herein that binds to OmpA, OmpW, OmpC, OmpF, OmpD, phoE, or a combination thereof; and (b) repeating step (a) at least once.

In some embodiments, the method is a method of monitoring growth of *E. coli* comprising: (a) contacting a sample comprising at least a subset of the population with an antigen-binding molecule described herein that binds to OmpW or OmpA; and (b) repeating step (a) at least once.

In some embodiments, step (a) further comprises contacting the sample with a detection agent, wherein the detection agent binds to or is bound by the antigen-binding molecule.

In some embodiments, the detection agent comprises an enzyme, a fluorescent protein, an immunoglobulin, a peptide tag, a small molecule, and/or a combination thereof.

In some embodiments, the detection enzyme comprises an enzyme selected from the group consisting of alkaline phosphatase, horseradish peroxidase, and β-galactosidase.

In some embodiments, the detection agent comprises a fluorescent protein selected from the group consisting of TagBFP, mTagBFP2, Azurite, EBFP2, EBFP2, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, Monomeric Azami Green, TagGFP2, mUKG, mWasabi, Clover, mNeonGreen, EYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, and NirFP.

In some embodiments, the detection agent comprises a peptide tag selected from the group consisting of a His tag, a biotin acceptor tag, an HA tag, a c-Myc tag, a streptavidin tag, and a FLAG tag.

In some embodiments, the detection agent comprises biotin.

In some aspects, the disclosure relates to kits comprising an antigen-binding molecule described herein.

In some embodiment, the kit further comprises a buffer. In some embodiments, the buffer has a pH of ≤6.0. In some embodiments, the buffer has a pH of 5.0-6.0. In some embodiments, the buffer has a pH of about 5.5. In some embodiments, the buffer comprises sodium acetate and/or phosphate-buffered saline.

In some embodiments, the kit further comprises a substrate. In some embodiments, the substrate comprises paper, nitrocellulose, cellulose powder, and/or a liquid colloid. In some embodiments, the antigen-binding molecule is bound to the substrate.

In some embodiments, the kit further comprises a growth media that allows for bacterial growth.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIGS. 1A-1C. FIG. 1A. Schematic of the combinatorial yeast-surface display library for rcSso7d (diversity: ~$1.4\times10^9$). FIG. 1B. Schematic of the yeast surface display complex. rcSso7d (PDB: 1SSO) is expressed with HA/c-Myc epitope tags and genetically fused to the Aga2p protein, which is linked to Aga1p in the cell wall via disulfide bonds. The variable binding face of rcSso7d is indicated. FIG. 1C. Schematic of *L. monocytogenes* and the target surface protein, LMOf2365_0639 ("LSP").

FIG. 3A. Schematic of protein complex for rcSso7d clonal analysis on yeast-surface display. FIG. 3B. FACS histograms of target-specific binding for the eight identified rcSso7d clones against 20 nM of LSP from the three different selection processes. All clones show specific binding, except clone 8, which has off-target binding to the labeling reagents.

FIGS. 4A-4C. Heat stability of identified rcSso7d clones. FIG. 4A. Aligned amino acid sequences of the seven unique rcSso7d clones specific to LSP. Clones 3, 5, and 7 are full-length, and clones 1, 2, 4, and 6 are truncated (early stop codon). Binding face sequences are underlined. Highlighted amino acids were previously found to be important for rcSso7d core stability. Clone 7 has an additional inserted amino acid (bolded). FIG. 4B. Protein ribbon structure of rcSso7d (PDB: 1SSO), depicting the amino acids of the binding face and the hydrophobic core. F5, Y7, F31, and Y33 are particularly important in rcSso7d core stability (24). FIG. 4C. FACS histograms of rcSso7d thermal stability, demonstrating reduction in target binding activity (percentage represents reduction in signal based on the geometric mean fluorescence intensity) after heating the rcSso7d-displayed clonal yeast for 10 minutes at 80° C.

FIGS. 5A-5D. rcSso7d.LSP.3 binding to live, whole cells. FIG. 5A. Schematic of desired protein complex on the surface of *L. monocytogenes* cells for rcSso7d binding. FIGS. 5A-5D. FACS histograms of rcSso7d.LSP.3 binding to live, whole cell (FIGS. 5B-5C) *L. monocytogenes* or (FIG. 5C) *Bacillus subtilis*. rcSso7d incubations with whole *L. monocytogenes* cells were tested in (FIG. 5B) PBS (pH 7.4) and (FIG. 5C) sodium acetate (pH 5.5). Higher signal was seen in the lower pH buffer. Incubations with whole *B. subtilis* cells were tested in (FIG. 5D) sodium acetate (pH 5.5) for comparison.

FIG. 13. Alignment of OmpA amino acid sequences from *Salmonella* species and *E. coli*. Regions of identity are highlighted.

FIG. 14A-14B. Design, production and characterization of additional antigens. FIG. 14A. Crystal structures of *E. coli* OmpA, *E. coli* OmpW and *Salmonella typi* Native Omp. FIG. 14B. SDS PAGE gels of the antigens used in selection of rcSso7d variants.

FIG. 15. Magnetic bead sorts (MBS) to reduce library diversity from $1.4\times10^9$ to the upper limit for FACS ($1\times10^7$).

FIGS. 16A-16C. FACS dot plots for the libraries generated from MBS and FACS selections against Native Omp (FIG. 16A), OmpW (FIG. 16B) and OmpA (FIG. 16C). The subpopulations of antigen-binders in each round were selected, expanded in culture, and eventually sequenced to determine the identity of the clones that are specific to each antigen.

FIG. 17. Aligned amino acid sequences of unique rcSso7d clones specific to Native Omp. Binding face sequences are underlined. Highlighted amino acids were previously found to be important for rcSso7d core stability.

FIG. 18. Aligned amino acid sequences of unique rcSso7d clones specific to OmpW. Binding face sequences are underlined. Highlighted amino acids were previously found to be important for rcSso7d core stability.

FIG. 19. Aligned amino acid sequences of unique rcSso7d clones specific to OmpA. Binding face sequences are underlined. Highlighted amino acids were previously found to be important for rcSso7d core stability.

DETAILED DESCRIPTION

Figure 2:
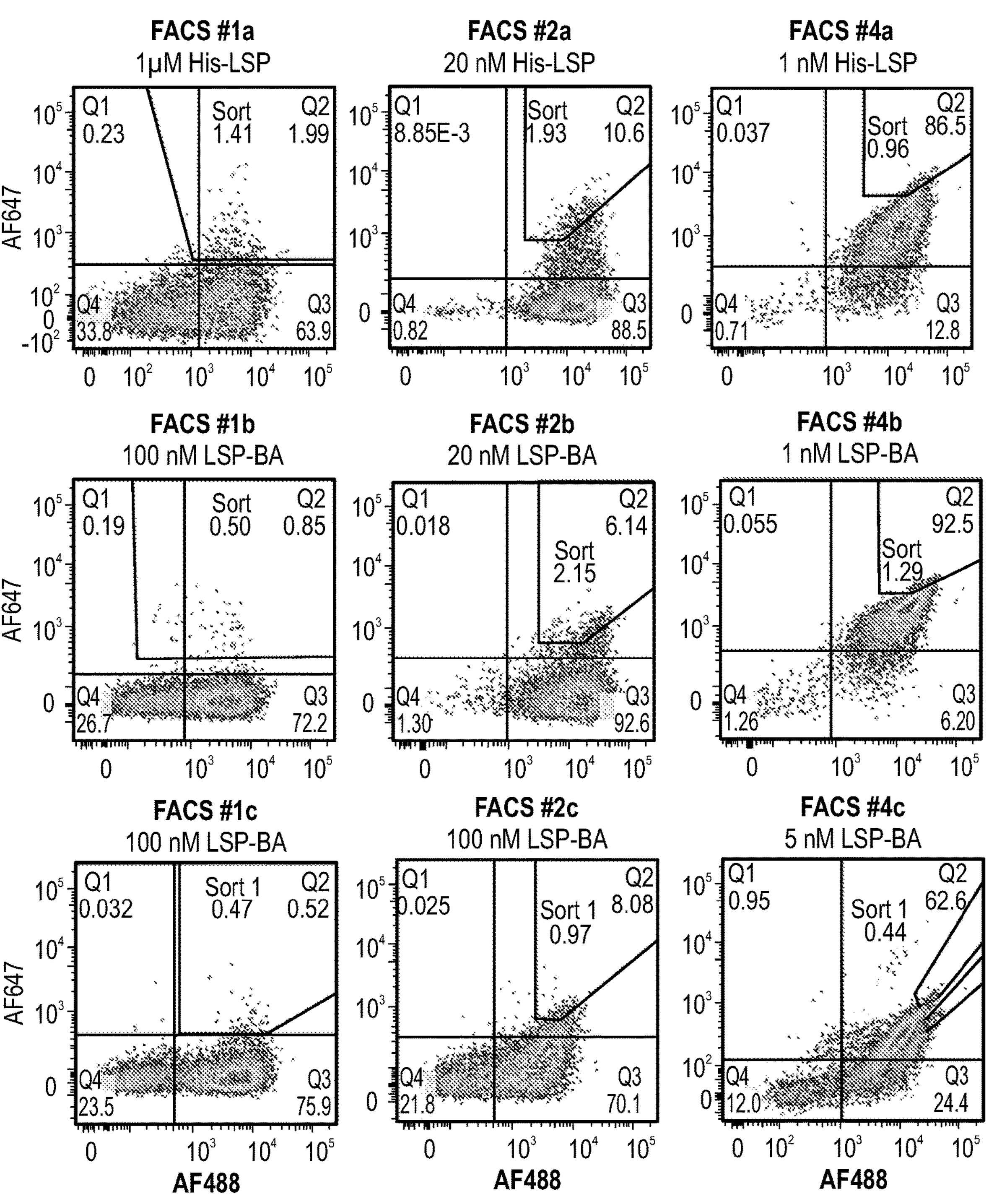
FIG. 2. Representative FACS dot plots for the FACS selections ("a": MBS and FACS against His-LSP, top; "b": MBS against His-LSP and FACS against LSP-BA, middle; "c": MBS and FACS against LSP-BA, bottom). Positive sorts are shown for FACS #1, #2, and #4 to show enrichment. Negative sorts were conducted prior to FACS #2a, #4a, #2b, and #4b. Concentration of His-LSP or LSP-BA used are listed above the plots, with a reduction in concentration in subsequent FACS rounds for increased stringency. Numbers indicate the percentage of the population in each quadrant. Gates drawn indicate the gates used for sorting.

The traditional method of detecting bacteria (e.g., *Listeria*, such as *L. monocytogenes; Salmonella* and *E. coli*) in food and environmental samples uses a culture-based method, which involves multiple sequential pre-enrichment steps by plating on selective agar before additional biochemical tests for confirmation (6). This process is quite time-consuming (>96 hours due to enrichment steps) and can be quite labor-intensive (2, 4, 7, 8). Additionally, the enrichment process may lead to false negative results if other non-pathogenic bacteria is also present in the sample and allowed to outgrow the *L. monocytogenes* (9). Non-culture-based, rapid detection methods have been investigated to reduce the processing time; these methods include nucleic acid based tests—such as polymerase chain reaction (PCR), real-time PCR, and loop-mediated isothermal amplification (LAMP), mass spectrometry, and immunoassays and biosensors (2, 4, 7, 8). Unfortunately, many of these methods still require lengthy pre-enrichment steps, require expensive equipment, are not able to distinguish live cells from dead cells, or have inadequate sensitivity and specificity.

Rapid diagnostic tests that can be used directly in the field site, manufacturing plants, and farms would allow for early detection of potential contaminants to reduce the current large burden of these foodborne pathogens. These tests would ideally not require complicated equipment or trained personnel, be inexpensive, and provide results within hours rather than days. Typical rapid diagnostic tests use antibodies to detect presence of the target molecule in the sample. Antibodies have been developed for *L. monocytogenes* detection by targeting surface biomarkers on the bacteria; however, most of these antibodies have not been specific to *L. monocytogenes* (7). In recent years, alternative binding proteins have been investigated for rapid diagnostic tests to replace antibodies as the affinity reagents due to their thermal stability, easy and inexpensive mass-production, and manipulability of the scaffold for additional properties (10-14).

Here, the reduced-charge Sso7d (rcSso7d) alternative binding scaffold was used to engineer affinity reagents against bacteria (e.g., *L. monocytogenes*) via in vitro selection processes using yeast-surface display. For example, a *L. monocytogenes* surface protein, LMOf2365_0639, that had previously been identified as a surface marker for *L. monocytogenes* (15) was targeted. rcSso7d clones were identified that bind to live *L. monocytogenes* whole cells with minimal cross-reactivity to a non-pathogenic Gram-positive bacterium, *Bacillus subtilis*. Those skilled in the art will realize that other bacterial will have unique surface proteins that can be used as targets for the selection of engineered binding proteins. The methods described here can be used to develop engineered binding proteins for all types of bacteria. Once identified these binding proteins can be used to create methods to selectively detect different bacteria. Although not limited to pathogenic bacteria, efficient detection methods enabled by these binding proteins are of particular interest to ensure the safety of food and beverages. Additionally, non-pathogenic bacteria that leads to spoilage of food and beverages is of interest, to prevent food waste by allowing early detection of these organisms in the food production process.

I. Antigen-Binding Molecules.

In some aspects, this disclosure relates to antigen-binding molecules that bind to surface proteins associated with bacteria of interest, such as LSP (LMOf2365_0639, a surface protein of *Listeria monocytogenes* (15)), OmpA, OmpW, OmpC, OmpF, OmpD, and/or phoE. In some embodiments, an antigen-binding molecule comprises a reduced charge Sso7d (rcSso7d) antigen-binding protein. In some embodiments, an antigen-binding molecule comprises multiple rcSso7d antigen-binding proteins. In some embodiment, each of the antigen binding molecules are the same. In other embodiments, an antigen-binding molecule comprises two or more distinct rcSso7d antigen-binding proteins (e.g., each of which binds to a unique antigen).

The general structure of rcSso7d antigen-binding proteins have been described previously. See e.g., FIGS. 4A-4B. Of particular note, an rcSso7d antigen-binding protein comprises a scaffold region (i.e., stable core region in FIG. 4B) and a variable region (i.e., binding face in FIG. 4B). The amino acids of the variable region are surface exposed and enable an rcSso7d antigen-binding protein to specifically bind a target (e.g., LMOf2365_0639).

It is understood that the amino acids that form the variable region need not be positioned sequentially within the amino acid sequence of the antigen-binding protein; in other words, the amino acids corresponding to the variable region may be separated by one or more amino acid of the scaffold region. Notwithstanding this point, the amino acids corresponding to the scaffold region and the variable region of an rcSso7d antigen-binding protein are readily identifiable by one having ordinary skill in the art (16-22).

In some embodiments, an antigen-binding molecule comprises an rcSso7d antigen-binding protein comprising a variable region having a defined amino acid sequence. In light of the disclosure above (i.e., relating to the structures of rcSso7d antigen-binding proteins), it is understood that the amino acid sequences provided herein for an rcSso7d antigen-binding protein variable region do not strictly reflect an N-terminal to C-terminal sequence of amino acids within the polypeptide chain of the rcSso7d antigen-binding protein. Instead, it is understood that—although the amino acid sequences are provided in the N-terminal to C-terminal orientation—one or more amino acids of the scaffold region may separate the amino acids of the variable domains described herein. See e.g., FIG. 4A.

In some embodiments, an antigen-binding molecule comprises a rcSso7d antigen-binding protein that binds to a bacterium. In some embodiments, an rcSso7d antigen-binding protein binds to a gram-positive bacterium. In some embodiments, an rcSso7d antigen-binding protein binds to a gram-negative bacterium. In some embodiments, an rcSso7d antigen-binding protein binds to a pathogenic bacterium. In some embodiments, an rcSso7d antigen-binding protein binds to a bacterium that causes food poisoning. In some embodiments, an rcSso7d antigen-binding protein binds to a bacterium that causes food spoilage.

In some embodiments, an rcSso7d antigen-binding protein binds to a bacterium of the genus *Listeria, Escherichia, Salmonella*, or *Legionella*. Bacterial species, sub-species and strains falling within each of these genera are known to those having ordinary skill in the art. For example, exemplary species falling within the genus *Listeria* include *Listeria monocytogenes, Listeria seeligeri, Listeria ivanovii, Listeria welshimeri, Listeria marthii, Listeria innocua, Listeria grayi, Listeria fleischmannii, Listeria floridensis, Listeria aquatica, Listeria newyorkensis, Listeria cornellensis, Listeria rocourtiae, Listeria weihenstephanensis, Listeria grandensis, Listeria riparia*, and *Listeria booriae*.

In some embodiments, an rcSso7d antigen-binding protein binds to an antigen that is shared by bacteria of different genera, species, sub-species, and/or strains. For example, in some embodiments an rcSso7d antigen-binding protein binds to a conserved surface antigen of such genera, species, sub-species, and/or strains.

In other embodiments, an rcSso7d antigen-binding protein binds to an antigen that is unique to a specific bacterial species, sub-species, or strain.

In some embodiments, an antigen-binding molecule binds to a protein antigen, a glycosylated protein antigen, and/or a carbohydrate antigen, which may be common to more than one genera, species, sub-species, and/or strains, or which may be unique to a specific bacterial species, sub-species, or strain.

Antigens that can be used for selective detection of one or more genera, species, sub-species, and/or strains by the antigen-binding proteins described herein can be identified using methods known to those of skill in the art, e.g., by database searching. In some embodiments, an antigen is present on the surface of a cell and can be used, for example, to detect viable/intact cells. In some embodiments, an antigen is present in the interior of a cell. In some embodiments, the antigens are surface proteins that are specific to a particular species of bacteria or alternatively are widely expressed across one of more species or genera. In some embodiments, the antigens contain carbohydrate residues that are specific to a particular species of bacteria, or alternatively that are widely expressed across one or more species or genera. Thus, the antigen-binding proteins and methods of use thereof disclosed herein can be used to target different groups or individual types of bacteria by selecting the engineered binding proteins that target an antigen of interest. In some embodiments, multiple binding proteins that bind multiple antigens can be identified or engineered, and this collection of multiple binding proteins is used in assays that have selectivity for one or more different types of bacteria.

In some embodiments, an rcSso7d antigen-binding protein binds to LSP (LMOf2365_0639, a surface protein of *Listeria monocytogenes* (15)).

In some embodiments, an rcSso7d antigen-binding protein binds to OmpA.

In some embodiments, an rcSso7d antigen-binding protein binds to OmpW.

In some embodiments, an rcSso7d antigen-binding protein binds to OmpC.

In some embodiments, an rcSso7d antigen-binding protein binds to OmpF.

In some embodiments, an rcSso7d antigen-binding protein binds to OmpD.

In some embodiments, an rcSso7d antigen-binding protein binds to phoE.

In some embodiments, an rcSso7d antigen-binding protein binds to LMOf2365_0639, a surface protein of *Listeria monocytogenes* (15). In some embodiments, an antigen-binding molecule comprises a reduced charge Sso7d (rcSso7d) antigen-binding protein that specifically binds LMOf2365_0639. The general structure of rcSso7d antigen-binding proteins have been described previously, and rcSso7d antigen-binding proteins that specifically bind LMOf2365_0639 are further described herein.

In some embodiments, an antigen-binding molecule comprises an rcSso7d antigen-binding protein comprising a variable region having:

(i) the amino acid sequence of DGSNCY (SEQ ID NO: 1);
(ii) the amino acid sequence of DGHKCL (SEQ ID NO: 2);
(iii) the amino acid sequence of IKYIDSRWI (SEQ ID NO: 3);
(iv) the amino acid sequence of DGYRCW (SEQ ID NO: 4);
(v) the amino acid sequence of WRAWDAKYI (SEQ ID NO: 5);
(vi) the amino acid sequence of DGHHCW (SEQ ID NO: 6);
(vii) the amino acid sequence of IAYYYYSSIK (SEQ ID NO: 7);
(viii) the amino acid sequence of NIYWWNISY (SEQ ID NO: 8).

In some embodiments, an antigen-binding molecule comprises an rcSso7d antigen-binding protein comprising a variable region that has an amino acid sequence having 2 or 1 amino acid differences relative to one or more of SEQ ID NOs: 1-8.

An "amino acid difference," as used herein, may be an amino acid addition, an amino acid deletion, or an amino acid substitution. In some embodiments, an amino acid difference described herein is an amino acid addition. In some embodiments, an amino acid difference described herein is an amino acid deletion. In some embodiments, an amino acid difference described herein is an amino acid substitution. In some embodiments, the amino acid substitution is a conservative amino acid substitution (i.e., a substitution with an amino acid with similar biochemical properties).

For example, in some embodiments, an antigen-binding molecule comprises an rcSso7d antigen-binding protein comprising a variable region that has an amino acid sequence having 2 or 1 amino acid deletion(s) relative to one or more of SEQ ID NOs: 1-8. In some embodiments, an antigen-binding molecule comprises an rcSso7d antigen-binding protein comprising a variable region that has an amino acid sequence having 2 or 1 amino acid addition(s) relative to one or more of SEQ ID NOs: 1-8. In some embodiments, an antigen-binding molecule comprises an rcSso7d antigen-binding protein comprising a variable region that has an amino acid sequence having 2 or 1 amino acid substitution(s), optionally a conservative amino acid substitution(s), relative to one or more of SEQ ID NOs: 1-8.

In some embodiments, an antigen-binding molecule comprises an rcSso7d antigen-binding protein comprising a scaffold region having:

(i) the amino acid sequence of (SEQ ID NO: 9)
MATVKFTYQGEEKQVDISKIK$X_V$A$X_V$R$X_V$GQ$X_V$I$X_V$F$X_V$YDEGGGA$X_V$G$X_V$G$X_V$VSEKDAPKELLQ;

(ii) the amino acid sequence of (SEQ ID NO: 10)
MATVKFTYQGEEKQVDISKIK$X_v$V$X_v$R$X_v$GQ$X_v$I$X_v$F$X_v$YDEGGGA$X_v$G$X_v$G $X_v$VSEKDAPKELLQ;

(iii) the amino acid sequence of (SEQ ID NO: 11)
MATVKFTYQGEEKQVDISKIK$X_v$A$X_v$$X_v$R$X_v$GQ$X_v$I$X_v$F$X_v$YDEGGGA$X_v$G $X_v$G$X_v$VSEKDAPKELLQ;

or (iv) the amino acid sequence of (SEQ ID NO: 12)
MATVKFTYQGEEKQVDISKIK$X_v$V$X_v$R$X_v$GQ$X_v$I$X_v$F$X_v$L;

wherein $X_v$ corresponds to an amino acid of the variable region.

In some embodiments, an antigen-binding molecule comprises an rcSso7d antigen-binding protein comprising a scaffold region that has an amino acid sequence having ten or fewer, nine or fewer, eight or fewer, seven or fewer, six or fewer, five or fewer, four or fewer, three or fewer, two or fewer, or one amino acid difference(s) with one or more of SEQ ID NOs: 9-12. In some embodiments, the amino acids corresponding to amino acids of the variable region are not considered when determining the number of amino acid differences.

For example, in some embodiments, an antigen-binding molecule comprises an rcSso7d antigen-binding protein comprising a scaffold region that has an amino acid sequence having 10, 9, 8, 7, 6, 5, 4, 3, 2 or 1 amino acid deletion(s) relative to one or more of SEQ ID NOs: 9-12, optionally wherein the amino acids of the variable region are not considered. In some embodiments, an antigen-binding molecule comprises an rcSso7d antigen-binding protein comprising a scaffold region that has an amino acid sequence having 10, 9, 8, 7, 6, 5, 4, 3, 2 or 1 amino acid additions relative to one or more of SEQ ID NOs: 9-12, optionally wherein the amino acids of the variable region are not considered. In some embodiments, an antigen-binding molecule comprises an rcSso7d antigen-binding protein comprising a scaffold region that has an amino acid sequence having 10, 9, 8, 7, 6, 5, 4, 3, 2 or 1, optionally a conservative amino acid substitution(s), relative to one or more of SEQ ID NOs: 9-12, optionally wherein the amino acids of the variable region are not considered.

In some embodiments, an antigen-binding molecule comprises an rcSso7d antigen-binding protein comprising a scaffold region that has at least 80% identity, at least 85% identity, at least 90% identity, at least 95% identity, or at least 98% identity with the amino acid sequence of one or more of SEQ ID NOs: 9-11. In some embodiments, the amino acids corresponding to amino acids of the variable region are not considered when determining the sequence identity. Methods of determining the extent of identity between two sequences (e.g., two amino acid sequences or two polynucleic acids) are known to those having ordinary skill in the art. One exemplary method is the use of Basic Local Alignment Search Tool (BLAST®) software with default parameters (blast.ncbi.nlm.nih.gov/Blast.cgi).

In some embodiments, an antigen-binding molecule comprises an rcSso7d antigen-binding protein comprising:

(i) the amino acid sequence of (SEQ ID NO: 13)
MATVKFTYQGEEKQVDISKIKIAKRYGQIIDFSYDEGGGARGWGIVSEK

DAPKELLQMLEKQ;

(ii) the amino acid sequence of (SEQ ID NO: 14)
MATVKFTYQGEEKQVDISKIKWVRRAGQWIDFAYDEGGGAKGYGIVSEK

DAPKELLQCWKS;

(iii) the amino acid sequence of (SEQ ID NO: 15)
MATVKFTYQGEEKQVDISKIKIAVYRYGQYIYFSYDEGGGASGIGKVSE

KDAPKELLQMLEKQ;

(iv) the amino acid sequence of (SEQ ID NO: 16)
MATVKFTYQGEEKQVDISKIKDVGRSGQNICFYL;

(v) the amino acid sequence of (SEQ ID NO: 17)
MATVKFTYQGEEKQVDISKIKDVGRHGQKICFLL;

(vi) the amino acid sequence of (SEQ ID NO: 18)
MATVKFTYQGEEKQVDISKIKDVGRYGQRICFWL;

or (vii) the amino acid sequence of (SEQ ID NO: 19)
MATVKFTYQGEEKQVDISKIKDVGRHGQHICFWL.

In some embodiments, an antigen-binding molecule comprises an rcSso7d antigen-binding protein that has an amino acid sequence having ten or fewer, nine or fewer, eight or fewer, seven or fewer, six or fewer, five or fewer, four or fewer, three or fewer, two or fewer, or one amino acid difference(s) with one or more of SEQ ID NOs: 13-19. In some embodiments, the amino acids corresponding to amino acids of the variable region are not considered when determining the number of amino acid differences.

For example, in some embodiments, an antigen-binding molecule comprises an rcSso7d antigen-binding protein comprising a scaffold region that has an amino acid sequence having 10, 9, 8, 7, 6, 5, 4, 3, 2 or 1 amino acid deletion(s) relative to one or more of SEQ ID NOs: 13-19, optionally wherein the amino acids of the variable region are not considered. In some embodiments, an antigen-binding molecule comprises an rcSso7d antigen-binding protein comprising an amino acid sequence having 10, 9, 8, 7, 6, 5, 4, 3, 2 or 1 amino acid additions relative to one or more of SEQ ID NOs: 13-19, optionally wherein the amino acids of the variable region are not considered. In some embodiments, an antigen-binding molecule comprises an rcSso7d antigen-binding protein comprising an amino acid sequence having 10, 9, 8, 7, 6, 5, 4, 3, 2 or 1, optionally a conservative amino acid substitution(s), relative to one or more of SEQ ID NOs: 13-19, optionally wherein the amino acids of the variable region are not considered.

In some embodiments, an antigen-binding molecule comprises an rcSso7d antigen-binding protein that has an amino acid sequence that has at least 80% identity, at least 85% identity, at least 90% identity, at least 95% identity, or at least 98% identity with the amino acid sequence of one or more of SEQ ID NOs: 13-19. In some embodiments, the amino acids corresponding to amino acids of the variable region are not considered when determining the sequence identity.

In some embodiments, an rcSso7d antigen-binding protein binds to Native Omp, a protein comprising the amino sequences of *Salmonella typhi* membrane proteins, OmpA, OmpW, OmpC, OmpF, OmpD, and phoE.

In some embodiments, an antigen-binding molecule comprises an rcSso7d antigen-binding protein comprising a variable region having:

(i) the amino acid sequence of WKDSYWIAH (SEQ ID NO: 58);

(ii) the amino acid sequence of SSRGASRYH (SEQ ID NO: 59);

(iii) the amino acid sequence of IAAWWWHRG (SEQ ID NO: 60);

(iv) the amino acid sequence of GWWWWWARY (SEQ ID NO: 61);

(v) the amino acid sequence of WIHGYSIGS (SEQ ID NO: 62);

(vi) the amino acid sequence of WHHWGDIDS (SEQ ID NO: 63);

(vii) the amino acid sequence of WISRNAGYG (SEQ ID NO: 64);

(viii) the amino acid sequence of YSGDSRIIY (SEQ ID NO: 65);

(ix) the amino acid sequence of HNHNDRNRI (SEQ ID NO: 66);

(x) the amino acid sequence of GYAHKRGHG (SEQ ID NO: 67);

(xi) the amino acid sequence of AYNKIIYHH (SEQ ID NO: 68);

(xii) the amino acid sequence of HYAYKGAGH (SEQ ID NO: 69);

(xiii) the amino acid sequence of NYHYKRSYS (SEQ ID NO: 70); or (xix) the amino acid sequence of YIWHWYWSN (SEQ ID NO: 71).

In some embodiments, an antigen-binding molecule comprises an rcSso7d antigen-binding protein comprising a variable region that has an amino acid sequence having 2 or 1 amino acid differences (as defined herein) relative to one or more of SEQ ID NOs: 58-71. For example, in some embodiments, an antigen-binding molecule comprises an rcSso7d antigen-binding protein comprising a variable region that has an amino acid sequence having 2 or 1 amino acid deletion(s) relative to one or more of SEQ ID NOs: 58-71. In some embodiments, an antigen-binding molecule comprises an rcSso7d antigen-binding protein comprising a variable region that has an amino acid sequence having 2 or 1 amino acid addition(s) relative to one or more of SEQ ID NOs: 58-71. In some embodiments, an antigen-binding molecule comprises an rcSso7d antigen-binding protein comprising a variable region that has an amino acid sequence having 2 or 1 amino acid substitution(s), optionally a conservative amino acid substitution(s), relative to one or more of SEQ ID NOs: 58-71.

In some embodiments, an rcSso7d antigen-binding protein that binds to Native Omp comprises a scaffold region having the amino acid sequence of MATVKFTYQGEEKQVDISKIK$X_v$V$X_v$R$X_v$GQ$X_v$I$X_v$F$X_v$YDEGGGA$X_v$G$X_v$G$X_v$VSEKDA PKELLEKQ (SEQ ID NO: 72), wherein $X_v$ corresponds to an amino acid of the variable region. In some embodiments, an antigen-binding molecule comprises an rcSso7d antigen-binding protein comprising a scaffold region that has an amino acid sequence having ten or fewer, nine or fewer, eight or fewer, seven or fewer, six or fewer, five or fewer, four or fewer, three or fewer, two or fewer, or one amino acid difference(s) with SEQ ID NO: 72. In some embodiments, the amino acids corresponding to amino acids of the variable region are not considered when determining the number of amino acid differences.

For example, in some embodiments, an antigen-binding molecule comprises an rcSso7d antigen-binding protein comprising a scaffold region that has an amino acid sequence having 10, 9, 8, 7, 6, 5, 4, 3, 2 or 1 amino acid deletion(s) relative to SEQ ID NO: 72, optionally wherein the amino acids of the variable region are not considered. In some embodiments, an antigen-binding molecule comprises an rcSso7d antigen-binding protein comprising a scaffold region that has an amino acid sequence having 10, 9, 8, 7, 6, 5, 4, 3, 2 or 1 amino acid additions relative to SEQ ID NO: 72, optionally wherein the amino acids of the variable region are not considered. In some embodiments, an antigen-binding molecule comprises an rcSso7d antigen-binding protein comprising a scaffold region that has an amino acid sequence having 10, 9, 8, 7, 6, 5, 4, 3, 2 or 1, optionally a conservative amino acid substitution(s), relative to SEQ ID NO: 72, optionally wherein the amino acids of the variable region are not considered.

In some embodiments, an antigen-binding molecule comprises an rcSso7d antigen-binding protein comprising a scaffold region that has at least 80% identity, at least 85% identity, at least 90% identity, at least 95% identity, or at least 98% identity with the amino acid sequence of SEQ ID NO: 72. In some embodiments, the amino acids corresponding to amino acids of the variable region are not considered when determining the sequence identity.

In some embodiments, an antigen-binding molecule comprises an rcSso7d antigen-binding protein comprising:

(i) the amino acid sequence of

```
(SEQ ID NO: 33)
MATVKFTYQGEEKQVDISKIKXVKRDGQSIYFWYDEGGGAIGAGHVSEK

DAPKELLEKQ;
```

(ii) the amino acid sequence of

```
(SEQ ID NO: 34)
MATVKFTYQGEEKQVDISKIKSVSRRGQGIAFSYD

EGGGARGYGHVSEKDAPKELLEKQ;
```

(iii) the amino acid sequence of

```
(SEQ ID NO: 35)
MATVKFTYQGEEKQVDISKIKIVARAGQWIWFWYD

EGGGAHGRGGVSEKDAPKELLEKQ;
```

(iv) the amino acid sequence of (SEQ ID NO: 36)
MATVKFTYQGEEKQVDISKIKGVWRWGQWIWFWYD

EGGGAAGRGYVSEKDAPKELLEKQ;

(v) the amino acid sequence of (SEQ ID NO: 37)
MATVKFTYQGEEKQVDISKIKWVIRHGQGIYFSYD

EGGGAIGGGSVSEKDAPKELLEKQ;

(vi) the amino acid sequence of (SEQ ID NO: 38)
MATVKFTYQGEEKQVDISKIKWVHRHGQWIGFDYD

EGGGAIGDGSVSEKDAPKELLEKQ;

(vii) the amino acid sequence of (SEQ ID NO: 39)
MATVKFTYQGEEKQVDISKIKWVIRSGQRINFAYD

EGGGAGGYGGVSEKDAPKELLEKQ;

(viii) the amino acid sequence of (SEQ ID NO: 40)
MATVKFTYQGEEKQVDISKIKYVSRGGQDISFRYD

EGGGAIGIGYVSEKDAPKELLEKQ;

(ix) the amino acid sequence of (SEQ ID NO: 41)
MATVKFTYQGEEKQVDISKIKHVNRHGQNIDFRYD

EGGGANGRGIVSEKDAPKELLEKQ;

(x) the amino acid sequence of (SEQ ID NO: 42)
MATVKFTYQGEEKQVDISKIKGVYRAGQHIKFRYD

EGGGAGGHGGVSEKDAPKELLEKQ;

(xi) the amino acid sequence of (SEQ ID NO: 43)
MATVKFTYQGEEKQVDISKIKAVYRNGQKIIFIYD

EGGGAYGHGHVSEKDAPKELLEKQ;

(xii) the amino acid sequence of (SEQ ID NO: 44)
MATVKFTYQGEEKQVDISKIKHVYRAGQYIKFGYD

EGGGAAGGGHVSEKDAPKELLEKQ;

(xiii) the amino acid sequence of (SEQ ID NO: 45)
MATVKFTYQGEEKQVDISKIKNVYRHGQYIKFRYD

EGGGASGYGSVSEKDAPKELLEKQ;

or (xiv) the amino acid sequence of (SEQ ID NO: 46)
MATVKFTYQGEEKQVDISKIKYVIRWGQHIWFYYD

EGGGAWGSGNVSEKDAPKELLEKQ.

In some embodiments, an antigen-binding molecule comprises an rcSso7d antigen-binding protein that has an amino acid sequence having ten or fewer, nine or fewer, eight or fewer, seven or fewer, six or fewer, five or fewer, four or fewer, three or fewer, two or fewer, or one amino acid difference(s) with one or more of SEQ ID NOs: 33-46. In some embodiments, the amino acids corresponding to amino acids of the variable region are not considered when determining the number of amino acid differences.

For example, in some embodiments, an antigen-binding molecule comprises an rcSso7d antigen-binding protein comprising an amino acid sequence having 10, 9, 8, 7, 6, 5, 4, 3, 2 or 1 amino acid deletion(s) relative to one or more of SEQ ID NOs: 33-46, optionally wherein the amino acids of the variable region are not considered. In some embodiments, an antigen-binding molecule comprises an rcSso7d antigen-binding protein comprising an amino acid sequence having 10, 9, 8, 7, 6, 5, 4, 3, 2 or 1 amino acid additions relative to one or more of SEQ ID NOs: 33-46, optionally wherein the amino acids of the variable region are not considered. In some embodiments, an antigen-binding molecule comprises an rcSso7d antigen-binding protein comprising a an amino acid sequence having 10, 9, 8, 7, 6, 5, 4, 3, 2 or 1, optionally a conservative amino acid substitution(s), relative to one or more of SEQ ID NOs: 33-46, optionally wherein the amino acids of the variable region are not considered.

In some embodiments, an antigen-binding molecule comprises an rcSso7d antigen-binding protein that has an amino acid sequence that has at least 80% identity, at least 85% identity, at least 90% identity, at least 95% identity, or at least 98% identity with the amino acid sequence of one or more of SEQ ID NOs: 33-46. In some embodiments, the amino acids corresponding to amino acids of the variable region are not considered when determining the sequence identity.

In some embodiments, an rcSso7d antigen-binding protein binds to *E. coli* OmpW.

In some embodiments, an antigen-binding molecule comprises an rcSso7d antigen-binding protein comprising a variable region having:

(i) the amino acid sequence of WSWYYSIGG (SEQ ID NO: 73);

(ii) the amino acid sequence of IHAWGXWSI (SEQ ID NO: 74), wherein X is any naturally-occurring amino acid, such as wherein X is alanine (A), arginine (R), asparagine (N), aspartic acid (D), cysteine (C), glutamic acid (D), glutamine (Q), glycine, (G), histidine (H), isoleucine (I), leucine (L), lysine (K), methionine (M), phenylalanine (F), proline (P), serine (S), threonine (T), tryptophan (W), tyrosine (Y), or valine (V);

(iii) the amino acid sequence of HSGWDAHDA (SEQ ID NO: 75);

(iv) the amino acid sequence of WSWYYSSGS (SEQ ID NO: 76);

(v) the amino acid sequence of WWWWKYAWI (SEQ ID NO: 77);

(vi) the amino acid sequence of YKWYWIAYN (SEQ ID NO: 78);

(vii) the amino acid sequence of WWWYRYWWI (SEQ ID NO: 79); or (viii) the amino acid sequence of IWWARWGRY (SEQ ID NO: 80).

In some embodiments, an antigen-binding molecule comprises an rcSso7d antigen-binding protein comprising a variable region that has an amino acid sequence having 2 or 1 amino acid differences (as defined herein) relative to one or more of SEQ ID NOs: 73-80. For example, in some embodiments, an antigen-binding molecule comprises an rcSso7d antigen-binding protein comprising a variable region that has an amino acid sequence having 2 or 1 amino acid deletion(s) relative to one or more of SEQ ID NOs: 73-80. In some embodiments, an antigen-binding molecule comprises an rcSso7d antigen-binding protein comprising a variable region that has an amino acid sequence having 2 or 1 amino acid addition(s) relative to one or more of SEQ ID NOs: 73-80. In some embodiments, an antigen-binding molecule comprises an rcSso7d antigen-binding protein comprising a variable region that has an amino acid sequence having 2 or 1 amino acid substitution(s), optionally a conservative amino acid substitution(s), relative to one or more of SEQ ID NOs: 73-80.

In some embodiments, an rcSso7d antigen-binding protein that binds to *E. coli* OmpW comprises a scaffold region having the amino acid sequence of MATVKFTYQGEEKQVDISKIKX$_v$VX$_v$RX$_v$GQX$_v$IX$_v$FX$_v$YDEGGGAX$_v$GX$_v$GX$_v$VSEKDA PKELLEKQ (SEQ ID NO: 72), wherein X$_v$ corresponds to an amino acid of the variable region. In some embodiments, an antigen-binding molecule comprises an rcSso7d antigen-binding protein comprising a scaffold region that has an amino acid sequence having ten or fewer, nine or fewer, eight or fewer, seven or fewer, six or fewer, five or fewer, four or fewer, three or fewer, two or fewer, or one amino acid difference(s) with SEQ ID NO: 72. In some embodiments, the amino acids corresponding to amino acids of the variable region are not considered when determining the number of amino acid differences.

For example, in some embodiments, an antigen-binding molecule comprises an rcSso7d antigen-binding protein comprising a scaffold region that has an amino acid sequence having 10, 9, 8, 7, 6, 5, 4, 3, 2 or 1 amino acid deletion(s) relative to SEQ ID NO: 72, optionally wherein the amino acids of the variable region are not considered. In some embodiments, an antigen-binding molecule comprises an rcSso7d antigen-binding protein comprising a scaffold region that has an amino acid sequence having 10, 9, 8, 7, 6, 5, 4, 3, 2 or 1 amino acid additions relative to SEQ ID NO: 72, optionally wherein the amino acids of the variable region are not considered. In some embodiments, an antigen-binding molecule comprises an rcSso7d antigen-binding protein comprising a scaffold region that has an amino acid sequence having 10, 9, 8, 7, 6, 5, 4, 3, 2 or 1, optionally a conservative amino acid substitution(s), relative to SEQ ID NO: 72, optionally wherein the amino acids of the variable region are not considered.

In some embodiments, an antigen-binding molecule comprises an rcSso7d antigen-binding protein comprising a scaffold region that has at least 80% identity, at least 85% identity, at least 90% identity, at least 95% identity, or at least 98% identity with the amino acid sequence of SEQ ID NO: 72. In some embodiments, the amino acids corresponding to amino acids of the variable region are not considered when determining the sequence identity.

In some embodiments, an antigen-binding molecule comprises an rcSso7d antigen-binding protein comprising:

(i) the amino acid sequence of

```
                                        (SEQ ID NO: 47)
MATVKFTYQGEEKQVDISKIKWVSRWGQYIYFSYD

EGGGAIGGGGVSEKDAPKELLEKQ;
```

(ii) the amino acid sequence of

```
                                        (SEQ ID NO: 48)
MATVKFTYQGEEKQVDISKIKIVHRAGQWIGFXYD

EGGGAWGSGIVSEKDAPKELLEKQ;
```

(iii) the amino acid sequence of

```
                                        (SEQ ID NO: 49)
MATVKFTYQGEEKQVDISKIKHVSRGGQWIDFAYDEGGGAHGDGAVSEK

DAPKELLEKQ;
```

(iv) the amino acid sequence of

```
                                        (SEQ ID NO: 50)
MATVKFTYQGEEKQVDISKIKWVSRWGQYIYFSYDEGGGASGGGSVSEK

DAPKELLEKQ;
```

(v) the amino acid sequence of

```
                                        (SEQ ID NO: 51)
MATVKFTYQGEEKQVDISKIKWVWRWGQWIKFYYDEGGGAAGWGIVSEK

DAPKELLEKQ;
```

(vi) the amino acid sequence of

```
                                        (SEQ ID NO: 52)
MATVKFTYQGEEKQVDISKIKYVKRWGQYIWFIYDEGGGAAGYGNVSEK

DAPKELLEKQ;
```

(vii) the amino acid sequence of

```
                                        (SEQ ID NO: 53)
MATVKFTYQGEEKQVDISKIKWVWRWGQYIRFYYDEGGGAWGWGIVSEK

DAPKELLEKQ;
```

or (viii) the amino acid sequence of

```
                                        (SEQ ID NO: 54)
MATVKFTYQGEEKQVDISKIKIVWRWGQAIRFWYDEGGGAGGRGYVSEK

DAPKELLEKQ.
```

In some embodiments, an antigen-binding molecule comprises an rcSso7d antigen-binding protein that has an amino acid sequence having ten or fewer, nine or fewer, eight or fewer, seven or fewer, six or fewer, five or fewer, four or fewer, three or fewer, two or fewer, or one amino acid difference(s) with one or more of SEQ ID NOs: 47-54. In some embodiments, the amino acids corresponding to amino acids of the variable region are not considered when determining the number of amino acid differences.

For example, in some embodiments, an antigen-binding molecule comprises an rcSso7d antigen-binding protein comprising an amino acid sequence having 10, 9, 8, 7, 6, 5, 4, 3, 2 or 1 amino acid deletion(s) relative to one or more of SEQ ID NOs: 47-54, optionally wherein the amino acids of the variable region are not considered. In some embodiments, an antigen-binding molecule comprises an rcSso7d antigen-binding protein comprising an amino acid sequence having 10, 9, 8, 7, 6, 5, 4, 3, 2 or 1 amino acid additions relative to one or more of SEQ ID NOs: 47-54, optionally wherein the amino acids of the variable region are not considered. In some embodiments, an antigen-binding molecule comprises an rcSso7d antigen-binding protein comprising a an amino acid sequence having 10, 9, 8, 7, 6, 5, 4, 3, 2 or 1, optionally a conservative amino acid substitution(s), relative to one or more of SEQ ID NOs: 47-54, optionally wherein the amino acids of the variable region are not considered.

In some embodiments, an antigen-binding molecule comprises an rcSso7d antigen-binding protein that has an amino acid sequence that has at least 80% identity, at least 85% identity, at least 90% identity, at least 95% identity, or at least 98% identity with the amino acid sequence of one or more of SEQ ID NOs: 47-54. In some embodiments, the amino acids corresponding to amino acids of the variable region are not considered when determining the sequence identity.

In some embodiments, an rcSso7d antigen-binding protein binds to *E. coli* OmpA.

In some embodiments, an antigen-binding molecule comprises an rcSso7d antigen-binding protein comprising a variable region having:

(i) the amino acid sequence of RWWGYWDNW (SEQ ID NO: 81);

(ii) the amino acid sequence of RHYWWRRHH (SEQ ID NO: 82); or (iii) the amino acid sequence of HHWWWW (SEQ ID NO: 83).

In some embodiments, an antigen-binding molecule comprises an rcSso7d antigen-binding protein comprising a variable region that has an amino acid sequence having 2 or 1 amino acid differences (as defined herein) relative to one or more of SEQ ID NOs: 81-83. For example, in some embodiments, an antigen-binding molecule comprises an rcSso7d antigen-binding protein comprising a variable region that has an amino acid sequence having 2 or 1 amino acid deletion(s) relative to one or more of SEQ ID NOs: 81-83. In some embodiments, an antigen-binding molecule comprises an rcSso7d antigen-binding protein comprising a variable region that has an amino acid sequence having 2 or 1 amino acid addition(s) relative to one or more of SEQ ID NOs: 81-83. In some embodiments, an antigen-binding molecule comprises an rcSso7d antigen-binding protein comprising a variable region that has an amino acid sequence having 2 or 1 amino acid substitution(s), optionally a conservative amino acid substitution(s), relative to one or more of SEQ ID NOs: 81-83.

In some embodiments, an rcSso7d antigen-binding protein that binds to *E. coli* OmpA comprises a scaffold region having:

(ii) the amino acid sequence of (SEQ ID NO: 72)
MATVKFTYQGEEKQVDISKIK$X_V$V$X_V$R$X_V$GQ$X_V$I$X_V$F$X_V$YDEGGGA$X_V$G$X_V$G
$X_V$VSEKDAPKELLEKQ
or (ii) the amino acid sequence of (SEQ ID NO: 12)
MATVKFTYQGEEKQVDISKIK$X_V$V$X_V$R$X_V$GQ$X_V$I$X_V$F$X_V$L;

wherein $X_v$ corresponds to an amino acid of the variable region.

In some embodiments, an antigen-binding molecule comprises an rcSso7d antigen-binding protein comprising a scaffold region that has an amino acid sequence having ten or fewer, nine or fewer, eight or fewer, seven or fewer, six or fewer, five or fewer, four or fewer, three or fewer, two or fewer, or one amino acid difference(s) with one or more of SEQ ID NO: 12 and 72. In some embodiments, the amino acids corresponding to amino acids of the variable region are not considered when determining the number of amino acid differences.

For example, in some embodiments, an antigen-binding molecule comprises an rcSso7d antigen-binding protein comprising a scaffold region that has an amino acid sequence having 10, 9, 8, 7, 6, 5, 4, 3, 2 or 1 amino acid deletion(s) relative to SEQ ID NO: 12 or 72, optionally wherein the amino acids of the variable region are not considered. In some embodiments, an antigen-binding molecule comprises an rcSso7d antigen-binding protein comprising a scaffold region that has an amino acid sequence having 10, 9, 8, 7, 6, 5, 4, 3, 2 or 1 amino acid additions relative to SEQ ID NO: 12 or 72, optionally wherein the amino acids of the variable region are not considered. In some embodiments, an antigen-binding molecule comprises an rcSso7d antigen-binding protein comprising a scaffold region that has an amino acid sequence having 10, 9, 8, 7, 6, 5, 4, 3, 2 or 1, optionally a conservative amino acid substitution(s), relative to SEQ ID NO: 12 or 72, optionally wherein the amino acids of the variable region are not considered.

In some embodiments, an antigen-binding molecule comprises an rcSso7d antigen-binding protein comprising a scaffold region that has at least 80% identity, at least 85% identity, at least 90% identity, at least 95% identity, or at least 98% identity with the amino acid sequence of SEQ ID NO: 12 or 72. In some embodiments, the amino acids corresponding to amino acids of the variable region are not considered when determining the sequence identity.

In some embodiments, an antigen-binding molecule comprises an rcSso7d antigen-binding protein comprising:

(i) the amino acid sequence of (SEQ ID NO: 55)
MATVKFTYQGEEKQVDISKIKRVWRWGQGIYFWYDEGGGADGNGWVSEK
DAPKELLEKQ;

(ii) the amino acid sequence of (SEQ ID NO: 56)
MATVKFTYQGEEKQVDISKIKRVHRYGQWIWFRYDEGGGARGHGHVSEK

DAPKELLEKQ;

or (iii) the amino acid sequence of (SEQ ID NO: 57)
MATVKFTYQGEEKQVDISKIKHVHRWGQWIWFWL.

In some embodiments, an antigen-binding molecule comprises an rcSso7d antigen-binding protein that has an amino acid sequence having ten or fewer, nine or fewer, eight or fewer, seven or fewer, six or fewer, five or fewer, four or fewer, three or fewer, two or fewer, or one amino acid difference(s) with one or more of SEQ ID NOs: 55-57. In some embodiments, the amino acids corresponding to amino acids of the variable region are not considered when determining the number of amino acid differences.

For example, in some embodiments, an antigen-binding molecule comprises an rcSso7d antigen-binding protein comprising an amino acid sequence having 10, 9, 8, 7, 6, 5, 4, 3, 2 or 1 amino acid deletion(s) relative to one or more of SEQ ID NOs: 55-57, optionally wherein the amino acids of the variable region are not considered. In some embodiments, an antigen-binding molecule comprises an rcSso7d antigen-binding protein comprising an amino acid sequence having 10, 9, 8, 7, 6, 5, 4, 3, 2 or 1 amino acid additions relative to one or more of SEQ ID NOs: 55-57, optionally wherein the amino acids of the variable region are not considered. In some embodiments, an antigen-binding molecule comprises an rcSso7d antigen-binding protein comprising a an amino acid sequence having 10, 9, 8, 7, 6, 5, 4, 3, 2 or 1, optionally a conservative amino acid substitution(s), relative to one or more of SEQ ID NOs: 55-57, optionally wherein the amino acids of the variable region are not considered.

In some embodiments, an antigen-binding molecule comprises an rcSso7d antigen-binding protein that has an amino acid sequence that has at least 80% identity, at least 85% identity, at least 90% identity, at least 95% identity, or at least 98% identity with the amino acid sequence of one or more of SEQ ID NOs: 55-57. In some embodiments, the amino acids corresponding to amino acids of the variable region are not considered when determining the sequence identity.

In some embodiments, an antigen-binding molecule comprises an enzyme, a fluorescent protein, an immunoglobulin, a peptide tag, a small molecule, or a combination thereof.

In some embodiments, an antigen-binding molecule comprises an enzyme. In some embodiments, the enzyme is selected from the group consisting of alkaline phosphatase, horseradish peroxidase, and β-galactosidase.

In some embodiments, an antigen-binding molecule comprises an immunoglobulin. In some embodiments, the immunoglobulin specifically binds to LMOf2365_0639. In some embodiments, the immunoglobulin does not bind to LMOf2365_0639; for example, in some embodiments, the immunoglobulin specifically binds to a non-LMOf2365_0639 target on the surface of a cell (e.g., *L. monocytogenes* cell).

In some embodiments, an antigen-binding molecule comprises a fluorescent protein. In some embodiments, the fluorescent protein is selected from the group consisting of TagBFP, mTagBFP2, Azurite, EBFP2, EBFP2, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, Monomeric Azami Green, TagGFP2, mUKG, mWasabi, Clover, mNeonGreen, EYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, and NirFP.

In some embodiments, an antigen-binding molecule comprises a peptide tag. In some embodiments, the peptide tag is selected from the group consisting of a His tag, a biotin acceptor tag, an HA tag, a c-Myc tag, a streptavidin tag, and a FLAG tag.

In some embodiments, an antigen-binding molecule comprises a small molecule. In some embodiments, the small molecule is a fluorescent molecule. Examples of fluorescent small molecules are known to those having ordinary skill in the art. In some embodiments, the small molecule is biotin. In some embodiments, the small molecule is cytotoxic.

In some aspects, the disclosure relates to polynucleic acid molecules comprising a nucleic acid sequence encoding an antigen-binding molecule described herein (or the proteinaceous portion thereof).

II. Compositions Comprising an Antigen-Binding Molecules.

In some aspects, the disclosure relates to compositions comprising an antigen-binding molecule described herein. In some embodiments, a composition comprises a plurality of antigen-binding molecules, wherein each of the antigen-binding molecules are the same. In some embodiments, a composition comprises a plurality of antigen-binding molecules, wherein two or more of the antigen-binding molecules are chemically distinct, e.g., having different amino acid sequences, such as different variable region amino acid sequences. For example, in some embodiments, a composition comprises two or more, three or more, four or more, five or more, six or more, seven or more, eight or more, nine or more, or ten or more chemically distinct antigen-binding molecules. In some embodiments, a composition comprises 1-2, 1-3, 1-4, 1-5, 1-6, 1-7, 1-8, 1-9, 1-10, 2-3, 2-4, 2-5, 2-6, 2-7, 2-8, 2-9, 2-10, 3-4, 3-5, 3-6, 3-7, 3-8, 3-9, 3-10, 4-5, 4-6, 4-7, 4-8, 4-9, 4-10, 5-6, 5-7, 5-8, 5-9, 5-10, 6-7, 6-8, 6-9, 6-10, 7-8, 7-9, 7-10, 8-9, 8-10, or 9-10 chemically distinct antigen-binding molecules. In some embodiments, a composition comprises 1, 2, 3, 4, 5, 6, 7, 8, 9, or 10 chemically distinct antigen-binding molecules.

In some embodiments, a composition further comprises a substrate. In some embodiments, the substrate comprises paper, nitrocellulose, cellulose powder, and/or a liquid colloid. In some embodiments, an antigen-binding molecule described herein is localized on the substrate. For example, in some embodiments, an antigen-binding molecule is localized at an interface. The interface can be solid as in a functional cellulose, or at the surface of a particle, of at the surface of a liquid-liquid colloid. See e.g., Miller et al., Beyond Epitope Binning: Directed in Vitro Selection of Complementary Pairs of Binding Proteins, ACS Combinatorial Science, 2020, 22 (1), 49-60; Sung et al., Binding performance of engineered rcSso7d affinity reagents versus commercial antibodies against Zika virus NS1, Analyst, 2020 145, 2515-2519; Zhang et al., Emulsion Agglutination Assay for the Detection of Protein-Protein Interactions: An Optical Sensor for Zika Virus, ACS Sensors, 2019, 4 (1): 180-184, the contents of each of which is incorporated herein. Nanoparticles can be used to produce optical signals or can be magnetic. Functionalization of magnetic particles with the antigen binding proteins selected by the methods described here, can be used to localize, separate, and/or concentrate bacteria. Attachment to liquid colloids can also provide methods to create optical signals for the detection.

In some embodiments, a composition further comprises a buffer.

In some embodiments, the buffer has a pH of less than or equal to 6.0, less than or equal to 5.9, less than or equal to 5.8, less than or equal to 5.7, less than or equal to 5.6, less than or equal to 5.5, less than or equal to 5.4, less than or equal to 5.3, less than or equal to 5.2, less than or equal to 5.1, less than or equal to 5.0, less than or equal to 4.9, less than or equal to 4.8, less than or equal to 4.7, less than or equal to 4.6, less than or equal to 4.5, less than or equal to 4.4, less than or equal to 4.3, less than or equal to 4.2, less than or equal to 4.1, or less than or equal to 4.0. In some embodiments, the buffer has a pH of about 4.0 to about 6.0, about 4.0 to about 5.5, about 4.0 to about 5.0, about 4.0 to about 4.5, about 4.5 to about 6.0, about 5.0 to about 6.0, about 5.5 to about 6.0, or about 4.5 to about 5.0. In some embodiments, the buffer has a pH of about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 4.7, about 5.8, about 5.9, or about 6.0.

In some embodiments, the buffer comprises sodium acetate and/or phosphate-buffered saline.

In some embodiments, the composition contains growth media that promote the proliferation of bacteria.

In some embodiments, the composition comprises a LMOf2365_0639 protein.

In some embodiments, the composition comprises a *Listeria monocytogenes* cell, a *Salmonella typhi* cell, and/or an *E. coli* cell. In some embodiments, the composition comprises a viable *Listeria monocytogenes* cell, a *Salmonella typhi* cell, and/or an *E. coli* cell.

III. Methods of Detection.

In some aspects, the disclosure relates to methods of detection that utilize an antigen-binding molecule described herein or a composition comprising an antigen-binding molecule described herein.

In some aspects, the disclosure relates to methods of detecting bacteria in a sample. In some embodiments, the method comprises: (a) contacting the sample with an antigen-binding molecule described herein or a composition comprising an antigen-binding molecule described herein; and (b) detecting, if present, bacteria bound by the antigen-binding molecule.

In some aspects, the disclosure relates to methods of detecting a *Listeria monocytogenes* cell (e.g., a viable cell) in a sample. In some embodiments, the method comprises: (a) contacting the sample with an antigen-binding molecule described herein or a composition comprising an antigen-binding molecule described herein; and (b) detecting, if present, *Listeria monocytogenes* bound by the antigen-binding molecule.

In some aspects, the disclosure relates to methods of detecting a *Salmonella typhi* cell (e.g., a viable cell) in a sample. In some embodiments, the method comprises: (a) contacting the sample with an antigen-binding molecule described herein or a composition comprising an antigen-binding molecule described herein; and (b) detecting, if present, *Salmonella typhi* bound by the antigen-binding molecule.

In some aspects, the disclosure relates to methods of detecting a *E. coli* cell (e.g., a viable cell) in a sample. In some embodiments, the method comprises: (a) contacting the sample with an antigen-binding molecule described herein or a composition comprising an antigen-binding molecule described herein; and (b) detecting, if present, *E. coli* bound by the antigen-binding molecule.

In some aspects, the disclosure relates to methods of detecting a protein, a glycosylated protein, or a carbohydrate-based antigen associated with a bacteria of interest in a sample. In some embodiments, the antigen is associated with an intact organism and in others the organism is not intact (e.g., its cell membrane and/or cell wall has been disrupted).

In some aspects, the disclosure relates to methods of detecting protein LSP (such as LMOf2365_0639), OmpA, OmpW, OmpC, OmpF, OmpD, phoE, or a combination thereof in a sample. In some embodiments, the method comprises: (a) contacting the sample with an antigen-binding molecule described herein or a composition comprising an antigen-binding molecule described herein; and (b) detecting, if present, LSP (such as LMOf2365_0639), OmpA, OmpW, OmpC, OmpF, OmpD and/or phoE bound by the antigen-binding molecule.

In some embodiments of the methods described herein, the sample is from a food product. In some embodiments, the food product is produced from a food source that is commonly contaminated with *Listeria monocytogenes*. Exemplary food sources commonly contaminated with *Listeria monocytogenes* are known to those having ordinary skill in the art and include soft cheeses made with unpasteurized milk (e.g., queso fresco, queso blanco, panela (queso panela), brie, Camembert, blue-veined, feta); raw sprouts (including alfalfa, clover, radish, and mung bean sprouts); melons; certain meat products (hot dogs, pâté, meat spreads, lunch meats, cold cuts, other deli meats (such as bologna), fermented or dry sausages); cold smoked fish, such as salmon, trout, whitefish, cod, tuna, and mackerel; raw (unpasteurized) milk and products made from it (soft cheese, ice cream, yogurt).

In some embodiments of the methods described herein, the sample is from a subject. In some embodiments, the subject is a mammal. In some embodiments, the subject is a human. In some embodiments, the method further comprises treating the subject if LMOf2365_0639 protein is present in the sample. For example, in some embodiments, the subject is treated for listeriosis. Methods of treating listeriosis are described herein (i.e., methods of killing a *Listeria monocytogenes* cell). Additional methods of treating listeriosis are known to those having ordinary skill in the art.

In some embodiments, the sample is from a surface used to prepare a food or beverage. In some embodiments, the sample is of soil or water.

In some embodiments of the methods described herein, the sample is contacted with the antigen-binding protein in a buffer have a specific pH. For example, in some embodiments, the buffer has a pH of less than or equal to 6.0, less than or equal to 5.9, less than or equal to 5.8, less than or equal to 5.7, less than or equal to 5.6, less than or equal to 5.5, less than or equal to 5.4, less than or equal to 5.3, less than or equal to 5.2, less than or equal to 5.1, less than or equal to 5.0, less than or equal to 4.9, less than or equal to 4.8, less than or equal to 4.7, less than or equal to 4.6, less than or equal to 4.5, less than or equal to 4.4, less than or equal to 4.3, less than or equal to 4.2, less than or equal to 4.1, or less than or equal to 4.0. In some embodiments, the buffer has a pH of about 4.0 to about 6.0, about 4.0 to about 5.5, about 4.0 to about 5.0, about 4.0 to about 4.5, about 4.5 to about 6.0, about 5.0 to about 6.0, about 5.5 to about 6.0, or about 4.5 to about 5.0. In some embodiments, the buffer has a pH of about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 4.7, about 5.8, about 5.9, or about 6.0.

In some embodiments, the buffer comprises sodium acetate and/or phosphate-buffered saline.

In some embodiments of the methods described herein, the method step (a) further comprises contacting the sample with a detection agent, wherein the detection agent binds to or is bound by the antigen-binding molecule. In some embodiments, a detection agent comprises an enzyme, a fluorescent protein, an immunoglobulin, a peptide tag, a small molecule, and/or a combination thereof.

In some embodiments, an antigen-binding molecule comprises an enzyme. In some embodiments, the enzyme is selected from the group consisting of alkaline phosphatase, horseradish peroxidase, and β-galactosidase.

In some embodiments, a detection agent comprises an immunoglobulin that binds to an antigen-binding molecule described herein.

In some embodiments, a detection agent comprises a fluorescent protein. In some embodiments, the fluorescent protein is selected from the group consisting of TagBFP, mTagBFP2, Azurite, EBFP2, EBFP2, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, Monomeric Azami Green, TagGFP2, mUKG, mWasabi, Clover, mNeonGreen, EYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, and NirFP.

In some embodiments, a detection agent comprises a peptide tag. In some embodiments, the peptide tag is selected from the group consisting of a His tag, a biotin acceptor tag, an HA tag, a c-Myc tag, a streptavidin tag, and a FLAG tag.

In some embodiments, a detection agent comprises a small molecule. In some embodiments, the small molecule is a fluorescent molecule. Examples of fluorescent small molecules are known to those having ordinary skill in the art. In some embodiments, the small molecule is biotin.

IV. Methods of Killing a Bacterial Cell.

In some aspects, the disclosure relates to methods of killing a bacterial cell comprising contacting the bacterial cell with an antigen-binding molecule described herein.

In some embodiments, the bacterial cell is a *Listeria monocytogenes* cell, and the method comprises contacting the *Listeria monocytogenes* cell with an antigen-binding molecule described herein that binds to LMOf2365_0639 (or a composition comprising an antigen-binding molecule described herein that binds to LMOf2365_0639), wherein the antigen-binding molecule comprises a cytotoxic agent.

In some embodiments, the bacterial cell is a *Salmonella typhi* cell, and the method comprises contacting the *Listeria monocytogenes* cell with an antigen-binding molecule described herein that binds to Native Omp, said Native Omp comprising the amino acid sequence of *Salmonella typhi* membrane proteins OmpA, OmpW, OmpC, OmpF, OmpD, and phoE (or a composition comprising an antigen-binding molecule described herein that binds to Native Omp), wherein the antigen-binding molecule comprises a cytotoxic agent.

In some embodiments, the bacterial cell is an *E. coli* cell, and the method comprises contacting the *E. coli* cell with an antigen-binding molecule described herein that binds to OmpW (or a composition comprising an antigen-binding molecule described herein that binds to OmpW), wherein the antigen-binding molecule comprises a cytotoxic agent.

In some embodiments of the methods described herein, the sample is contacted with the antigen-binding protein in a buffer have a specific pH. For example, in some embodiments, the buffer has a pH of less than or equal to 6.0, less than or equal to 5.9, less than or equal to 5.8, less than or equal to 5.7, less than or equal to 5.6, less than or equal to 5.5, less than or equal to 5.4, less than or equal to 5.3, less than or equal to 5.2, less than or equal to 5.1, less than or equal to 5.0, less than or equal to 4.9, less than or equal to 4.8, less than or equal to 4.7, less than or equal to 4.6, less than or equal to 4.5, less than or equal to 4.4, less than or equal to 4.3, less than or equal to 4.2, less than or equal to 4.1, or less than or equal to 4.0. In some embodiments, the buffer has a pH of about 4.0 to about 6.0, about 4.0 to about 5.5, about 4.0 to about 5.0, about 4.0 to about 4.5, about 4.5 to about 6.0, about 5.0 to about 6.0, about 5.5 to about 6.0, or about 4.5 to about 5.0. In some embodiments, the buffer has a pH of about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 4.7, about 5.8, about 5.9, or about 6.0.

In some embodiments, the buffer comprises sodium acetate and/or phosphate-buffered saline.

V. Methods of Monitoring the Growth of a Population of Bacteria.

In some aspects, the disclosure relates to methods of monitoring growth of a population of bacteria. In some embodiments, the method comprises: (a) contacting a sample comprising at least a subset of the population with an antigen-binding molecule described herein or a composition comprising an antigen-binding molecule described herein; and (b) repeating step (a) at least once.

In some embodiments, step (a) further comprises contacting these sample with a detection agent described in "Methods of Detection" above.

VI. Kits.

In some aspects, the disclosure relates to kits comprising an antigen-binding molecule described herein (or a composition comprising an antigen-binding molecule described herein).

In some embodiments, a kit further comprises a substrate. In some embodiments, the substrate is selected from the group consisting of paper, nitrocellulose, cellulose powder, and liquid colloid. In some embodiments, an antigen-binding molecule is bound to the substrate.

EXAMPLES

Example 1: Identification of rcSso7d Variants that Bind *L. monocytogenes* Surface Protein In this study, the rcSso7d binding scaffold was used as the affinity reagent for development, due to its previous demonstration as an alternative scaffold that is robust, easy to produce, straightforward for engineering new variants, and has similar functional performance to antibodies (16-22). In order to identify an rcSso7d variant that detects *L. monocytogenes*, a combinatorial *Saccharomyces cerevisiae* library was used consisting of $1.4\times10^9$ different rcSso7d variants in a yeast-surface display platform (FIG. 1A) (16, 23). The rcSso7d combinatorial library has a variable binding face (FIG. 1B, red) and is expressed on the surface of yeast via the native a-agglutinin proteins Aga1p/Aga2p with c-Myc and HA (hemagglutinin) epitope tags for labeling (FIG. 1B). Therefore, by selecting cells with specific physical characteristics (i.e. binding to the target), one can isolate the genetic sequence encoding for that specific rcSso7d variant.

Figures 6A, 6B, 6C:
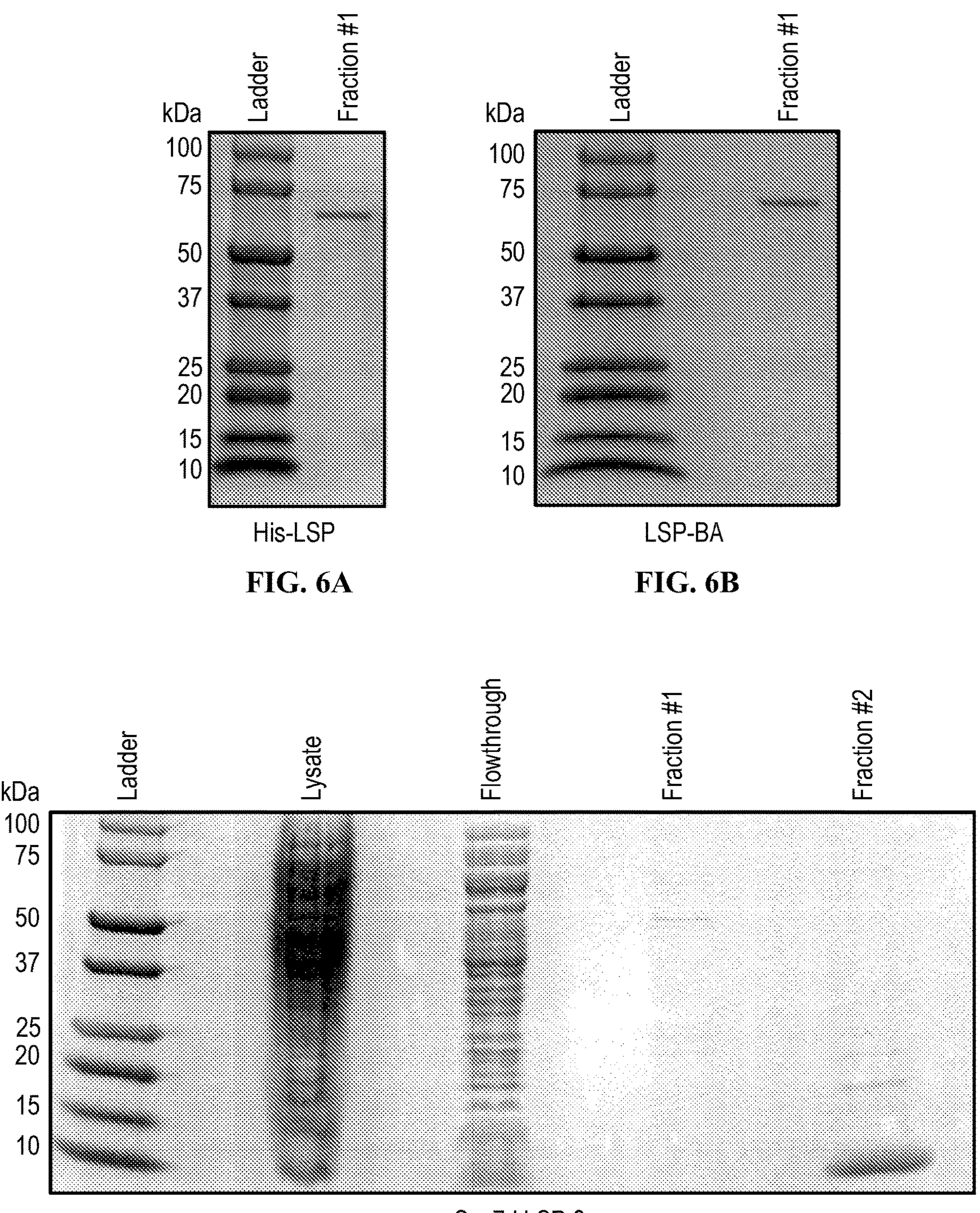
FIGS. 6A-6C. SDS-PAGE gel images for (FIG. 6A) His-LSP, (FIG. 6B) LSP-BA, and (FIG. 6C) rcSso7d.LSP.3 after purification on Ni-NTA columns. His-LSP (FIG. 6A) and LSP-BA (FIG. 6B) were collected into one fraction each and both demonstrated high purity. Gel image for rcSso7d.LSP.3 (FIG. 6C) shows lanes with the clarified lysate prior to purification, the flowthrough after loading the Ni-NTA column, and the two fractions collected during purification. Fraction #2 was used based on presence and purity of the product.

To develop affinity reagents against *L. monocytogenes* whole cells, a *L. monocytogenes* surface protein ("LSP") identified in Zhang, et al, called LMOf2365_0639 (15) was targeted (FIG. 1C). The LMOf2365_0639 protein was found to have epitopes that were conserved in various *L. monocytogenes* strains but variable among other *Listeria* species, making it a promising surface-exposed biomarker for *L. monocytogenes* (15). LSP was recombinantly produced in *E. coli* as two variants: one variant was constructed with just an N-terminal 6×-hexahistidine (His) tag for purification and labeling ("His-LSP") while another variant was cloned with both an N-terminal His tag for purification and a C-terminal biotin acceptor tag (BA) for labeling ("LSP-BA"). Having two different versions of the target protein allows for oriented selection since using a tag on one side of the target protein for labeling may prevent development of affinity reagents against epitopes around that tag due to steric hindrance with the labeling reagents. His-LSP and LSP-BA were expressed and purified on Ni-NTA immobilized metal affinity chromatography (IMAC) following similar protocols as previously described (17) (FIGS. 6A-6C).

Using the rcSso7d library, directed evolution techniques were used to enrich the library for affinity reagents against LSP. In general, magnetic bead sorting (MBS) was conducted to first enrich the library for any rcSso7d clones with binding affinity towards the target protein. After sufficient enrichment, fluorescence activated cell sorting (FACS) was conducted to further enrich for high affinity clones in a controlled fashion. To increase the possibility of developing affinity clones that target a surface exposed epitope of LSP, three different selection schemes using the two different label-oriented LSP variants were used.

Figure 7:
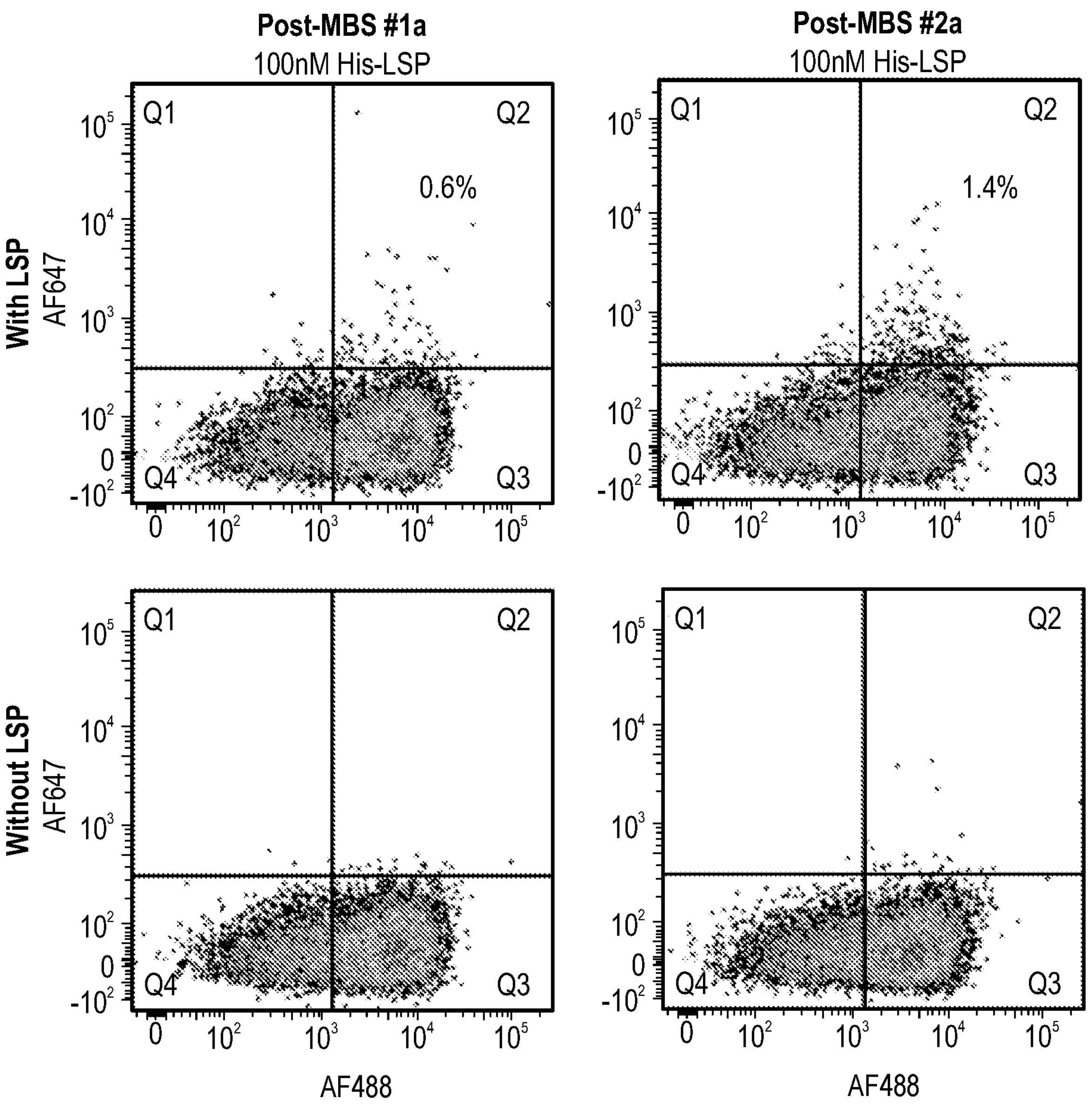
FIG. 7. FACS dot plots for the post-MBS sub-libraries (left: post-MBS #1 and right: post-MBS #2; "a" denotes that these are the rounds of MBS conducted using His-LSP. Samples shown in the top plots were incubated with His-LSP, and samples shown in the bottom plots were incubated without His-LSP. Percentages shown indicate the percentage of the population in the upper quadrants.
Figure 8:
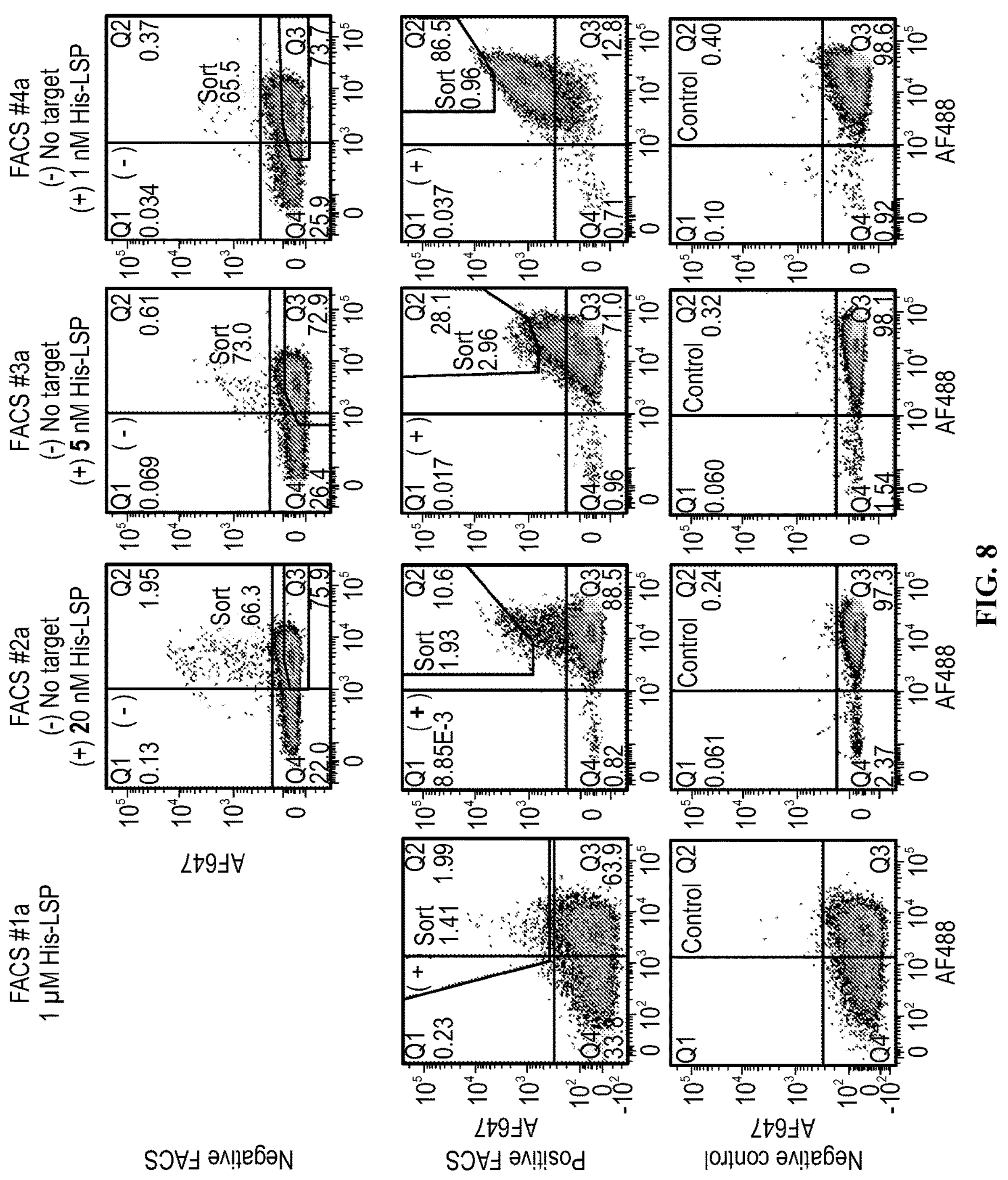
FIG. 8. FACS dot plots for the FACS selections against His-LSP, originating from the MBS population screened using His-LSP (FACS "a"). Negative sorts (top row) were conducted prior to positive sorts (middle row) for FACS #2a, #3a, and #4a. Bottom row depicts the negative controls (samples incubated without His-LSP) for the positive FACS sub-populations. Concentration of His-LSP used are listed above the plots, with a reduction in concentration from 1 μM to 1 nM for increased stringency. Numbers indicate the percentage of the population in each quadrant. Gates drawn indicate the gates used for sorting.

In the first selection scheme, MBS was conducted using Ni-NTA magnetic beads coated with N-terminal His-LSP. Moderate enrichment was observed after two rounds of MBS (FIG. 7) with sufficient reduction in library diversity to proceed to FACS. Using this post-MBS sub-library, four rounds of FACS were conducted with His-LSP, using the N-terminal His tag on LSP to label target binding and the N-terminal HA tag on the displayed yeast to label for surface expression of rcSso7d (FACS "a"; FIG. 2 and FIG. 8). To reduce non-specific clones, negative FACS selections were conducted against the labeling reagents (mouse anti-His antibody and goat anti-mouse AF647) for FACS #2a, #3a, and #4a by incubating the populations with labeling reagents in the absence of target LSP and collecting the clones without binding signal (21) (FIG. 8). The collected cells were then immediately relabeled with His-LSP for positive FACS.

Figures 3A, 3B:
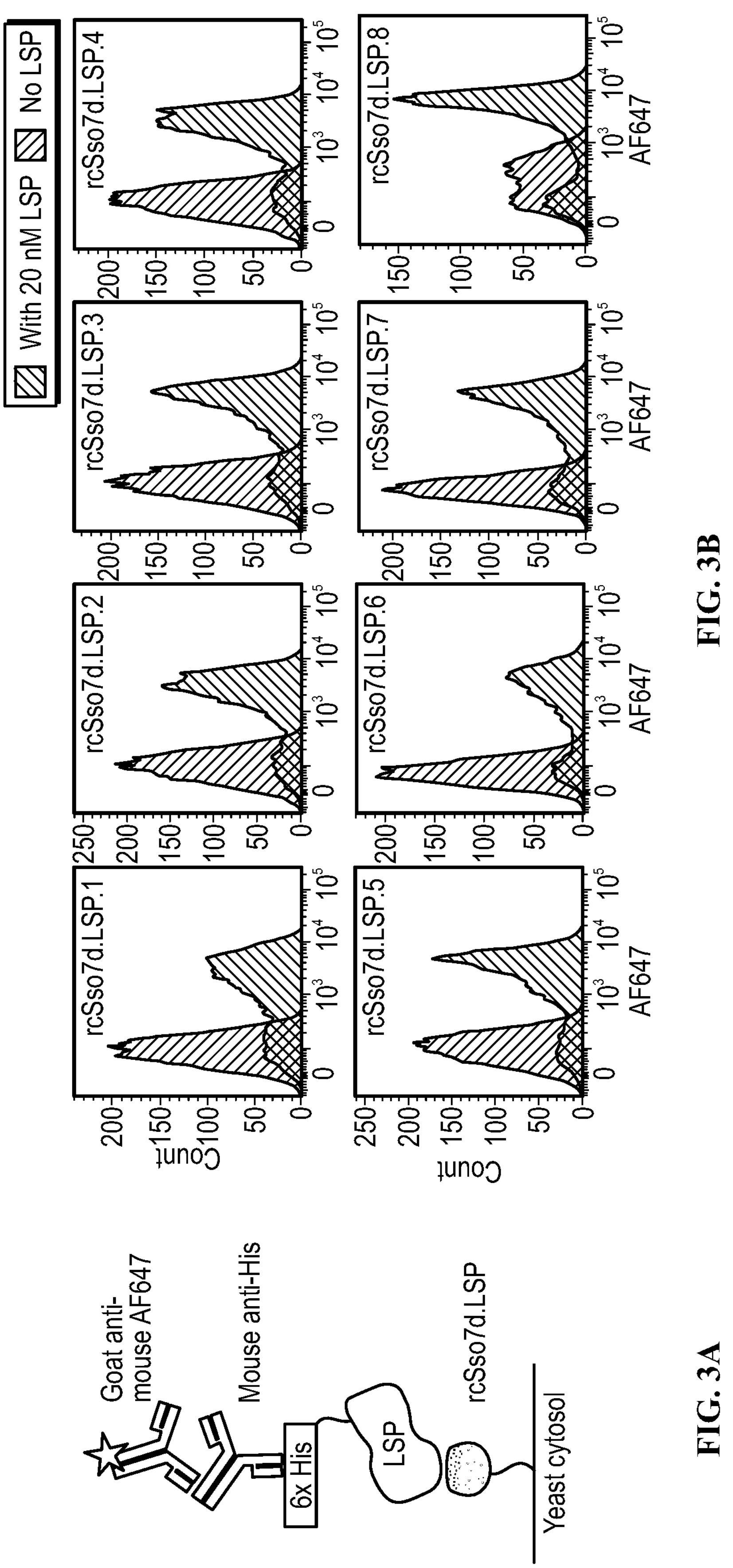
FIGS. 3A-3B. Target-specific binding of identified rcSso7d clones.

To analyze the resulting library diversity after FACS #4a, a subset of the population were sequenced; 30 clones were submitted for sequencing, and five unique clones were identified (TABLE 1; clones 1, 2, 3, 4, and 5). Over 80% of the sequences resulted in the same sequence—clone 1—which indicates a fairly monoclonal population. Clones 1, 2, and 4 had very similar sequences and contained an early stop codon mutation, leading to truncated sequences at approximately 50% of the full length sequence. There was uncertainty about whether the truncated sequences would be folded properly and the possibility that they may be non-specific binding proteins. However, after testing the clonal yeast in yeast-surface display, it was found that all five of the identified sequences—full length and truncated—demonstrated target-specific binding to LSP (FIGS. 3A-3B).

TABLE 1

Amino acid sequences for the binding face of each unique rcSso7d clone identified.

| Clone | Binding face sequence | SEQ ID NO: |
|---|---|---|
| rcSso7d.LSP.1 | DGSNCY | 1 |
| rcSso7d.LSP.2 | DGHKCL | 2 |
| rcSso7d.LSP.3 | IKYIDSRWI | 3 |
| rcSso7d.LSP.4 | DGYRCW | 4 |
| rcSso7d.LSP.5 | WRAWDAKYI | 5 |
| rcSso7d.LSP.6 | DGHHCW | 6 |
| rcSso7d.LSP.7 | IAYYYYSSIK | 7 |
| rcSso7d.LSP.8 | NIYWWNISY | 8 |

Figure 9:
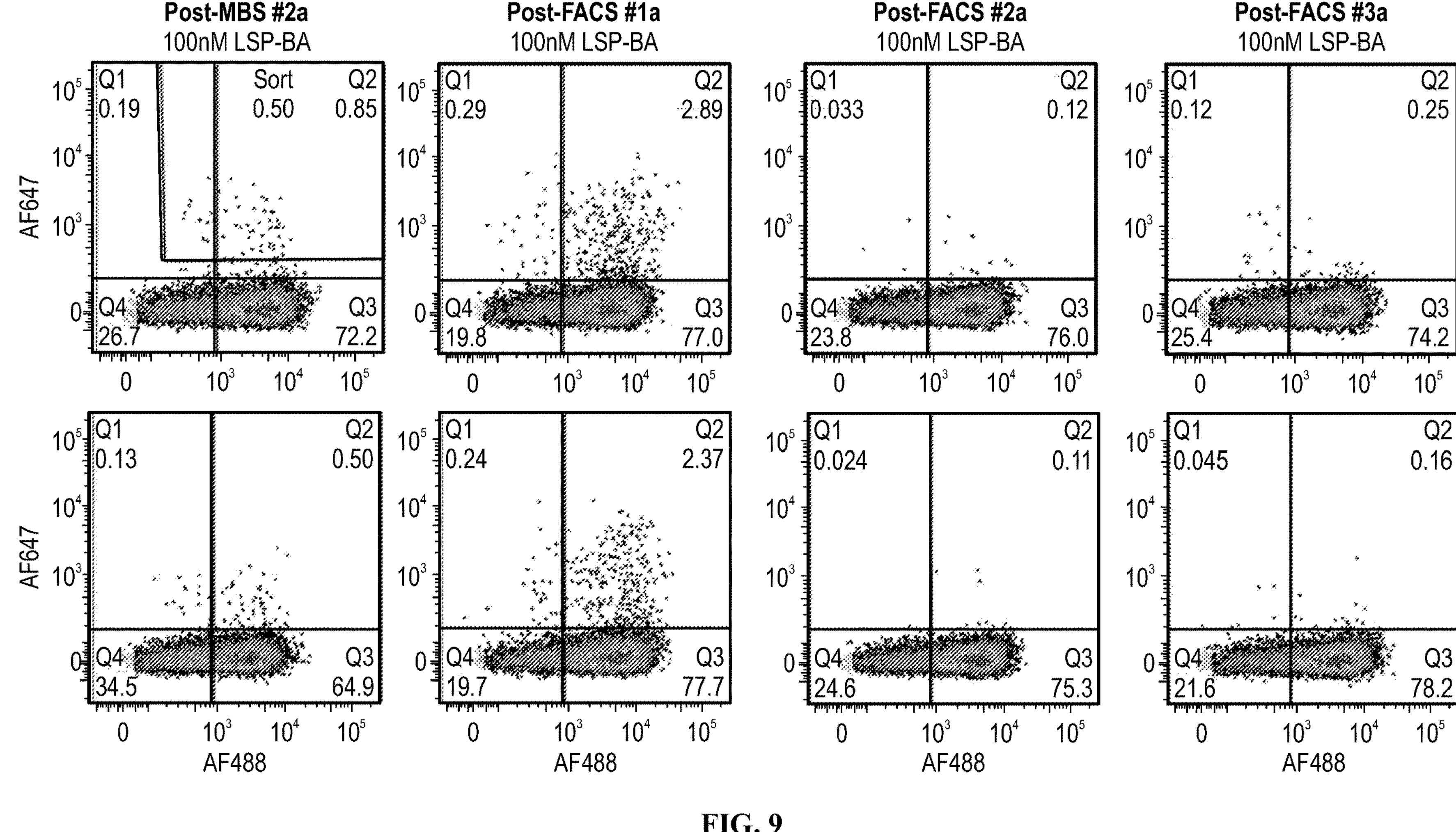
FIG. 9. FACS dot plots for the sub-libraries generated from MBS and FACS selections against His-LSP. The sub-libraries were challenged against LSP-BA to assess whether the orientation of the target label (N-terminus vs. C-terminus) affects the sorting populations. Low levels of positive binding were seen in all sub-libraries.

To assess whether the His-LSP-enriched sub-libraries also demonstrate binding to LSP-BA—with the tag used for labeling on the C-terminus instead of the N-terminus of the LSP—these sub-libraries were challenged against LSP-BA. Relatively low levels of binding was found to LSP-BA across all the sub-libraries (FIG. 9), suggesting that the clones enriched during selections using N-terminal-tagged LSP bind to an epitope that is inaccessible when using a C-terminal tag to label the LSP.

Figure 10:
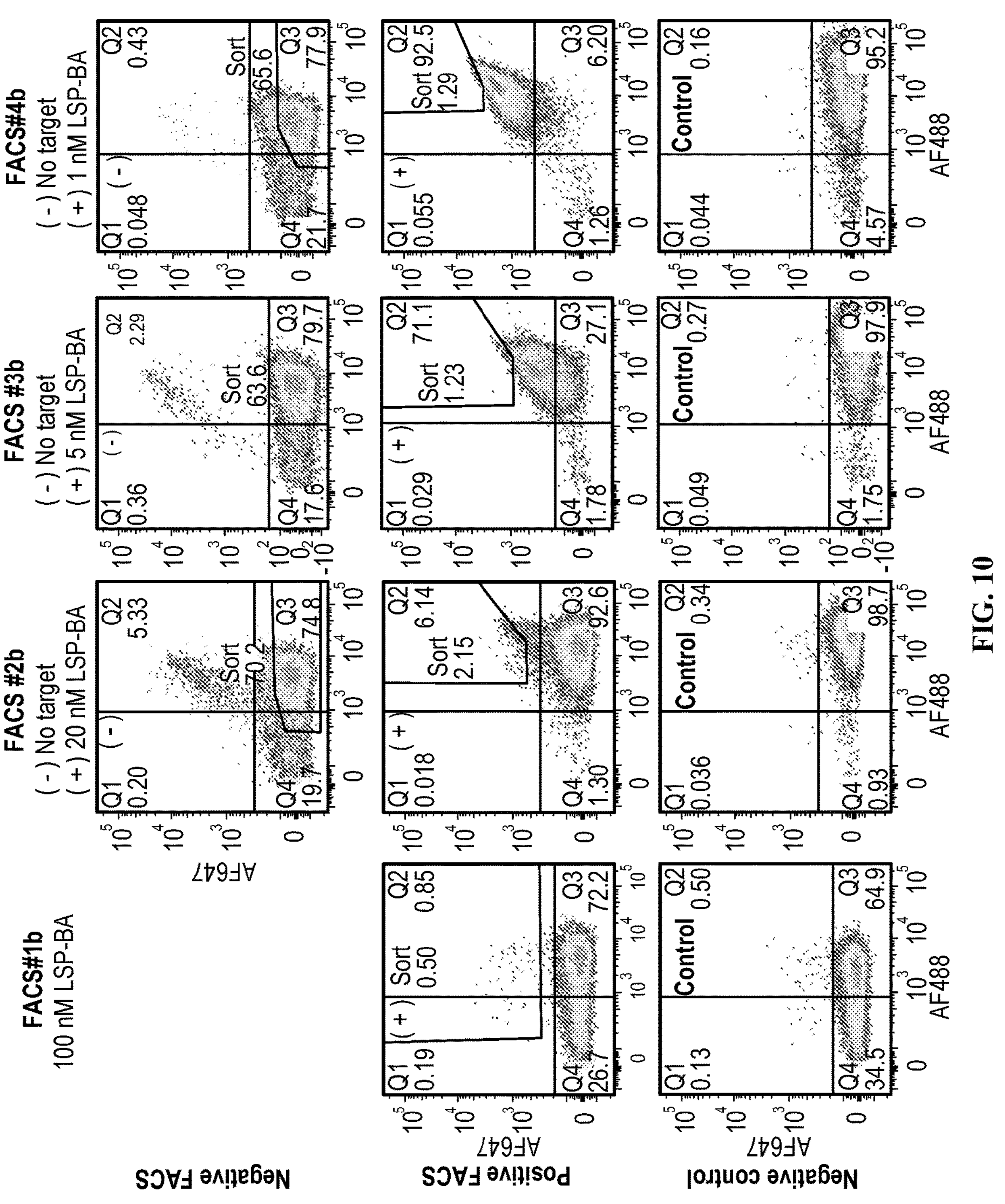
FIG. 10. FACS dot plots for the FACS selections against LSP-BA, originating from the MBS population screened using His-LSP (FACS "b"). Negative sorts (top row) were conducted prior to positive sorts (middle row) for FACS #2b, #3b, and #4b. Bottom row depicts the negative controls (samples incubated without LSP-BA) for the positive FACS sub-populations. Concentration of LSP-BA used are listed above the plots, with a reduction in concentration from 100 nM to 1 nM for increased stringency. Numbers indicate the percentage of the population in each quadrant. Gates drawn indicate the gates used for sorting.

In order to identify additional rcSso7d clones that may target alternative epitopes of LSP, a second selection scheme was produced using the His-LSP-enriched post-MBS sub-library. Four rounds of FACS was conducted with LSP-BA, using the C-terminal biotin tag to label target binding (FACS "b"; FIG. 2 and FIG. 10). Negative FACS rounds were conducted against the labeling reagent streptavidin (SA) AF647 in FACS #2b, #3b, and #4b to down-select for off-target binding clones. After analyzing the sequences from post-FACS #4b, it was found that over 90% of the sequences resulted in the same sequence as clone 1, indicating that these selections using LSP-BA for FACS identified the same rcSso7d variant as selections using His-LSP for FACS. One unique sequence was also identified (clone 6; TABLE 1), which was similar to the truncated sequences previously identified (clones 1, 2, and 4). These results suggest a lack of diversity in the enriched clones, even after using different orientation tags on the LSP. Conducting MBS using His-LSP may have applied early selective pressure for affinity clones targeting similar epitopes, even when FACS was conducted using LSP-BA.

Figure 11:
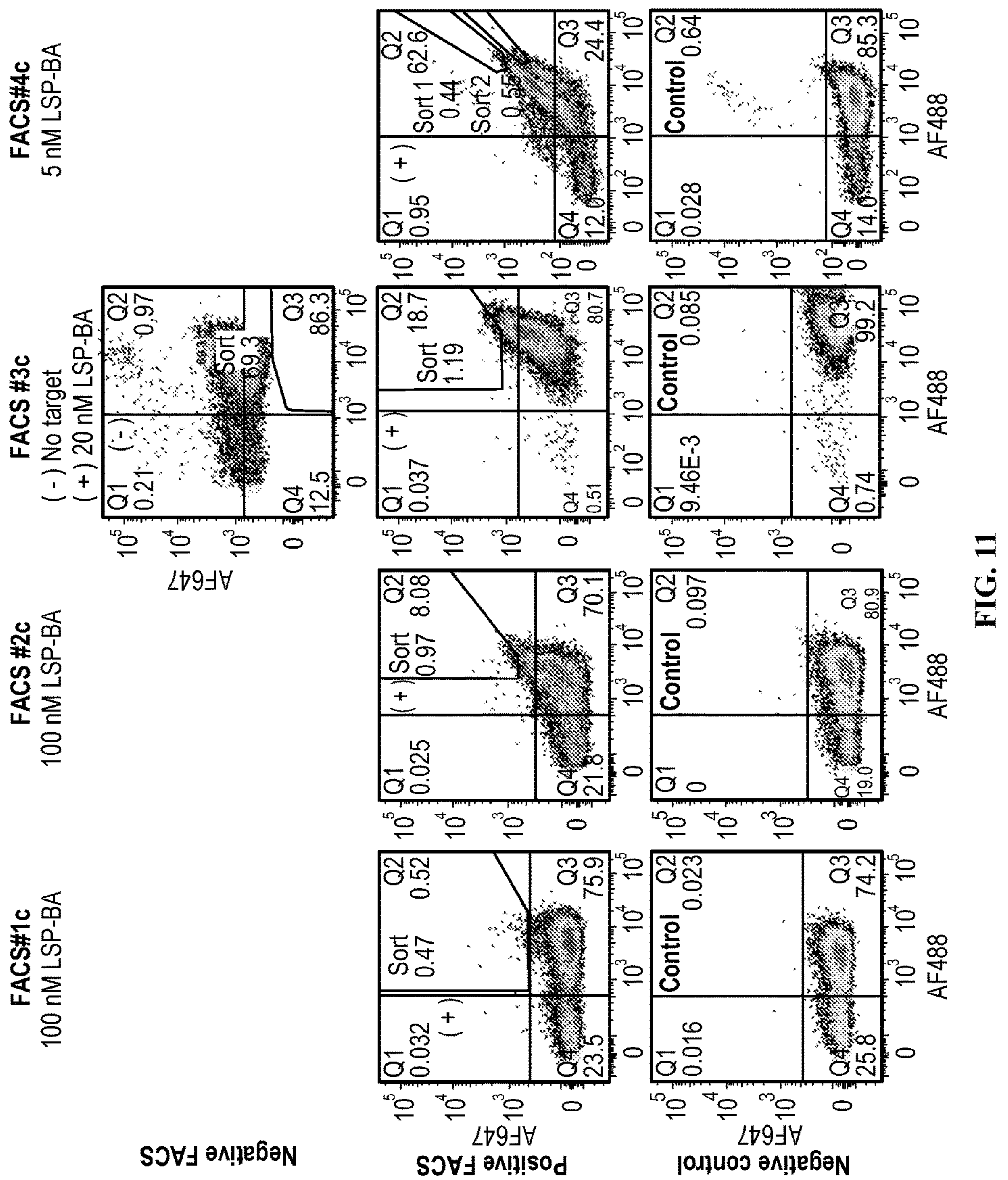
FIG. 11. FACS dot plots for the FACS selections against LSP-BA, originating from the MBS population screened using LSP-BA (FACS "c"). Negative sorts (top row) were conducted prior to positive sorts (middle row) for FACS #3c. Bottom row depicts the negative controls (samples incubated without LSP-BA) for the positive FACS sub-populations. Concentration of LSP-BA used are listed above the plots, with a reduction in concentration from 100 nM to 5 nM for increased stringency. Numbers indicate the percentage of the population in each quadrant. Gates drawn indicate the gates used for sorting.

In efforts to expand the diversity of identified rcSso7d variants against LSP, another round of selections was conducted, starting from the naïve rcSso7d library and using LSP-BA for both MBS and FACS (FACS "c"; FIG. 2 and FIG. 11). A round of negative selection was conducted prior to FACS #3c to remove nonspecific binding variants against SA AF647. Additionally, in efforts to identify full length variants of LSP, the C-terminal c-Myc tag was used on the yeast-displayed rcSso7d variants to label for expression in FACS #3c and #4c, instead of the N-terminal HA tag. After FACS #4c, the sub-library was sorted into two sub-populations based on the appearance of two potentially monoclonal populations. After sequencing a subset of the two sub-populations, two additional unique rcSso7d sequences were identified (clones 7 and 8; TABLE 1), confirming that the sub-populations were monoclonal. These clones were full length, as expected based on the use of the C-terminal c-Myc tag for labeling expression.

From the three selection schemes, a total of eight unique rcSso7d clones were identified. These clones were analyzed for specific binding against LSP in a yeast-surface display format (FIGS. 3A-3B). All clones except clone 8 demonstrated target-specific binding to LSP. rcSso7d.LSP.8 showed off-target binding to the labeling reagents (mouse anti-His antibody and goat anti-mouse AF647); therefore, this variant was no longer pursued in subsequent studies.

Example 2: Analyses of rcSso7d Variant Stability

Figure 4B:
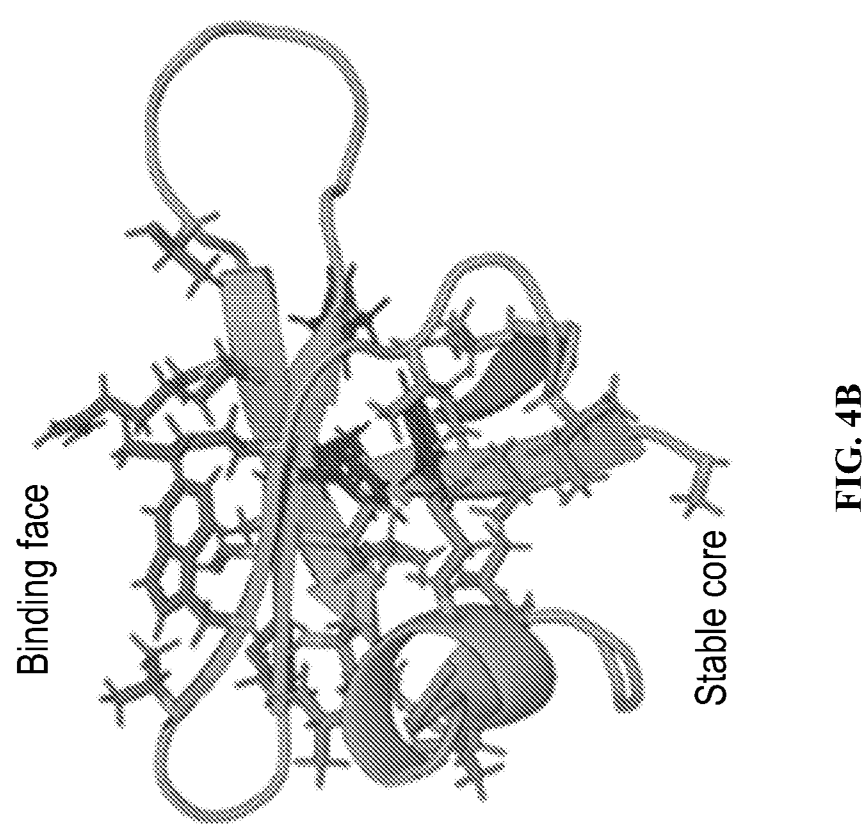

As previously mentioned, four of the identified clones resulted in truncated sequences. Studies have demonstrated that four amino acid residues in the rcSso7d hydrophobic core are vital to the stability of the protein, forming a "herring bone" structure: F5, Y7, F31, and Y33 (24) (FIGS. 4A-4B). The four truncated rcSso7d variants (clones 1, 2, 4, and 6) contained an early stop codon mutation that led to the absence of the fourth herring bone amino acid (Y33L).

Figure 4C:
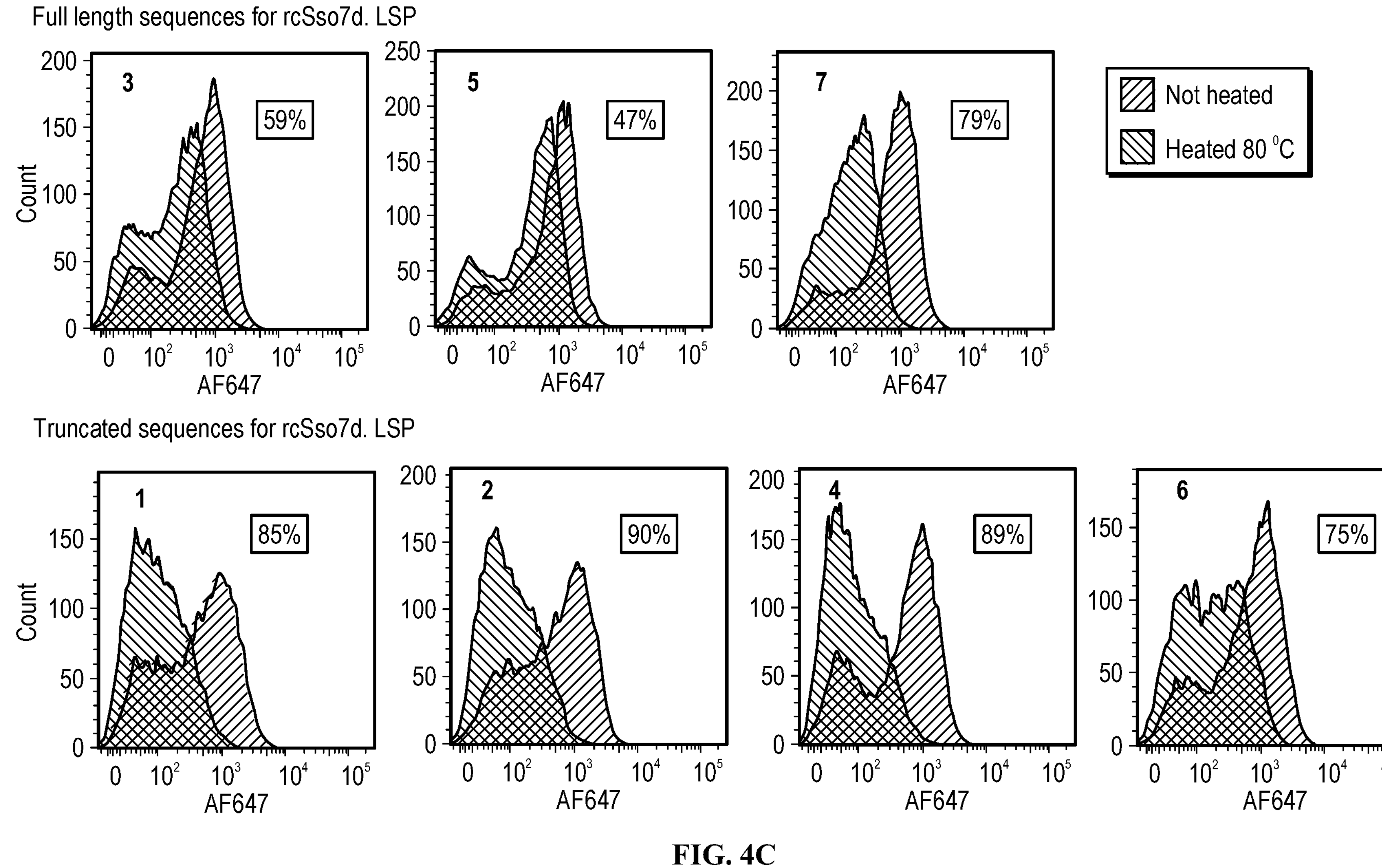

To investigate whether this early truncation affects the thermal stability of the rcSso7d clones, heat stability studies were conducted (25, 26). The rcSso7d-displaying clonal yeast cells were heat treated for 10 minutes at 80° C. and then assessed for target-binding activity loss. Two of the three full length rcSso7d variants (clones 3 and 5) maintained activity after heat treatment (FIG. 4C). Clone 7 had moderate activity loss, which may be due to the additional amino acid (FIG. 4A) disrupting the hydrophobic core packing or the herring bone structure of the four key amino acids. On the other hand, truncating the rcSso7d sequence appeared to have significant detrimental effects on the thermal stability of the scaffold, with nearly all activity loss for almost all truncated clones (FIG. 4C). These results demonstrate the importance of full length sequences in maintaining the hyperthermostability of the rcSso7d scaffold.

Based on the thermal stability studies and on preliminary data of these clones against whole *Listeria* cells (data not shown), rcSso7d.LSP.3 was chosen for future tests.

Example 3: rcSso7d.LSP Demonstrates Specific Binding to Live, Whole Cell *L. monocytogenes*

The rcSso7d.LSP.3 variant was cloned from the yeast-surface display vector into a bacterial expression vector for soluble protein expression. Soluble rcSso7d.LSP.3 was expressed in *E. coli* and purified for testing (FIGS. 6A-6C).

Figure 5A:
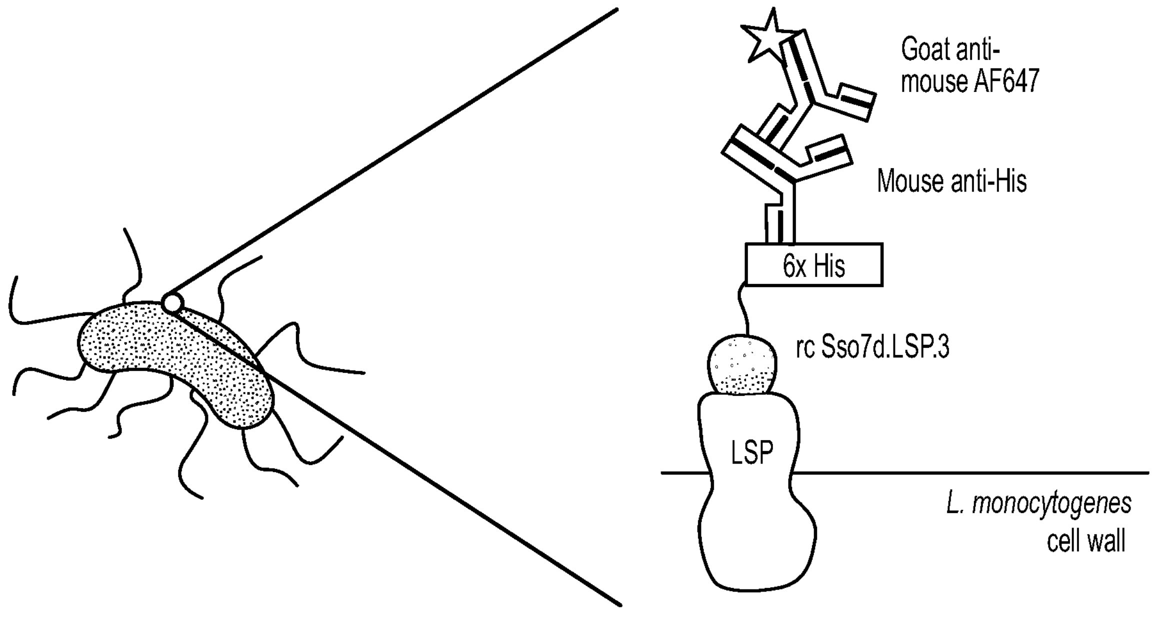

Although the identified rcSso7d.LSP clones demonstrated specific binding to LSP, further studies were performed to develop affinity reagents that can specifically bind to live, whole cell *L. monocytogenes*. Therefore, the soluble rcSso7d.LSP.3 variant was used to label whole *Listeria* cells (FIG. 5A). The buffer used for incubating the rcSso7d with the *Listeria* cells was first optimized. Stronger binding signal was detected in a lower pH buffer (40 mM sodium acetate, pH 5.5) than in a neutral buffer (PBS, pH 7.4) (FIGS. 5B-5C). It was hypothesized that the difference in binding signal is attributed to charge effects. The theoretical isoelectric point of the rcSso7d.LSP.3 protein is 6.2, therefore, in the sodium acetate buffer (pH 5.5), the rcSso7d protein has a net positive charge, while in PBS (pH 7.4), the rcSso7d has a net negative charge. Thus, the net positive charge of rcSso7d in sodium acetate may facilitate interactions with the negatively charged *Listeria* cells.

To further demonstrate that this binding signal to whole cell *Listeria* is target specific, the rcSso7d.LSP.3 clone was challenged in sodium acetate against live, whole cell *Bacillus subtilis* as a model non-pathogenic, Gram-positive bacterium (FIG. 5D). The rcSso7d.LSP.3 variant depicted no binding to *B. subtilis*, validating that the binding signal shown against *L. monocytogenes* is not from non-specific interactions against generic bacterial surface epitopes.

In summary, multiple rcSso7d-based affinity reagents have been identified against a *Listeria monocytogenes* surface protein, LMOf2365_0639, using a yeast-surface display library. A few rcSso7d variants with early truncation sequences were identified that led to reduced thermal stability, possibly due to a disruption of the highly stable core. Nonetheless, seven out of the eight identified rcSso7d variants—including the truncated variants—demonstrated target-specific binding to the *Listeria* surface protein. rcSso7d.LSP.3 was selected for testing against live, whole cell *L. monocytogenes* and depicted strong binding to the whole cells when they were incubated in a buffer at pH 5.5—below the isoelectric point of the rcSso7d protein. Furthermore, the rcSso7d did not depict binding to a non-target bacterium, *Bacillus subtilis*. These results demonstrate that this rcSso7d clone can be used as an affinity reagent for use in detecting live, whole cell *L. monocytogenes*.

Example 4: Materials and Methods for Examples 1-3

Commercial reagents: Primary labeling reagents and dilutions (bold) used for selection were: chicken anti-HA (AHA; 1:1000) and chicken anti-cMyc (CMYC; 1:1000) from Exalpha Biologicals, and mouse anti-6×-His (clone MA1-21315, HIS.H8; 1:1000) from Thermo Fisher Scientific. Secondary detection reagents were goat anti-mouse AlexaFluor (AF) 647 (A-21235; 1:1000), goat anti-chicken AF488 (A-11039; 1:1000), and streptavidin AF647 (S-21374; 1:1000) from Thermo Fisher Scientific. Magnetic bead selections were conducted using HisPur NiNTA Magnetic Beads (88831) and Dynabeads Biotin Binder (11047) from Thermo Fisher Scientific. Brain Heart Infusion (BHI) broth component Bacto Brain Heart Infusion (BD 237500) and the Enriched Nutrient broth components Bacto Heart Infusion Broth (BD 238400), Difco Nutrient Broth (BD 234000), and Bacto Yeast Extract (BD 212750)) were purchased from VWR.

A pET28b(+) plasmid containing the LMOf2365_0639 (*Listeria monocytogenes* surface protein, LSP) sequence (strain 3D7; VG40303-G) with an N-terminal 6×-histidine tag was codon-optimized and synthesized from GeneWiz.

*Listeria monocytogenes* (Murray et al.) Pirie (ATCC® 43256™) CDC F2380 strain (isolated from Mexican-style cheese) and *Bacillus subtilis* (Ehrenberg) Cohn (ATCC® 27370™) 168 M strain were obtained from ATCC.

Production of recombinant biomarkers: The plasmid construct for the N-terminal 6×-histidine tag variant of LSP (His-LSP) was synthesized in pET28b(+) from GeneWiz. The plasmid construct for the C-terminal biotin acceptor (BA) variant of LSP (LSP-BA)—with N-terminal His tag for purification—was developed following protocols as described previously (17-19, 21). Briefly, polymerase chain reaction (PCR) was conducted on LSP using the pET28b (+)-His-LSP backbone with the primers listed in TABLE 2 and an annealing temperature of 62° C. The plasmid backbone pET28b(+)-Sso.TB-Link-BA from Sung, et al (19) was used to obtain a pET28b(+) vector with a C-terminal BA sequence. A double digest on the PCR product and this backbone was conducted using NdeI and BamHI restriction enzymes before running a ligation reaction. The ligation products were purified using the DNA Clean and Concentrator Kit (Zymo Research) before transformation into DH5a *E. coli* via electroporation.

TABLE 2

Oligonucleotide sequences of primers used to clone LSP-BA.

| SEQ ID NOs | Oligo Name | DNA Sequence (NdeI and BamHI, restriction sites) |
|---|---|---|
| 20 | LSP-BA-NdeI-for | 5'-CTGG**CATATG**GTTAATATCCCGGACCCGGTTCTGAAGAGC-3' |
| 21 | LSP-BA-BamHI-rev | 5'-TATTA*GGATCC*CGTGTTTGGGAGGGCGGCGTTA-3' |

His-LSP and LSP-BA were expressed and purified as described previously (17-19, 21). All biomarker constructs were expressed in BL21(DE3) *E. coli* and induced with 0.5 mM isopropyl β-D-1-thiogalactopyranoside (IPTG). LSP-BA was supplemented with free biotin during expression by adding 0.1 mM D-biotin in 10 mM bicine buffer. After overnight expression at 20° C., the cells were pelleted, lysed via sonication, and purified using immobilized metal affinity chromatography (IMAC) with HisTrap FF crude columns (GE Healthcare). After purification, the proteins were then buffer exchanged into 1×PBS using Amicon Ultra Centrifugal Filters.

All purified proteins were quantified using a bicinchoninic acid (BCA) assay (Thermo Fisher Scientific) and run on a sodium dodecyl sulfate polyacrylamide gel electrophoresis (SDS-PAGE), as previously described (19).

Selections against LSP: Selections were conducted using yeast-surface display as previously described (16, 21, 23, 27). Briefly, *Saccharomyces cerevisiae* EBY100 containing the pCTCON2-rcSso7d combinatorial library (naïve diversity: $1.4\times10^9$ clones) (16) were cultured in SDCAA media (citrate form) at 30° C. overnight. After passaging the cells, the yeast culture was induced once the $OD_{600}$ approached 4 by passaging the cells into SGCAA (supplemented with 2 g/L dextrose) at an $OD_{600}$ of 1. Yeast cells were induced for 24 hours at 20° C. At least 20-fold of the library diversity was used in each sorting step. Induced cells were prepared by taking the appropriate number of cells and washing them in PBSF (1×PBS with 0.1% bovine serum albumin, sterile filtered) twice. Yeast populations were centrifuged at 2,000×g for three minutes to pellet the cells gently.

Magnetic bead sorting (MBS) was conducted as previously described (17, 21). For selections against His-LSP, HisPur NiNTA magnetic beads were used to immobilize His-LSP, using at least 100 pmoles of His-LSP per 1 μL of beads, incubated for at least 2 hours at 4° C. At least 2 μL of coated NiNTA beads were used for at most $1.4\times10^9$ yeast cells. For selections against LSP-BA, Dynabeads biotin binder magnetic beads were used to immobilize LSP-BA, using 500 pmoles of LSP-BA per 10 μL of beads, incubated for at least 2 hours at 4° C. on a rotary mixer. 10 μL of biotin binder beads were used for at most $1.4\times10^9$ yeast cells. For each LSP variant, selections were conducted with two rounds of positive sorts against the coated beads by incubating the cells with the coated beads for at least 2 hours at 4° C. on a rotary mixer. Cells that were bound to the beads were washed at least twice. One round of negative sort was conducted immediately prior to the second positive sort using uncoated beads by incubating the cells with the uncoated beads for at least 2 hours at 4° C. on a rotary mixer. Cells that were unbound were collected and used for a positive sort. Yeast cells were outgrown in SDCAA media between each round of selection.

Fluorescence-activated cell sorting (FACS) was conducted as previously described (17, 21). Three different sets of FACS selections were conducted: 1) FACS "a" using the post-MBS library enriched against His-LSP and further enriching against His-LSP, 2) FACS "b" using the post-MBS library enriched against His-LSP and further enriching against LSP-BA, and 3) FACS "c" using the post-MBS library enriched against LSP-BA and further enriching against LSP-BA. Four rounds of FACS were conducted for each sort, decreasing the concentration of LSP used for subsequent sorts for increased selective pressure against higher affinity clones. To label LSP binding, mouse anti-His/goat-anti-mouse AF647 was used for His-LSP, and SA AF647 was used for LSP-BA. Surface expression of the rcSso7d was labeled using chicken anti-HA/goat anti-chicken AF488 for all sorts, except for FACS #3c and #4c, which used chicken anti-cMyc/goat anti-chicken AF488 to label for full length rcSso7d expression since the HA tag is on the N-terminus of surface-displayed rcSso7d and the c-Myc tag is on the C-terminus of the surface-displayed rcSso7d. Negative selections in FACS (21) were conducted in FACS #2a, #3a, #4a, #2b, #3b, #4b, and #3c by labeling the yeast sub-libraries with the labeling reagents in the absence of LSP and collecting the population that did not display positive binding signal. These collected cells were immediately relabeled for positive sorts.

For all flow cytometry preparations, primary incubation steps were conducted at room temperature for 20-30 minutes, except when the biomarker concentration was low enough to require longer incubation times to reach equilibrium. Secondary incubation steps were conducted at 4° C. for 15-20 minutes. After each labeling step, cells were washed with 1 mL of PBSF. Sorting was conducted on a BD FACS Aria using the FACS Diva software, detecting the fluorescence of AF647 (excitation 640 nm, emission 670/30 nm) and AF488 (excitation 488 nm, emission 582/15 nm). Data was analyzed using FlowJo software.

rcSso7d clonal analysis: After FACS, the enriched yeast sub-libraries were sequenced to determine the diversity, as described previously (17, 21). Briefly, the sub-libraries were miniprepped using the ZymoPrep Yeast Miniprep II kit, and the plasmid products were transformed into DH5a *E. coli*. Ten to twenty bacterial colonies were picked and sent off for sequencing via GeneWiz (TABLE 3). The pCTCON2 plasmids for unique clones were transformed back into *S. cerevisiae* EBY100 using the Frozen-EZ Yeast Transformation II Kit (Zymo Research).

TABLE 3

Number of occurrences of each identified unique clone after sequencing the post-FACS #4a, post-FACS #4b, and the two post-FACS #4c (i and ii) sub-library populations.

| | Number of occurrences after sequencing | | | |
|---|---|---|---|---|
| | FACS #4a | FACS #4b | FACS #4c, i | FACS #4c, ii |
| Clone 1 | 25 | 14 | 0 | 0 |
| Clone 2 | 1 | 0 | 0 | 0 |
| Clone 3 | 1 | 0 | 0 | 0 |

TABLE 3-continued

Number of occurrences of each identified unique clone after sequencing the post-FACS #4a, post-FACS #4b, and the two post-FACS #4c (i and ii) sub-library populations.

| | | | Number of occurrences after sequencing | |
|---|---|---|---|---|
| | FACS #4a | FACS #4b | FACS #4c, i | FACS #4c, ii |
| Clone 4 | 2 | 0 | 0 | 0 |
| Clone 5 | 1 | 0 | 0 | 0 |
| Clone 6 | 0 | 1 | 0 | 0 |
| Clone 7 | 0 | 0 | 10 | 0 |
| Clone 8 | 0 | 0 | 0 | 10 |

Unique clones were analyzed using flow cytometry, following a similar labeling procedure as outlined above for sorting. Each clone was challenged with 20 nM of His-LSP, followed by mouse anti-His antibody and goat anti-mouse AF647. Surface expression levels were labeled with chicken anti-HA and goat anti-chicken AF488. Results were analyzed on FlowJo software.

Heat stability studies: Thermal stability studies were conducted on the identified rcSso7d clones in the yeast-surface display format, following a procedure described in Traxlmayr, et al (26). In this process, each clonal yeast was cultured and induced as described previously. $5\times10^6$ cells from each rcSso7d-displaying yeast culture were washed with PBSF and resuspended in 170 µL of PBSF (for an $OD_{600}$ of 3). The samples were heated in a thermocycler for 10 minutes at 80° C. before placing the samples on ice for 5 minutes. The heat-treated cells and non-heat-treated cells (for a positive control) were labeled with His-LSP, mouse anti-His antibody, and goat anti-mouse AF647 for binding and chicken anti-HA and goat anti-chicken AF488 for expression, following the same protocol as outlined above. The labeled samples were analyzed on flow cytometry. The geometric mean fluorescence signal of AF647 for each sample was calculated using FlowJo software, analyzing only the cells that showed positive expression. The percentage reduction in target-binding activity was calculated by dividing the geometric mean signal after heat-treatment by the signal without heat-treatment.

Production of rcSso7d clones: rcSso7d.LSP.3 was cloned as previously described (17, 20) and detailed above, using the primers listed in TABLE 4, an annealing temperature of 59° C., NdeI and XhoI restriction enzymes, and any pET28b (+) backbone. The protein was produced following the same protocol as detailed in the above section.

TABLE 4

Oligonucleotide sequences of primers used to clone rcSso7d.LSP.3.

| SEQ ID NO: | Oligo Name | DNA Sequence (NdeI and XhoI, restriction sites) |
|---|---|---|
| 22 | rcSso7d-for | 5'-AGGCAGTCT**CATATG**TGTGCAACCG TGAAATTCAC-3' |
| 23 | rcSso7d-rev | 5'-ACCCCT*CTCGAG*TTATTGCTTTTCC AGCA-3' |

Testing against whole bacterial cells: Brain Heart Infusion (BHI) broth was prepared using 37 g/L of Bacto Brain Heart Infusion in deionized water. Enriched Nutrient (EN) broth was prepared using 12.5 g/L of Bacto Heart Infusion Broth, 5.4 g/L of Difco Nutrient Broth, and 2.5 g/L of Bacto Yeast Extract in deionized water. Broths were autoclaved prior to use. *Listeria monocytogenes* was cultured overnight in BHI broth and *Bacillus subtilis* was cultured overnight in EN broth, both at 30° C. in a shaking incubator.

Approximately $3\times10^8$ *L. monocytogenes* cells and $1\times10^8$ *B. subtilis* cells were used for each sample. Cells were pelleted at 4,000×g for 5 minutes and washed twice with 1 mL of PBSF. Primary incubations occurred with rcSso7d.LSP.3 diluted in either PBSF or 40 mM sodium acetate (pH 5.5) buffer, on a rotary mixer for at least 3 hours at room temperature. After washing the cells in PBSF, they were resuspended in the secondary incubation solution containing mouse anti-His antibody in PBSF (to target the His tag on the rcSso7d.LSP.3 protein) and incubated for 20-30 minutes at room temperature on a rotary mixer. After another set of washes in PBSF, the cells were resuspended in the tertiary incubation solution containing goat anti-mouse AF647 in PBSF and incubated for 15-20 minutes on ice. Samples were washed in PBSF one last time before being processed using flow cytometry. Negative controls followed the same protocol, except with incubations in just PBSF for the secondary incubation step, without mouse anti-His antibody. Results were analyzed using FlowJo software.

Additional Sequences

His-LSP
Nucleic acid sequence (SEQ ID NO: 24):
ATGGGCAGCAGCCATCATCATCATCATCACAGCAGCGGCCTGGTGCCGCGCGGC
AGCCATATGGAATTCGTTAATATCCCGGACCCGGTTCTGAAGAGCTACCTCAATG
GTCTGCTGGGCCAAAGCAGCACGAGCGATATCACCGAAGCGCAGATGGATACCA
TCACGAATGTGACCATCAGCAACAGCAGCCTCACCGATCTGACCGGCCTCGACTA
CGCCCACAATCTGACGATTCTCCACCTCAGTAACACGGGTGTGACCGACTACGCG
CTCGTGGCCAAGATTCCGAGTCTGACGAATCTGAGCATTGCGGGTGATAACCTCA
CCAATGACAGTCTGCCGGATCTGAACAACCTCAGCAACATCACGAACCTCAATCT
GAGCCCGGGCAAGCTGGATAACAACGCGCTGACGAAGTTCAATAAAATGAGCAA
GCTGAGCTATCTGAATCTGGACAGCAACCCGAGCATCACGAACATCATGCCGCTC
AAAAGCATCCCGAATCTGGCGACGCTGTTCGTGCAGTTCTGCGGCATTAACGACT
TCCGCGGCATCGATACGTTCCCGAAGCTGGTGAGTCTGAGTGCGTATGGTCAGAA
CGTGGGCCGCACGGTGCTGATCAACAGCAGCATTAAGAGCAGTGCGCTGAACTT
CGATGAGGCCAACCAGACGATCTTCGTGCCATTTACCCTCATGACCGAACGCGGC
GTGAACTTCGACGGTTACCTCTTCCCATTCACCACCAATACCAGCAGCGCCAGTA
CGTACTTCACCCTCAACGAGACCAAGATTGACGGTAGTCGTCTCACGATCGATGA
CAAGGGTATCACGGTGAGCGGTATCACCAAAAGCTACTTCGACACGATTACGAA
GATGGAGTATAACGCCCTCTACAACAACCCGGCCGGTAGTTATCAGACGCCGCC
GAACTTCAACAACTACAGCGTTAGTGGCGGCAGCTACGATCACTACTTCGACATC
GACCACAGCCTCACCATTACGAACGACAGCGCCATCAGCTACGGTGAGCAGACG -continued

| Additional Sequences |
| --- |

ACCGTGACGGAGGAGCAGTTTCTGAAGGATGTGCACGCGGAAACCGACGATGGC
ACCCCGGTTACCAGCGACTTCAACACGGTGGTGGATTTCAGCAAGCCGGGCGTGT
ACACCGTTACGCTGAATGCCGAAAATGCGGCCGGTCTCAAAGCGACGCCAACCC
AAGTTACGGTTACCATCCACGCCAAGCCGGTGATTACCGCGGACAAAAGCATCA
GCTACACCAAGGACAGTACGAAAACCGATCAGCAGTTTCTGCAAGATATTAGCG
CGAAGACCAGTGACGGCAGCAAGGTTACGAGTGACTTTGACAGCGTGGTTGACC
TCGCGAAGGTGGGCACGTATAAGGTGACGCTGAATGCGGTTAGCGCGGATGGTC
TGAACGCCGACCCAGTGATCGTGCTCGTGAATGTGGTGGAAGGCAATGAACCAC
CAACCCCACCAGCCCCGGGCCCAGATCCGACGCCAGATCCAACCCCGAACCCGA
ACAACCCGAACATCAATCCGAATCCGGACAACGGTCAGAGTGCGAACAGCGAGA
ACGCGAGCAATCCAAGCAACAGCGAAGTTAACGCCGCCCTCCCAAACACGTAA

Amino acid sequence (SEQ ID NO: 25):
MGSSHHHHHHSSGLVPRGSHMEFVNIPDPVLKSYLNGLLGQSSTSDITEAQMDTITN
VTISNSSLTDLTGLDYAHNLTILHLSNTGVTDYALVAKIPSLTNLSIAGDNLTNDSLPD
LNNLSNITNLNLSPGKLDNNALTKFNKMSKLSYLNLDSNPSITNIMPLKSIPNLATLFV
QFCGINDFRGIDTFPKLVSLSAYGQNVGRTVLINSSIKSSALNFDEANQTIFVPFTLMT
ERGVNFDGYLFPFTTNTSSASTYFTLNETKIDGSRLTIDDKGITVSGITKSYFDTITKME
YNALYNNPAGSYQTPPNFNNYSVSGGSYDHYFDIDHSLTITNDSAISYGEQTTVTEEQ
FLKDVHAETDDGTPVTSDFNTVVDFSKPGVYTVTLNAENAAGLKATPTQVTVTIHA
KPVITADKSISYTKDSTKTDQQFLQDISAKTSDGSKVTSDFDSVVDLAKVGTYKVTL
NAVSADGLNADPVIVLVNVVEGNEPPTPPAPGPDPTPDPTPNPNNPNINPNPDNGQSA
NSENASNPSNSEVNAALPNT LSP-BA
Nucleic acid sequence (SEQ ID NO: 26):
ATGGGCAGCAGCCATCATCATCATCATCACAGCAGCGGCCTGGTGCCGCGCGGC
AGCCATATGGTTAATATCCCGGACCCGGTTCTGAAGAGCTACCTCAATGGTCTGC
TGGGCCAAAGCAGCACGAGCGATATCACCGAAGCGCAGATGGATACCATCACGA
ATGTGACCATCAGCAACAGCAGCCTCACCGATCTGACCGGCCTCGACTACGCCCA
CAATCTGACGATTCTCCACCTCAGTAACACGGGTGTGACCGACTACGCGCTCGTG
GCCAAGATTCCGAGTCTGACGAATCTGAGCATTGCGGGTGATAACCTCACCAATG
ACAGTCTGCCGGATCTGAACAACCTCAGCAACATCACGAACCTCAATCTGAGCCC
GGGCAAGCTGGATAACAACGCGCTGACGAAGTTCAATAAAATGAGCAAGCTGAG
CTATCTGAATCTGGACAGCAACCCGAGCATCACGAACATCATGCCGCTCAAAAG
CATCCCGAATCTGGCGACGCTGTTCGTGCAGTTCTGCGGCATTAACGACTTCCGC
GGCATCGATACGTTCCCGAAGCTGGTGAGTCTGAGTGCGTATGGTCAGAACGTG
GGCCGCACGGTGCTGATCAACAGCAGCATTAAGAGCAGTGCGCTGAACTTCGAT
GAGGCCAACCAGACGATCTTCGTGCCATTTACCCTCATGACCGAACGCGGCGTGA
ACTTCGACGGTTACCTCTTCCCATTCACCACCAATACCAGCAGCGCCAGTACGTA
CTTCACCCTCAACGAGACCAAGATTGACGGTAGTCGTCTCACGATCGATGACAAG
GGTATCACGGTGAGCGGTATCACCAAAAGCTACTTCGACACGATTACGAAGATG
GAGTATAACGCCCTCTACAACAACCCGGCCGGTAGTTATCAGACGCCGCCGAAC
TTCAACAACTACAGCGTTAGTGGCGGCAGCTACGATCACTACTTCGACATCGACC
ACAGCCTCACCATTACGAACGACAGCGCCATCAGCTACGGTGAGCAGACGACCG
TGACGGAGGAGCAGTTTCTGAAGGATGTGCACGCGGAAACCGACGATGGCACCC
CGGTTACCAGCGACTTCAACACGGTGGTGGATTTCAGCAAGCCGGGCGTGTACA
CCGTTACGCTGAATGCCGAAAATGCGGCCGGTCTCAAAGCGACGCCAACCCAAG
TTACGGTTACCATCCACGCCAAGCCGGTGATTACCGCGGACAAAAGCATCAGCT
ACACCAAGGACAGTACGAAAACCGATCAGCAGTTTCTGCAAGATATTAGCGCGA
AGACCAGTGACGGCAGCAAGGTTACGAGTGACTTTGACAGCGTGGTTGACCTCG
CGAAGGTGGGCACGTATAAGGTGACGCTGAATGCGGTTAGCGCGGATGGTCTGA
ACGCCGACCCAGTGATCGTGCTCGTGAATGTGGTGGAAGGCAATGAACCACCAA
CCCCACCAGCCCCGGGCCCAGATCCGACGCCAGATCCAACCCCGAACCCGAACA
ACCCGAACATCAATCCGAATCCGGACAACGGTCAGAGTGCGAACAGCGAGAACG
CGAGCAATCCAAGCAACAGCGAAGTTAACGCCGCCCTCCCAAACACGGGATCCA
TGGCGGGCGGCCTGAACGATATTTTTGAAGCGCAGAAAATTGAATGGCATGAAT
AA Amino acid sequence (SEQ ID NO: 27):
MGSSHHHHHHSSGLVPRGSHMVNIPDPVLKSYLNGLLGQSSTSDITEAQMDTITNVT
ISNSSLTDLTGLDYAHNLTILHLSNTGVTDYALVAKIPSLTNLSIAGDNLTNDSLPDLN
NLSNITNLNLSPGKLDNNALTKFNKMSKLSYLNLDSNPSITNIMPLKSIPNLATLFVQF
CGINDFRGIDTFPKLVSLSAYGQNVGRTVLINSSIKSSALNFDEANQTIFVPFTLMTER
GVNFDGYLFPFTTNTSSASTYFTLNETKIDGSRLTIDDKGITVSGITKSYFDTITKMEY
NALYNNPAGSYQTPPNFNNYSVSGGSYDHYFDIDHSLTITNDSAISYGEQTTVTEEQF
LKDVHAETDDGTPVTSDFNTVVDFSKPGVYTVTLNAENAAGLKATPTQVTVTIHAK
PVITADKSISYTKDSTKTDQQFLQDISAKTSDGSKVTSDFDSVVDLAKVGTYKVTLN
AVSADGLNADPVIVLVNVVEGNEPPTPPAPGPDPTPDPTPNPNNPNINPNPDNGQSAN
SENASNPSNSEVNAALPNTGSM*AGGLNDIFEAQKIEWHE*

-continued

| Additional Sequences |
| --- |

```
rcSso7d.LSP.3
Nucleic acid sequence (SEQ ID NO: 28):
ATGGGCAGCAGCCATCATCATCATCATCACAGCAGCGGCCTGGTGCCGCGCGGC
AGCCATATGTGTGCAACCGTGAAATTCACATACCAAGGCGAAGAAAAACAGGTG
GATATTAGCAAAATCAAGAACGTGCATCGTCATGGCCAGAAAATTTACTTTATCT
ATGATGAAGGTGGTGGTGCCAAAGGTCATGGTAAAGTGAGCGAAAAAGATGCAC
CGAAAGAACTGCTGCAGATGCTGGAAAAGCAATAA

Amino acid sequence (SEQ ID NO: 29):
MGSSHHHHHHSSGLVPRGSHMCATVKFTYQGEEKQVDISKIKIAKRYGQIIDFSYDE
GGGARGWGIVSEKDAPKELLQMLEKQ
```

Example 5: Additional Binding Proteins

In Examples 1-4, binding proteins were engineered that are highly specific to *Listeria monocytogenes*. These binding proteins are directed at a target protein termed LSP, for *Listeria* Surface Protein. Several rcSso7d sequences that specifically bind the extracellular portion of LSP (e.g. rcSso7d.LSP1-rcSso7d.LSP8) are disclosed.

Figure 12:
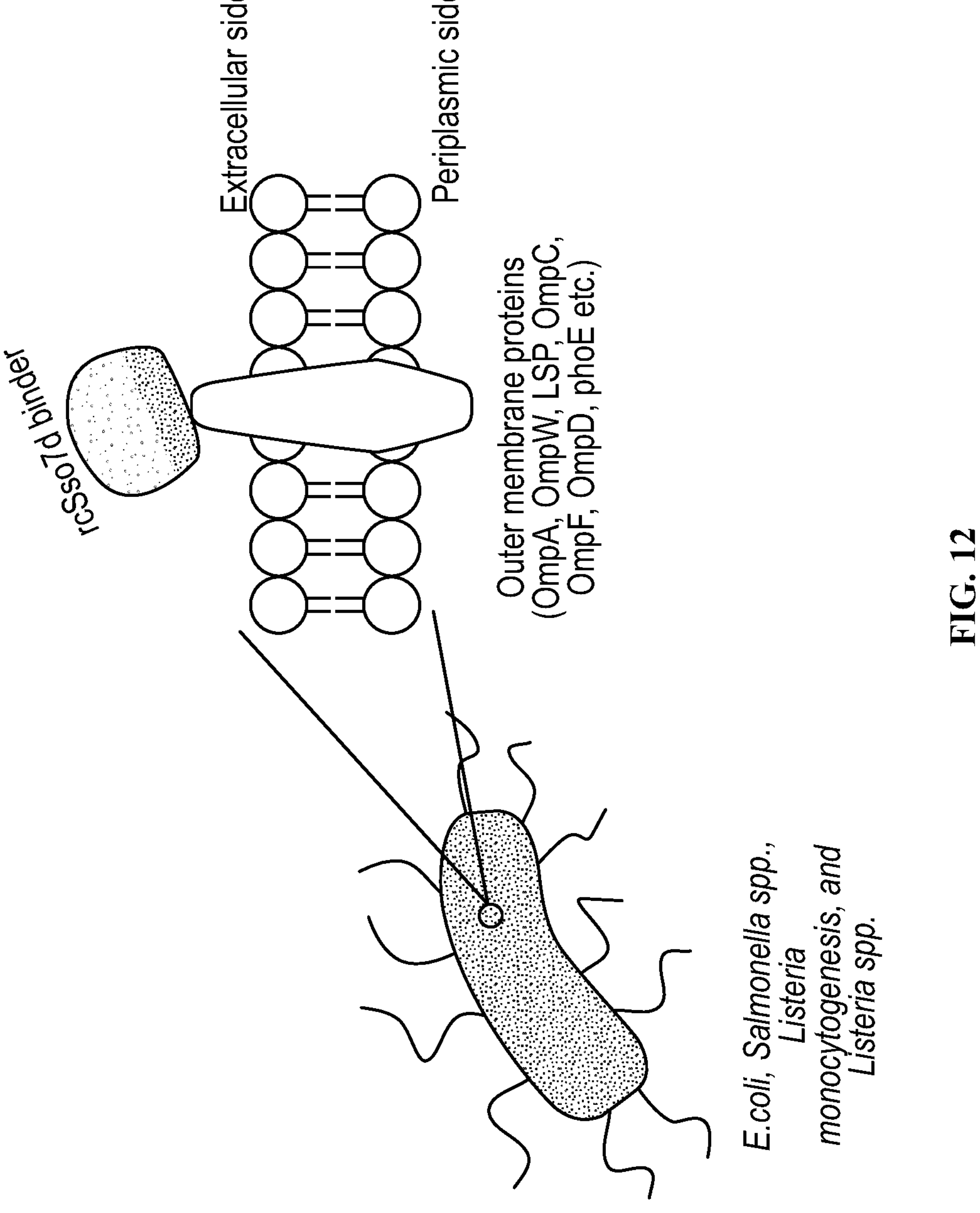
FIG. 12. Schematic of desired protein complex on the surface of *E. coli*, *Salmonella* ssp., *L. monocytogenes*, and *Listeria* spp. cells for rcSso7d binding. Exemplary target proteins include OmpA, OmpW, LSP, OmpC, OmpF, OmpD, and phoE.

This example demonstrates that the strategy described in Examples 1-4 is generalizable to additional bacterial species (FIG. 12). Using the same procedures described in Examples 1-4, additional binding proteins were engineered that target other bacterial proteins that are constituents of the extracellular portions of bacterial cell walls. These bacterial proteins include the outer membrane protein A, OmpA, and outer membrane protein W, OmpW, of *E. coli*, and outer membrane proteins of *Salmonella typhi* (termed herein Native Omp). The antigen called Native Omp is a combination of parts of the above mentioned outer membrane proteins as well as OmpC, OmpF, OmpD, and phoE.

The sequence of OmpA is conserved across many bacteria. For example, these proteins in *Salmonella* species and *E. coli* share a sequence identity of 93% (FIG. 13) (28). OmpA is an abundant protein; each cell expresses approximately 100,00 copies in its cell wall (29). OmpA and some other outer membrane proteins (30) consist of multiple domains, including domains that contain extracellular loops, those that span the cell membranes, and domains that are soluble (rather than membrane associated) in the periplasm (FIG. 14A) (29).

Figure 14B:
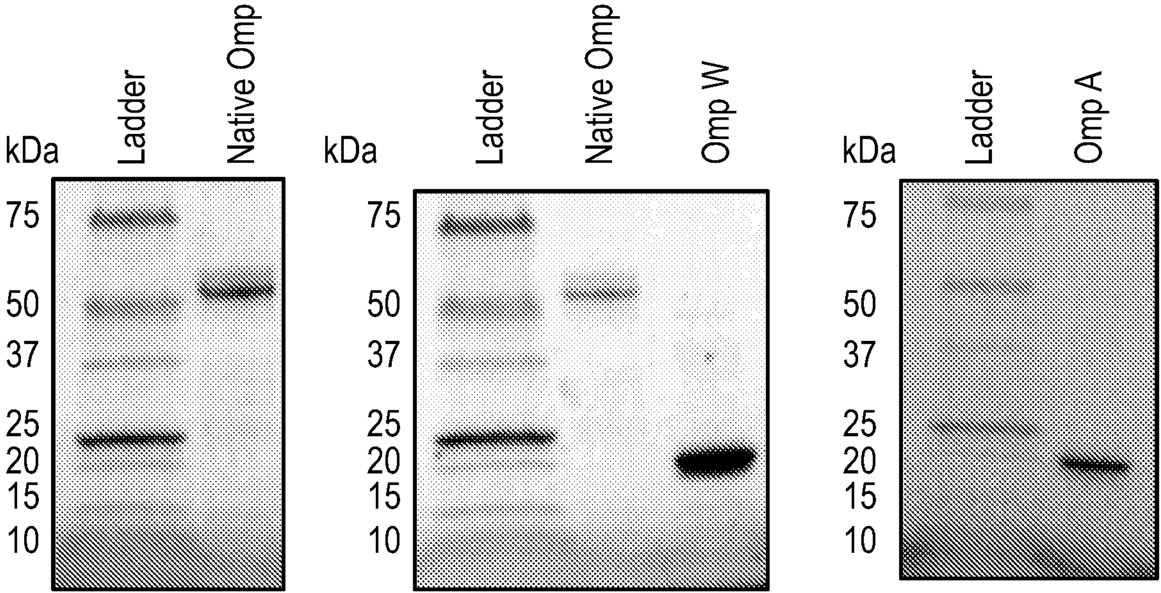

To target bacteria generally, we produced a recombinant version of the N-terminal domain of OmpA, because the N-terminal domain contains the extracellular loops that are accessible for binding (29). To target *E. coli* more specifically, we produced a recombinant version of OmpW, as the sequence of this membrane protein is much less conserved across different bacteria (31). To show that the approach applies to *Salmonella*, we used a recombinant chimeric antigen that contains epitopes from many outer membrane proteins of *Salmonella typhi* (32). This antigen is appealing as it has been validated as producing protective immune responses (33-34). FIG. 14B shows SDS PAGE gels of the antigens that were used in selection of rcSso7d variants that bind these bacterial outer membrane proteins.

Figures 15, 16A:
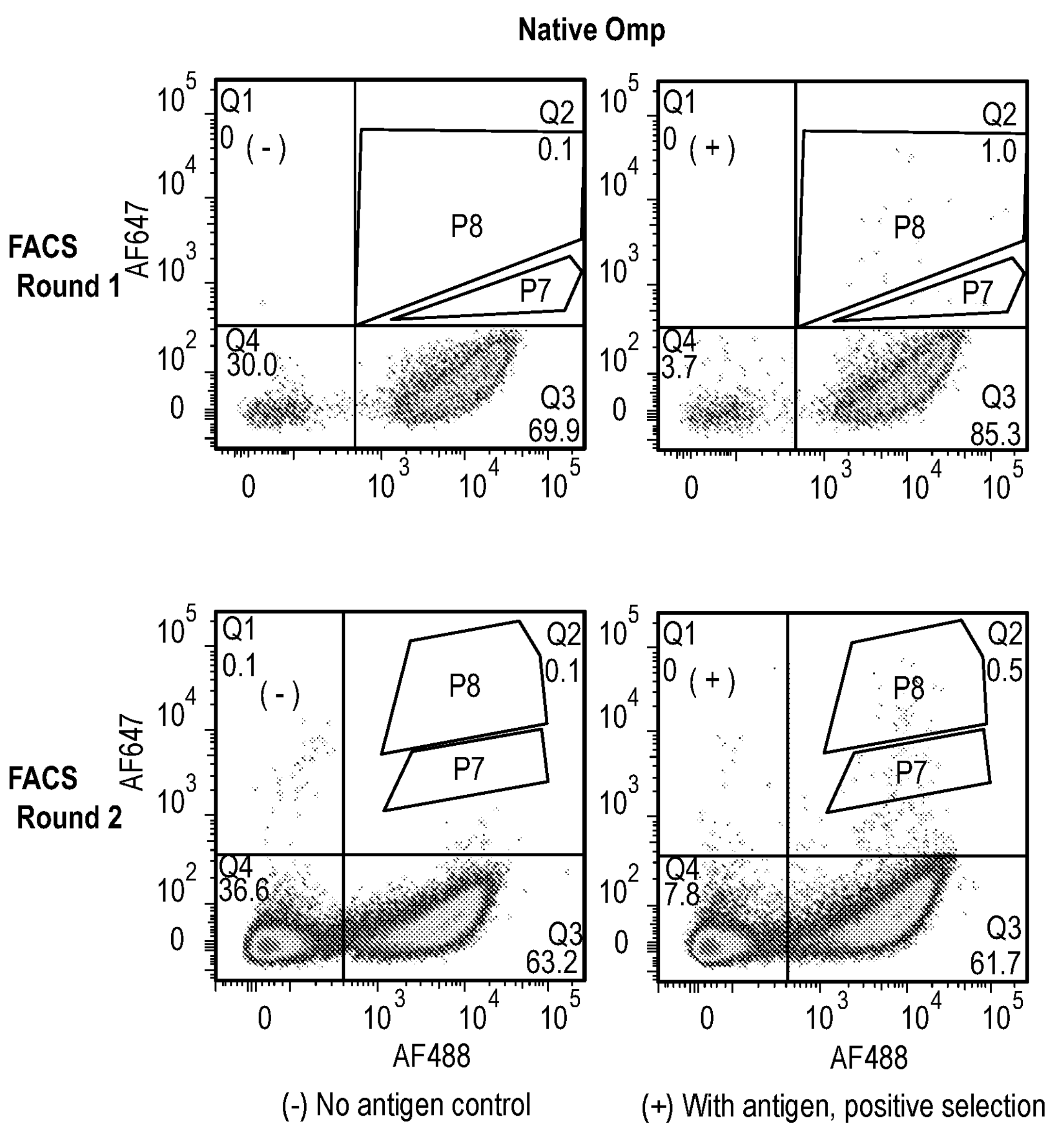
Figure 16B:
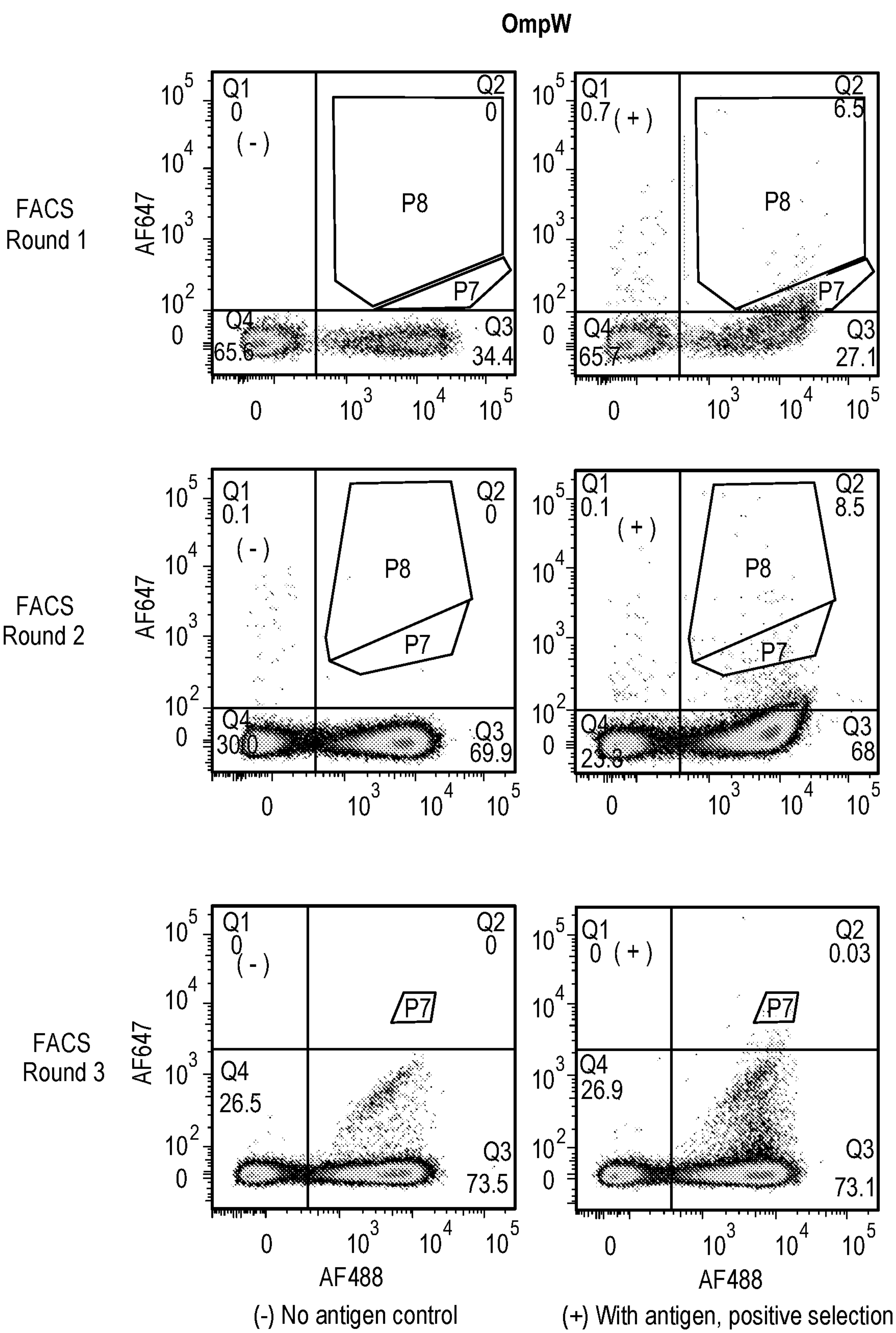

Magnetic beads that bind proteins containing a hexahistidine tag (OmpW, Native Omp) or a biotin tag (OmpW) were coated with an excess of the antigen sufficient to saturate all binding sites on the magnetic bead, according to binding capacities reported by the manufacturers of the magnetic beads. The naive library of $1.4\times10^9$ rcSso7d variants, each displayed on the surface of a different yeast cell, was sorted using the antigen-coated magnetic beads until the library diversity was reduced to $1.4\times10^7$, the upper limit that can reasonably be sorted according to quantitative binding activity using FACS (FIG. 15). Multiple rounds of FACS were performed for each antigen (*Salmonella typhi* Native Omp, *E. coli* OmpW, *E. coli* OmpA). FIGS. 16A-16C shows negative control FACS plots (yeast display library of rcSso7d variants and all staining reagents, but no antigen) and corresponding plots for the same libraries and staining reagents, plus antigen. The shapes indicated with P7 and P8 indicate the populations of cells that were retained in each round. In the negative control plots (−), no or few cells exhibited signals in these areas. When antigen was added (+), a number of rare clones exhibited signals in the indicated regions of the double positive quadrant of the FACS plot. The subpopulations of antigen-binders in each round were selected, expanded in culture, and eventually sequenced to determine the identity of the clones that are specific to each antigen (FIGS. 17-19).

REFERENCES

1. Scallan, E.; Hoekstra, R. M.; Angulo, F. J.; Tauxe, R. V.; Widdowson, M.-A.; Roy, S. L.; Jones, J. L.; Griffin, P. M. Foodborne Illness Acquired in the United States-Major Pathogens. Emerg. Infect. Dis. 2011, 17 (1), 7-15.
2. Välimaa, A.-L.; Tilsala-Timisjärvi, A.; Virtanen, E. Rapid Detection and Identification Methods for *Listeria monocytogenes* in the Food Chain—A Review. Food Control 2015, 55, 103-114.
3. Byrd-Bredbenner, C.; Berning, J.; Martin-Biggers, J.; Quick, V. Food Safety in Home Kitchens: A Synthesis of the Literature. Int. J. Environ. Res. Public Health 2013, 10 (9), 4060-4085.
4. Shamloo, E.; Hosseini, H.; Abdi Moghadam, Z.; Halberg Larsen, M.; Haslberger, A.; Alebouyeh, M. Importance of *Listeria monocytogenes* in Food Safety: A Review of Its Prevalence, Detection, and Antibiotic Resistance. Iran. J. Vet. Res. 2019, 20 (4), 241-254.
5. Vázquez-Boland, J. A.; Kuhn, M.; Berche, P.; Chakraborty, T.; Domínguez-Bernal, G.; Goebel, W.; Gonzalez-Zorn, B.; Wehland, J.; Kreft, J. *Listeria* Pathogenesis and Molecular Virulence Determinants. Clin. Microbiol. Rev. 2001, 14 (3), 584-640.
6. FDA. Testing Methodology for *Listeria* Species or *L. monocytogenes* in Environmental Samples; College Park, Maryland, 2015.
7. Gasanov, U.; Hughes, D.; Hansbro, P. M. Methods for the Isolation and Identification of *Listeria* Spp. and *Listeria monocytogenes*: A Review. FEMS Microbiol. Rev. 2005, 29 (5), 851-875.

8. Hameed, S.; Xie, L.; Ying, Y. Conventional and Emerging Detection Techniques for Pathogenic Baterica in Food Science: A Review. Trends Food Sci. Technol. 2018, 81, 61-73.

9. Oravcová, K.; Trnčíková, T.; Kuchta, T.; Kaclíková, E. Limitation in the Detection of *Listeria monocytogenes* in Food in the Presence of Competing *Listeria Innocua*. J. Appl. Microbiol. 2008, 104 (2), 429-437.

10. Binz, H. K.; Amstutz, P.; Plückthun, A. Engineering Novel Binding Proteins from Nonimmunoglobulin Domains. Nat. Biotechnol. 2005, 23 (10), 1257-1268.

11. Banta, S.; Dooley, K.; Shur, O. Replacing Antibodies: Engineering New Binding Proteins. Annu. Rev. Biomed. Eng. 2013, 15, 93-113.

12. Ko Ferrigno, P. Non-Antibody Protein-Based Biosensors. Essays Biochem. 2016, 60, 19-25.

13. Morales, M. A.; Halpern, J. M. Guide to Selecting a Biorecognition Element for Biosensors. Bioconjug. Chem. 2018, 29 (10), 3231-3239.

14. Thaler, M.; Luppa, P. B. Highly Sensitive Immunodiagnostics at the Point of Care Employing Alternative Recognition Elements and Smartphones: Hype, Trend, or Revolution? Anal. Bioanal. Chem. 2019, 411 (29), 7623-7635.

15. Zhang, C. X. Y.; Brooks, B. W.; Huang, H.; Pagotto, F.; Lin, M. Identification of Surface Protein Biomarkers of *Listeria monocytogenes* Using Bioinformatics and Antibody-Based Protein Detection Tools. Appl. Environ. Microbiol. 2016, 82 (17), 5465-5467.

16. Traxlmayr, M. W.; Kiefer, J. D.; Srinivas, R. R.; Lobner, E.; Tisdale, A. W.; Mehta, N. K.; Yang, N. J.; Tidor, B.; Wittrup, K. D. Strong Enrichment of Aromatic Residues in Binding Sites from a Charge-Neutralized Hyperthermostable Sso7d Scaffold Library. J. Biol. Chem. 2016, 291 (43), 22496-22508.

17. Miller, E. A.; Traxlmayr, M. W.; Shen, J.; Sikes, H. D. Activity-Based Assessment of an Engineered Hyperthermophilic Protein as a Capture Agent in Paper-Based Diagnostic Tests. Mol. Syst. Des. Eng. 2016, 1, 377-381.

18. Miller, E. A.; Baniya, S.; Osorio, D.; Al Maalouf, Y. J.; Sikes, H. D. Paper-Based Diagnostics in the Antigen-Depletion Regime: High-Density Immobilization of RcSso7d-Cellulose-Binding Domain Fusion Proteins for Efficient Target Capture. Biosens. Bioelectron. 2018, 102, 456-463.

19. Sung, K.-J.; Miller, E. A.; Sikes, H. D. Engineering Hyperthermostable RcSso7d as Reporter Molecule for in Vitro Diagnostic Tests. Mol. Syst. Des. Eng. 2018, 3 (6), 877-882.

20. Zhang, Q.; Zeininger, L.; Sung, K.-J.; Miller, E. A.; Yoshinaga, K.; Sikes, H. D.; Swager, T. M. Emulsion Agglutination Assay for the Detection of Protein-Protein Interactions: An Optical Sensor for Zika Virus. ACS Sensors 2019, 4 (1), 180-184.

21. Miller, E. A.; Sung, K.-J.; Kongsuphol, P.; Baniya, S.; Aw-yong, H. Q.; Tay, V.; Tan, Y.; Kabir, F. M.; Pang-yeo, K.; Kaspriskie, I. G.; et al. Beyond Epitope Binning: Directed in Vitro Selection of Complementary Pairs of Binding Proteins. ACS Comb. Sci. 2020, 22 (1), 49-60.

22. Sung, K.-J.; Maalouf, Y. J. Al; Johns, Q. R.; Miller, E. A.; Sikes, H. D. Functional Comparison of Paper-Based Immunoassays Based on Antibodies and Engineered Binding Proteins. R. Soc. Chem. 2020.

23. Boder, E. T.; Wittrip, K. D. Yeast Surface Display for Screening Combinatorial Polypeptide Libraries. Nat. Biotechnol. 1997, 15, 553-557.

24. Catanzano, F.; Graziano, G.; Fusi, P.; Tortora, P.; Barone, G. Differential Scanning calorimetry Study of the Thermodynamic Stability of Some Mutants of Sso7d from *Sulfolobus Solfataricus*. Biochemistry 1998, 37 (29), 10493-10498.

25. Traxlmayr, M. W.; Obinger, C. Directed Evolution of Proteins for Increased Stability and Expression Using Yeast Display. Arch. Biochem. Biophys. 2012, 526 (2), 174-180.

26. Traxlmayr, M. W.; Faissner, M.; Stadlmayr, G.; Hasenhindl, C.; Antes, B.; Rüker, F.; Obinger, C. Directed Evolution of Stabilized IgG1-Fc Scaffolds by Application of Strong Heat Shock to Libraries Displayed on Yeast. Biochim. Biophys. Acta 2012, 1824 (4), 542-549.

27. Chao, G.; Lau, W. L.; Hackel, B. J.; Sazinsky, S. L.; Lippow, S. M.; Wittrup, K. D. Isolating and Engineering Human Antibodies Using Yeast Surface Display. Nat Protoc 2006, 1 (2), 755-768.

28. Freudl, R., and S. T. Cole. 1983. Cloning and molecular characterization of the ompA gene from *Salmonella typhimurium*. Eur. J. Biochem. 134:497-502.

29. Ortiz-Suarez M L, Samsudin F, Piggot T J, Bond P J, Khalid S. Full-Length OmpA: Structure, Function, and Membrane Interactions Predicted by Molecular Dynamics Simulations. Biophys J. 2016; 111(8):1692-1702. doi: 10.1016/j.bpj.2016.09.009

30. Singh S P, Williams Y U, Miller S, Nikaido H. The C-terminal domain of *Salmonella enterica* serovar *typhimurium* OmpA is an immunodominant antigen in mice but appears to be only partially exposed on the bacterial cell surface. Infect Immun. 2003; 71(7):3937-3946. doi: 10.1128/IAI.71.7.3937-3946.2003

31. Burgess N K, Dao T P, Stanley A M, Fleming K G. Beta-barrel proteins that reside in the *Escherichia coli* outer membrane in vivo demonstrate varied folding behavior in vitro. J Biol Chem. 2008; 283(39):26748-26758. doi:10.1074/jbc.M80275420

32. Native Antigen Company, Kidlington OX5 1LJ, United Kingdom

33. Isibasi, A., V. Ortiz, M. Vargas, J. Paniagua, C. Gonzalez, J. Moreno, and J. Kumate. 1988. Protection against *Salmonella typhi* infection in mice after immunization with outer membrane proteins isolated from *Salmonella typhi* 9,12,d,Vi. Infect. Immun. 56:2953-2959.

34. Liu Q, Liu Q, Yi J, et al. Outer membrane vesicles derived from *Salmonella Typhimurium* mutants with truncated LPS induce cross-protective immune responses against infection of *Salmonella enterica* serovars in the mouse model. Int J Med Microbiol. 2016; 306(8):697-706.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. An antigen-binding molecule comprising a reduced charge Sso7d (rcSso7d) antigen-binding protein, wherein the antigen-binding molecule comprises a reduced charge Sso7d (rcSso7d) antigen-binding protein that binds:

a) *Listeria monocytogenes* protein LMOf2365_0639, wherein the antigen-binding protein comprises a variable region having the amino acid sequence of any one of SEQ ID NOs: 1-8;

or b) *Salmonella typhi* Native Omp, said Native Omp comprising the amino acid sequence of *Salmonella typhi* membrane proteins OmpA, OmpW, OmpC, OmpF, OmpD, and phoE, wherein the antigen-binding protein comprises a variable region having the amino acid sequence of any one of SEQ ID NOs: 58-71;

or c) *Escherichia coli* OmpW, wherein the antigen-binding protein comprises a variable region having the amino acid sequence of any one of SEQ ID NOs: 73-80;

or d) *Escherichia coli* OmpA, wherein the antigen-binding protein comprises a variable region having the amino acid sequence of any one of SEQ ID NOs: 81-83.

2. The antigen-binding molecule of claim 1, wherein the antigen-binding molecule binds *Listeria monocytogenes* protein LMOf2365_0639 and comprises a variable region having the amino acid sequence of any one of SEQ ID NOs: 1-8.

3. The antigen-binding molecule of claim 2, wherein the rcSso7d antigen-binding protein comprises:

(i) the amino acid sequence of any one of SEQ ID NOs: 13-15; or (ii) an amino acid sequence having no more than ten conserved amino acid substitutions with any one of SEQ ID NOs: 13-15, wherein any conserved amino acid substitutions do not occur in the variable region.

4. The antigen-binding molecule of claim 2, wherein the rcSso7d antigen-binding protein comprises:

(i) the amino acid sequence of any one of SEQ ID NOs: 16-19; or (ii) an amino acid sequence having no more than seven conserved amino acid substitutions with any one of SEQ ID NOs: 16-19, wherein any conserved amino acid substitutions do not occur in the variable region.

5. The antigen-binding molecule of claim 1, wherein the antigen-binding molecule binds *Salmonella typhi* Native Omp, said Native Omp comprising the amino acid sequence of *Salmonella typhi* membrane proteins OmpA, OmpW, OmpC, OmpF, OmpD, and phoE, and wherein the antigen-binding protein comprises a variable region having the amino acid sequence of any one of SEQ ID NOs: 58-71.

6. The antigen-binding molecule of claim 5, wherein the rcSso7d antigen-binding protein comprises:

(i) the amino acid sequence of any one of SEQ ID NOs: 33-46; or (ii) an amino acid sequence having no more than ten conserved amino acid substitutions with any one of SEQ ID NOs: 33-46, wherein any conserved amino acid substitutions do not occur in the variable region.

7. The antigen-binding molecule of claim 1, wherein the antigen-binding molecule binds *Escherichia coli* OmpW and comprises a variable region having the amino acid sequence of any one of SEQ ID NOs: 73-80.

8. The antigen-binding molecule of claim 7, wherein the rcSso7d antigen-binding protein comprises:

(i) the amino acid sequence of any one of SEQ ID NOs: 47-54; or (ii) an amino acid sequence having no more than ten conserved amino acid substitutions with any one of SEQ ID NOs: 47-54, wherein any conserved amino acid substitutions do not occur in the variable region.

9. The antigen-binding molecule of claim 1, wherein the antigen-binding molecule binds *Escherichia coli* OmpA and comprises a variable region having the amino acid sequence of any one of SEQ ID NOs: 81-83.

10. The antigen-binding molecule of claim 9, wherein the rcSso7d antigen-binding protein comprises:

(i) the amino acid sequence of any one of SEQ ID NOs: 55-57; or (ii) an amino acid sequence having no more than ten conserved amino acid substitutions with any one of SEQ ID NOs: 55-57, wherein any conserved amino acid substitutions do not occur in the variable region.

11. An antigen-binding molecule comprising a reduced charge Sso7d (rcSso7d) antigen-binding protein, wherein the rcSso7d antigen-binding protein comprises the amino acid sequence of any one of SEQ ID NOs: 13-19 or 33-57.

12. The antigen-binding molecule of claim 1, further comprising an enzyme, a fluorescent protein, an immunoglobulin, a peptide tag, a small molecule, or a combination thereof.

13. The antigen-binding molecule of claim 12, wherein the antigen-binding molecule comprises:

an enzyme selected from the group consisting of alkaline phosphatase, horseradish peroxidase, and β-galactosidase;

a fluorescent protein selected from the group consisting of TagBFP, mTagBFP2, Azurite, EBFP2, EBFP2, Sirius, Sapphire, T-Sapphire, ECFP, Cerulean, SCFP3A, mTurquoise, mTurquoise2, monomeric Midoriishi-Cyan, TagCFP, mTFP1, EGFP, Emerald, Superfolder GFP, Monomeric Azami Green, TagGFP2, mUKG, mWasabi, Clover, mNeonGreen, EYFP, Citrine, Venus, SYFP2, TagYFP, Monomeric Kusabira-Orange, mKOκ, mKO2, mOrange, mOrange2, mRaspberry, mCherry, mStrawberry, mTangerine, tdTomato, TagRFP, TagRFP-T, mApple, mRuby, mRuby2, mPlum, HcRed-Tandem, mKate2, mNeptune, and NirFP;

a peptide tag selected from the group consisting of a His tag, a biotin acceptor tag, an HA tag, a c-Myc tag, a streptavidin tag, and a FLAG tag;

biotin; or a combination thereof.

14. A composition comprising an antigen-binding molecule according to claim 1 and a buffer, wherein the buffer has a pH≤6.0, optionally wherein the buffer has a pH of 5.0-6.0.

15. A method of detecting a protein in a sample, the method comprising:

(a) contacting the sample with an antigen-binding molecule of claim 1; and (b) detecting, if present, protein bound by the antigen-binding molecule.

16. A method of detecting bacteria in a sample comprising:

(a) contacting the sample with an antigen-binding molecule of claim 1; and (b) detecting, if present, bacteria bound by the antigen-binding molecule.

17. A kit comprising the antigen-binding molecule of claim 1.

18. An antigen-binding molecule comprising a reduced charge Sso7d (rcSso7d) antigen-binding protein, wherein the rcSso7d antigen-binding protein comprises the amino acid sequence of any one of SEQ ID NOs: 13-19 or 33-57 or an amino acid sequence having no more than seven conserved amino acid substitutions with any one of SEQ ID NOs: 55-57, wherein any conserved amino acid substitutions do not occur in a variable region of the rcSso7d antigen-binding protein.

* * * * *

SEQUENCE LISTING

<160> NUMBER OF SEQ ID NOS: 108

<210> SEQ ID NO 1
<211> LENGTH: 6
<212> TYPE: PRT
<213> ORGANISM: Artificial Sequence
<220> FEATURE:
<223> OTHER INFORMATION: Synthetic

<400> SEQUENCE: 1

Asp Gly Ser Asn Cys Tyr
1 5

<210> SEQ ID NO 2
<211> LENGTH: 6
<212> TYPE: PRT
<213> ORGANISM: Artificial Sequence
<220> FEATURE:
<223> OTHER INFORMATION: Synthetic

<400> SEQUENCE: 2

Asp Gly His Lys Cys Leu
1 5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Ile Lys Tyr Ile Asp Ser Arg Trp Ile
1 5

<210> SEQ ID NO 4
<211> LENGTH: 6
<212> TYPE: PRT
<213> ORGANISM: Artificial Sequence
<220> FEATURE:
<223> OTHER INFORMATION: Synthetic

<400> SEQUENCE: 4

Asp Gly Tyr Arg Cys Trp
1 5

<210> SEQ ID NO 5
<211> LENGTH: 9
<212> TYPE: PRT
<213> ORGANISM: Artificial Sequence
<220> FEATURE:
<223> OTHER INFORMATION: Synthetic

<400> SEQUENCE: 5

Trp Arg Ala Trp Asp Ala Lys Tyr Ile
1 5

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Asp Gly His His Cys Trp
1 5

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

```
Ile Ala Tyr Tyr Tyr Tyr Ser Ser Ile Lys
1               5                   10
```

<210> SEQ ID NO 8
<211> LENGTH: 9
<212> TYPE: PRT
<213> ORGANISM: Artificial Sequence
<220> FEATURE:
<223> OTHER INFORMATION: Synthetic

<400> SEQUENCE: 8

```
Asn Ile Tyr Trp Trp Asn Ile Ser Tyr
1               5
```

<210> SEQ ID NO 9
<211> LENGTH: 57
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 9

```
Met Ala Thr Val Lys Phe Thr Tyr Gln Gly Glu Glu Lys Gln Val Asp
1               5                   10                  15

Ile Ser Lys Ile Lys Xaa Ala Xaa Arg Xaa Gly Gln Xaa Ile Xaa Phe
            20                  25                  30
```

```
Xaa Tyr Asp Glu Gly Gly Gly Ala Xaa Gly Xaa Gly Xaa Val Ser Glu
        35                  40                  45

Lys Asp Ala Pro Lys Glu Leu Leu Gln
    50                  55
```

<210> SEQ ID NO 10
<211> LENGTH: 57
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 10

```
Met Ala Thr Val Lys Phe Thr Tyr Gln Gly Glu Glu Lys Gln Val Asp
1               5                   10                  15

Ile Ser Lys Ile Lys Xaa Val Xaa Arg Xaa Gly Gln Xaa Ile Xaa Phe
            20                  25                  30

Xaa Tyr Asp Glu Gly Gly Gly Ala Xaa Gly Xaa Gly Xaa Val Ser Glu
        35                  40                  45

Lys Asp Ala Pro Lys Glu Leu Leu Gln
    50                  55
```

<210> SEQ ID NO 11
<211> LENGTH: 58
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid

```
<220> FEATURE:
<221> NAME/KEY: misc_feature
<222> LOCATION: (27)..(27)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (42)..(42)
<223> OTHER INFORMATION: Xaa can be any naturally occurring amino acid
<220> FEATURE:
<221> NAME/KEY: misc_feature
<222> LOCATION: (44)..(44)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid

<400> SEQUENCE: 11

Met Ala Thr Val Lys Phe Thr Tyr Gln Gly Glu Glu Lys Gln Val Asp
1               5                   10                  15

Ile Ser Lys Ile Lys Xaa Ala Xaa Xaa Arg Xaa Gly Gln Xaa Ile Xaa
            20                  25                  30

Phe Xaa Tyr Asp Glu Gly Gly Gly Ala Xaa Gly Xaa Gly Xaa Val Ser
        35                  40                  45

Glu Lys Asp Ala Pro Lys Glu Leu Leu Gln
    50                  55


<210> SEQ ID NO 12
<211> LENGTH: 34
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid

<400> SEQUENCE: 12

Met Ala Thr Val Lys Phe Thr Tyr Gln Gly Glu Glu Lys Gln Val Asp
1               5                   10                  15
```

```
Ile Ser Lys Ile Lys Xaa Val Xaa Arg Xaa Gly Gln Xaa Ile Xaa Phe
            20                  25                  30

Xaa Leu


<210> SEQ ID NO 13
<211> LENGTH: 62
<212> TYPE: PRT
<213> ORGANISM: Artificial Sequence
<220> FEATURE:
<223> OTHER INFORMATION: Synthetic

<400> SEQUENCE: 13

Met Ala Thr Val Lys Phe Thr Tyr Gln Gly Glu Glu Lys Gln Val Asp
1               5                   10                  15

Ile Ser Lys Ile Lys Ile Ala Lys Arg Tyr Gly Gln Ile Ile Asp Phe
            20                  25                  30

Ser Tyr Asp Glu Gly Gly Gly Ala Arg Gly Trp Gly Ile Val Ser Glu
        35                  40                  45

Lys Asp Ala Pro Lys Glu Leu Leu Gln Met Leu Glu Lys Gln
    50                  55                  60


<210> SEQ ID NO 14
<211> LENGTH: 61
<212> TYPE: PRT
<213> ORGANISM: Artificial Sequence
<220> FEATURE:
<223> OTHER INFORMATION: Synthetic

<400> SEQUENCE: 14

Met Ala Thr Val Lys Phe Thr Tyr Gln Gly Glu Glu Lys Gln Val Asp
1               5                   10                  15

Ile Ser Lys Ile Lys Trp Val Arg Arg Ala Gly Gln Trp Ile Asp Phe
            20                  25                  30

Ala Tyr Asp Glu Gly Gly Gly Ala Lys Gly Tyr Gly Ile Val Ser Glu
        35                  40                  45

Lys Asp Ala Pro Lys Glu Leu Leu Gln Cys Trp Lys Ser
    50                  55                  60


<210> SEQ ID NO 15
<211> LENGTH: 63
<212> TYPE: PRT
<213> ORGANISM: Artificial Sequence
<220> FEATURE:
<223> OTHER INFORMATION: Synthetic

<400> SEQUENCE: 15

Met Ala Thr Val Lys Phe Thr Tyr Gln Gly Glu Glu Lys Gln Val Asp
1               5                   10                  15

Ile Ser Lys Ile Lys Ile Ala Val Tyr Arg Tyr Gly Gln Tyr Ile Tyr
            20                  25                  30

Phe Ser Tyr Asp Glu Gly Gly Gly Ala Ser Gly Ile Gly Lys Val Ser
        35                  40                  45

Glu Lys Asp Ala Pro Lys Glu Leu Leu Gln Met Leu Glu Lys Gln
    50                  55                  60


<210> SEQ ID NO 16
<211> LENGTH: 34
<212> TYPE: PRT
<213> ORGANISM: Artificial Sequence
<220> FEATURE:
<223> OTHER INFORMATION: Synthetic
```

<400> SEQUENCE: 16

```
Met Ala Thr Val Lys Phe Thr Tyr Gln Gly Glu Glu Lys Gln Val Asp
1               5                   10                  15

Ile Ser Lys Ile Lys Asp Val Gly Arg Ser Gly Gln Asn Ile Cys Phe
            20                  25                  30

Tyr Leu
```

<210> SEQ ID NO 17
<211> LENGTH: 34
<212> TYPE: PRT
<213> ORGANISM: Artificial Sequence
<220> FEATURE:
<223> OTHER INFORMATION: Synthetic

<400> SEQUENCE: 17

```
Met Ala Thr Val Lys Phe Thr Tyr Gln Gly Glu Glu Lys Gln Val Asp
1               5                   10                  15

Ile Ser Lys Ile Lys Asp Val Gly Arg His Gly Gln Lys Ile Cys Phe
            20                  25                  30

Leu Leu
```

<210> SEQ ID NO 18
<211> LENGTH: 34
<212> TYPE: PRT
<213> ORGANISM: Artificial Sequence
<220> FEATURE:
<223> OTHER INFORMATION: Synthetic

<400> SEQUENCE: 18

```
Met Ala Thr Val Lys Phe Thr Tyr Gln Gly Glu Glu Lys Gln Val Asp
1               5                   10                  15

Ile Ser Lys Ile Lys Asp Val Gly Arg Tyr Gly Gln Arg Ile Cys Phe
            20                  25                  30

Trp Leu
```

<210> SEQ ID NO 19
<211> LENGTH: 34
<212> TYPE: PRT
<213> ORGANISM: Artificial Sequence
<220> FEATURE:
<223> OTHER INFORMATION: Synthetic

<400> SEQUENCE: 19

```
Met Ala Thr Val Lys Phe Thr Tyr Gln Gly Glu Glu Lys Gln Val Asp
1               5                   10                  15

Ile Ser Lys Ile Lys Asp Val Gly Arg His Gly Gln His Ile Cys Phe
            20                  25                  30

Trp Leu
```

<210> SEQ ID NO 20
<211> LENGTH: 40
<212> TYPE: DNA
<213> ORGANISM: Artificial Sequence
<220> FEATURE:
<223> OTHER INFORMATION: Synthetic

<400> SEQUENCE: 20

```
ctggcatatg gttaatatcc cggacccggt tctgaagagc                          40
```

<210> SEQ ID NO 21

<211> LENGTH: 33
<212> TYPE: DNA
<213> ORGANISM: Artificial Sequence
<220> FEATURE:
<223> OTHER INFORMATION: Synthetic

<400> SEQUENCE: 21
tattaggatc ccgtgtttgg gagggcggcg tta 33

<210> SEQ ID NO 22
<211> LENGTH: 35
<212> TYPE: DNA
<213> ORGANISM: Artificial Sequence
<220> FEATURE:
<223> OTHER INFORMATION: Synthetic

<400> SEQUENCE: 22
aggcagtctc atatgtgtgc aaccgtgaaa ttcac 35

<210> SEQ ID NO 23
<211> LENGTH: 29
<212> TYPE: DNA
<213> ORGANISM: Artificial Sequence
<220> FEATURE:
<223> OTHER INFORMATION: Synthetic

<400> SEQUENCE: 23
acccctctcg agttattgct tttccagca 29

<210> SEQ ID NO 24
<211> LENGTH: 1632
<212> TYPE: DNA
<213> ORGANISM: Artificial Sequence
<220> FEATURE:
<223> OTHER INFORMATION: Synthetic

<400> SEQUENCE: 24
atgggcagca gccatcatca tcatcatcac agcagcggcc tggtgccgcg cggcagccat 60
atggaattcg ttaatatccc ggacccggtt ctgaagagct acctcaatgg tctgctgggc 120
caaagcagca cgagcgatat caccgaagcg cagatggata ccatcacgaa tgtgaccatc 180
agcaacagca gcctcaccga tctgaccggc ctcgactacg cccacaatct gacgattctc 240
cacctcagta acacgggtgt gaccgactac gcgctcgtgg ccaagattcc gagtctgacg 300
aatctgagca ttgcgggtga taacctcacc aatgacagtc tgccggatct gaacaacctc 360
agcaacatca cgaacctcaa tctgagcccg ggcaagctgg ataacaacgc gctgacgaag 420
ttcaataaaa tgagcaagct gagctatctg aatctggaca gcaacccgag catcacgaac 480
atcatgccgc tcaaaagcat cccgaatctg gcgacgctgt tcgtgcagtt ctgcggcatt 540
aacgacttcc gcggcatcga tacgttcccg aagctggtga gtctgagtgc gtatggtcag 600
aacgtgggcc gcacggtgct gatcaacagc agcattaaga gcagtgcgct gaacttcgat 660
gaggccaacc agacgatctt cgtgccattt accctcatga ccgaacgcgg cgtgaacttc 720
gacggttacc tcttcccatt caccaccaat accagcagcg ccagtacgta cttcaccctc 780
aacgagacca agattgacgg tagtcgtctc acgatcgatg acaagggtat cacggtgagc 840
ggtatcacca aaagctactt cgacacgatt acgaagatgg agtataacgc cctctacaac 900
aacccggccg gtagttatca gacgccgccg aacttcaaca actacagcgt tagtggcggc 960
agctacgatc actacttcga catcgaccac agcctcacca ttacgaacga cagcgccatc 1020
agctacggtg agcagacgac cgtgacggag gagcagtttc tgaaggatgt gcacgcggaa 1080

```
accgacgatg gcaccccggt taccagcgac ttcaacacgg tggtggattt cagcaagccg   1140

ggcgtgtaca ccgttacgct gaatgccgaa aatgcggccg gtctcaaagc gacgccaacc   1200

caagttacgg ttaccatcca cgccaagccg gtgattaccg cggacaaaag catcagctac   1260

accaaggaca gtacgaaaac cgatcagcag tttctgcaag atattagcgc gaagaccagt   1320

gacggcagca aggttacgag tgactttgac agcgtggttg acctcgcgaa ggtgggcacg   1380

tataaggtga cgctgaatgc ggttagcgcg gatggtctga acgccgaccc agtgatcgtg   1440

ctcgtgaatg tggtggaagg caatgaacca ccaaccccac cagccccggg cccagatccg   1500

acgccagatc caaccccgaa cccgaacaac ccgaacatca atccgaatcc ggacaacggt   1560

cagagtgcga acagcgagaa cgcgagcaat ccaagcaaca gcgaagttaa cgccgccctc   1620

ccaaacacgt aa                                                        1632
```

```
<210> SEQ ID NO 25
<211> LENGTH: 543
<212> TYPE: PRT
<213> ORGANISM: Artificial Sequence
<220> FEATURE:
<223> OTHER INFORMATION: Synthetic

<400> SEQUENCE: 25

Met Gly Ser Ser His His His His His His Ser Ser Gly Leu Val Pro
1               5                   10                  15

Arg Gly Ser His Met Glu Phe Val Asn Ile Pro Asp Pro Val Leu Lys
            20                  25                  30

Ser Tyr Leu Asn Gly Leu Leu Gly Gln Ser Ser Thr Ser Asp Ile Thr
        35                  40                  45

Glu Ala Gln Met Asp Thr Ile Thr Asn Val Thr Ile Ser Asn Ser Ser
    50                  55                  60

Leu Thr Asp Leu Thr Gly Leu Asp Tyr Ala His Asn Leu Thr Ile Leu
65                  70                  75                  80

His Leu Ser Asn Thr Gly Val Thr Asp Tyr Ala Leu Val Ala Lys Ile
                85                  90                  95

Pro Ser Leu Thr Asn Leu Ser Ile Ala Gly Asp Asn Leu Thr Asn Asp
            100                 105                 110

Ser Leu Pro Asp Leu Asn Asn Leu Ser Asn Ile Thr Asn Leu Asn Leu
        115                 120                 125

Ser Pro Gly Lys Leu Asp Asn Asn Ala Leu Thr Lys Phe Asn Lys Met
    130                 135                 140

Ser Lys Leu Ser Tyr Leu Asn Leu Asp Ser Asn Pro Ser Ile Thr Asn
145                 150                 155                 160

Ile Met Pro Leu Lys Ser Ile Pro Asn Leu Ala Thr Leu Phe Val Gln
                165                 170                 175

Phe Cys Gly Ile Asn Asp Phe Arg Gly Ile Asp Thr Phe Pro Lys Leu
            180                 185                 190

Val Ser Leu Ser Ala Tyr Gly Gln Asn Val Gly Arg Thr Val Leu Ile
        195                 200                 205

Asn Ser Ser Ile Lys Ser Ser Ala Leu Asn Phe Asp Glu Ala Asn Gln
    210                 215                 220

Thr Ile Phe Val Pro Phe Thr Leu Met Thr Glu Arg Gly Val Asn Phe
225                 230                 235                 240

Asp Gly Tyr Leu Phe Pro Phe Thr Thr Asn Thr Ser Ser Ala Ser Thr
                245                 250                 255
```

```
Tyr Phe Thr Leu Asn Glu Thr Lys Ile Asp Gly Ser Arg Leu Thr Ile
            260                 265                 270

Asp Asp Lys Gly Ile Thr Val Ser Gly Ile Thr Lys Ser Tyr Phe Asp
        275                 280                 285

Thr Ile Thr Lys Met Glu Tyr Asn Ala Leu Tyr Asn Asn Pro Ala Gly
    290                 295                 300

Ser Tyr Gln Thr Pro Pro Asn Phe Asn Asn Tyr Ser Val Ser Gly Gly
305                 310                 315                 320

Ser Tyr Asp His Tyr Phe Asp Ile Asp His Ser Leu Thr Ile Thr Asn
                325                 330                 335

Asp Ser Ala Ile Ser Tyr Gly Glu Gln Thr Thr Val Thr Glu Glu Gln
            340                 345                 350

Phe Leu Lys Asp Val His Ala Glu Thr Asp Asp Gly Thr Pro Val Thr
        355                 360                 365

Ser Asp Phe Asn Thr Val Val Asp Phe Ser Lys Pro Gly Val Tyr Thr
    370                 375                 380

Val Thr Leu Asn Ala Glu Asn Ala Ala Gly Leu Lys Ala Thr Pro Thr
385                 390                 395                 400

Gln Val Thr Val Thr Ile His Ala Lys Pro Val Ile Thr Ala Asp Lys
                405                 410                 415

Ser Ile Ser Tyr Thr Lys Asp Ser Thr Lys Thr Asp Gln Gln Phe Leu
            420                 425                 430

Gln Asp Ile Ser Ala Lys Thr Ser Asp Gly Ser Lys Val Thr Ser Asp
        435                 440                 445

Phe Asp Ser Val Val Asp Leu Ala Lys Val Gly Thr Tyr Lys Val Thr
    450                 455                 460

Leu Asn Ala Val Ser Ala Asp Gly Leu Asn Ala Asp Pro Val Ile Val
465                 470                 475                 480

Leu Val Asn Val Val Glu Gly Asn Glu Pro Pro Thr Pro Pro Ala Pro
                485                 490                 495

Gly Pro Asp Pro Thr Pro Asp Pro Thr Pro Asn Pro Asn Asn Pro Asn
            500                 505                 510

Ile Asn Pro Asn Pro Asp Asn Gly Gln Ser Ala Asn Ser Glu Asn Ala
        515                 520                 525

Ser Asn Pro Ser Asn Ser Glu Val Asn Ala Ala Leu Pro Asn Thr
    530                 535                 540
```

<210> SEQ ID NO 26
<211> LENGTH: 1686
<212> TYPE: DNA
<213> ORGANISM: Artificial Sequence
<220> FEATURE:
<223> OTHER INFORMATION: Synthetic

<400> SEQUENCE: 26

```
atgggcagca gccatcatca tcatcatcac agcagcggcc tggtgccgcg cggcagccat      60

atggttaata tcccggaccc ggttctgaag agctacctca atggtctgct gggccaaagc     120

agcacgagcg atatcaccga agcgcagatg gataccatca cgaatgtgac catcagcaac     180

agcagcctca ccgatctgac cggcctcgac tacgcccaca atctgacgat tctccacctc     240

agtaacacgg gtgtgaccga ctacgcgctc gtggccaaga ttccgagtct gacgaatctg     300

agcattgcgg gtgataacct caccaatgac agtctgccgg atctgaacaa cctcagcaac     360

atcacgaacc tcaatctgag cccgggcaag ctggataaca acgcgctgac gaagttcaat     420

aaaatgagca agctgagcta tctgaatctg gacagcaacc cgagcatcac gaacatcatg     480
```

```
ccgctcaaaa gcatcccgaa tctggcgacg ctgttcgtgc agttctgcgg cattaacgac    540

ttccgcggca tcgatacgtt cccgaagctg gtgagtctga gtgcgtatgg tcagaacgtg    600

ggccgcacgg tgctgatcaa cagcagcatt aagagcagtg cgctgaactt cgatgaggcc    660

aaccagacga tcttcgtgcc atttaccctc atgaccgaac gcggcgtgaa cttcgacggt    720

tacctcttcc cattcaccac caataccagc agcgccagta cgtacttcac cctcaacgag    780

accaagattg acggtagtcg tctcacgatc gatgacaagg gtatcacggt gagcggtatc    840

accaaaagct acttcgacac gattacgaag atggagtata acgccctcta caacaacccg    900

gccggtagtt atcagacgcc gccgaacttc aacaactaca gcgttagtgg cggcagctac    960

gatcactact tcgacatcga ccacagcctc accattacga acgacagcgc catcagctac   1020

ggtgagcaga cgaccgtgac ggaggagcag tttctgaagg atgtgcacgc ggaaaccgac   1080

gatggcaccc cggttaccag cgacttcaac acggtggtgg atttcagcaa gccgggcgtg   1140

tacaccgtta cgctgaatgc cgaaaatgcg gccggtctca aagcgacgcc aacccaagtt   1200

acggttacca tccacgccaa gccggtgatt accgcggaca aaagcatcag ctacaccaag   1260

gacagtacga aaaccgatca gcagtttctg caagatatta gcgcgaagac cagtgacggc   1320

agcaaggtta cgagtgactt tgacagcgtg gttgacctcg cgaaggtggg cacgtataag   1380

gtgacgctga atgcggttag cgcggatggt ctgaacgccg acccagtgat cgtgctcgtg   1440

aatgtggtgg aaggcaatga accaccaacc ccaccagccc cggcccaga tccgacgcca   1500

gatccaaccc cgaacccgaa caacccgaac atcaatccga atccggacaa cggtcagagt   1560

gcgaacagcg agaacgcgag caatccaagc aacagcgaag ttaacgccgc cctcccaaac   1620

acgggatcca tggcgggcgg cctgaacgat atttttgaag cgcagaaaat tgaatggcat   1680

gaataa                                                              1686
```

```
<210> SEQ ID NO 27
<211> LENGTH: 561
<212> TYPE: PRT
<213> ORGANISM: Artificial Sequence
<220> FEATURE:
<223> OTHER INFORMATION: Synthetic

<400> SEQUENCE: 27

Met Gly Ser Ser His His His His His His Ser Ser Gly Leu Val Pro
1               5                   10                  15

Arg Gly Ser His Met Val Asn Ile Pro Asp Pro Val Leu Lys Ser Tyr
            20                  25                  30

Leu Asn Gly Leu Leu Gly Gln Ser Ser Thr Ser Asp Ile Thr Glu Ala
        35                  40                  45

Gln Met Asp Thr Ile Thr Asn Val Thr Ile Ser Asn Ser Ser Leu Thr
    50                  55                  60

Asp Leu Thr Gly Leu Asp Tyr Ala His Asn Leu Thr Ile Leu His Leu
65                  70                  75                  80

Ser Asn Thr Gly Val Thr Asp Tyr Ala Leu Val Ala Lys Ile Pro Ser
                85                  90                  95

Leu Thr Asn Leu Ser Ile Ala Gly Asp Asn Leu Thr Asn Asp Ser Leu
            100                 105                 110

Pro Asp Leu Asn Asn Leu Ser Asn Ile Thr Asn Leu Asn Leu Ser Pro
        115                 120                 125

Gly Lys Leu Asp Asn Asn Ala Leu Thr Lys Phe Asn Lys Met Ser Lys
    130                 135                 140
```

```
Leu Ser Tyr Leu Asn Leu Asp Ser Asn Pro Ser Ile Thr Asn Ile Met
145                 150                 155                 160

Pro Leu Lys Ser Ile Pro Asn Leu Ala Thr Leu Phe Val Gln Phe Cys
                165                 170                 175

Gly Ile Asn Asp Phe Arg Gly Ile Asp Thr Phe Pro Lys Leu Val Ser
            180                 185                 190

Leu Ser Ala Tyr Gly Gln Asn Val Gly Arg Thr Val Leu Ile Asn Ser
        195                 200                 205

Ser Ile Lys Ser Ser Ala Leu Asn Phe Asp Glu Ala Asn Gln Thr Ile
    210                 215                 220

Phe Val Pro Phe Thr Leu Met Thr Glu Arg Gly Val Asn Phe Asp Gly
225                 230                 235                 240

Tyr Leu Phe Pro Phe Thr Thr Asn Thr Ser Ser Ala Ser Thr Tyr Phe
                245                 250                 255

Thr Leu Asn Glu Thr Lys Ile Asp Gly Ser Arg Leu Thr Ile Asp Asp
            260                 265                 270

Lys Gly Ile Thr Val Ser Gly Ile Thr Lys Ser Tyr Phe Asp Thr Ile
        275                 280                 285

Thr Lys Met Glu Tyr Asn Ala Leu Tyr Asn Asn Pro Ala Gly Ser Tyr
    290                 295                 300

Gln Thr Pro Pro Asn Phe Asn Asn Tyr Ser Val Ser Gly Gly Ser Tyr
305                 310                 315                 320

Asp His Tyr Phe Asp Ile Asp His Ser Leu Thr Ile Thr Asn Asp Ser
                325                 330                 335

Ala Ile Ser Tyr Gly Glu Gln Thr Thr Val Thr Glu Glu Gln Phe Leu
            340                 345                 350

Lys Asp Val His Ala Glu Thr Asp Asp Gly Thr Pro Val Thr Ser Asp
        355                 360                 365

Phe Asn Thr Val Val Asp Phe Ser Lys Pro Gly Val Tyr Thr Val Thr
    370                 375                 380

Leu Asn Ala Glu Asn Ala Ala Gly Leu Lys Ala Thr Pro Thr Gln Val
385                 390                 395                 400

Thr Val Thr Ile His Ala Lys Pro Val Ile Thr Ala Asp Lys Ser Ile
                405                 410                 415

Ser Tyr Thr Lys Asp Ser Thr Lys Thr Asp Gln Gln Phe Leu Gln Asp
            420                 425                 430

Ile Ser Ala Lys Thr Ser Asp Gly Ser Lys Val Thr Ser Asp Phe Asp
        435                 440                 445

Ser Val Val Asp Leu Ala Lys Val Gly Thr Tyr Lys Val Thr Leu Asn
    450                 455                 460

Ala Val Ser Ala Asp Gly Leu Asn Ala Asp Pro Val Ile Val Leu Val
465                 470                 475                 480

Asn Val Val Glu Gly Asn Glu Pro Pro Thr Pro Pro Ala Pro Gly Pro
                485                 490                 495

Asp Pro Thr Pro Asp Pro Thr Pro Asn Pro Asn Asn Pro Asn Ile Asn
            500                 505                 510

Pro Asn Pro Asp Asn Gly Gln Ser Ala Asn Ser Glu Asn Ala Ser Asn
        515                 520                 525

Pro Ser Asn Ser Glu Val Asn Ala Ala Leu Pro Asn Thr Gly Ser Met
    530                 535                 540

Ala Gly Gly Leu Asn Asp Ile Phe Glu Ala Gln Lys Ile Glu Trp His
545                 550                 555                 560
```

Glu

<210> SEQ ID NO 28
<211> LENGTH: 252
<212> TYPE: DNA
<213> ORGANISM: Artificial Sequence
<220> FEATURE:
<223> OTHER INFORMATION: Synthetic

<400> SEQUENCE: 28
atgggcagca gccatcatca tcatcatcac agcagcggcc tggtgccgcg cggcagccat 60
atgtgtgcaa ccgtgaaatt cacataccaa ggcgaagaaa aacaggtgga tattagcaaa 120
atcaagaacg tgcatcgtca tggccagaaa atttacttta tctatgatga aggtggtggt 180
gccaaaggtc atggtaaagt gagcgaaaaa gatgcaccga aagaactgct gcagatgctg 240
gaaaagcaat aa 252

<210> SEQ ID NO 29
<211> LENGTH: 83
<212> TYPE: PRT
<213> ORGANISM: Artificial Sequence
<220> FEATURE:
<223> OTHER INFORMATION: Synthetic

<400> SEQUENCE: 29

Met Gly Ser Ser His His His His His His Ser Ser Gly Leu Val Pro
1 5 10 15

Arg Gly Ser His Met Cys Ala Thr Val Lys Phe Thr Tyr Gln Gly Glu
20 25 30

Glu Lys Gln Val Asp Ile Ser Lys Ile Lys Ile Ala Lys Arg Tyr Gly
35 40 45

Gln Ile Ile Asp Phe Ser Tyr Asp Glu Gly Gly Gly Ala Arg Gly Trp
50 55 60

Gly Ile Val Ser Glu Lys Asp Ala Pro Lys Glu Leu Leu Gln Met Leu
65 70 75 80

Glu Lys Gln

<210> SEQ ID NO 30
<211> LENGTH: 350
<212> TYPE: PRT
<213> ORGANISM: Salmonella typhimurium

<400> SEQUENCE: 30

Met Lys Lys Thr Ala Ile Ala Ile Ala Val Ala Leu Ala Gly Phe Ala
1 5 10 15

Thr Val Ala Gln Ala Ala Pro Lys Asp Asn Thr Trp Tyr Ala Gly Ala
20 25 30

Lys Leu Gly Trp Ser Gln Tyr His Asp Thr Gly Phe Ile His Asn Asp
35 40 45

Gly Pro Thr His Glu Asn Gln Leu Gly Ala Gly Ala Phe Gly Gly Tyr
50 55 60

Gln Val Asn Pro Tyr Val Gly Phe Glu Met Gly Tyr Asp Trp Leu Gly
65 70 75 80

Arg Met Pro Tyr Lys Gly Asp Asn Ile Asn Gly Ala Tyr Lys Ala Gln
85 90 95

Gly Val Gln Leu Thr Ala Lys Leu Gly Tyr Pro Ile Thr Asp Asp Leu
100 105 110

Asp Val Tyr Thr Arg Leu Gly Gly Met Val Trp Arg Ala Asp Thr Lys

```
        115                 120                 125

Ser Asn Val Pro Gly Gly Pro Ser Thr Lys Asp His Asp Thr Gly Val
    130                 135                 140

Ser Pro Val Phe Ala Gly Gly Ile Glu Tyr Ala Ile Thr Pro Glu Ile
145                 150                 155                 160

Ala Thr Arg Leu Glu Tyr Gln Trp Thr Asn Asn Ile Gly Asp Ala Asn
                165                 170                 175

Thr Ile Gly Thr Arg Pro Asp Asn Gly Leu Leu Ser Val Gly Val Ser
            180                 185                 190

Tyr Arg Phe Gly Gln Gln Glu Ala Ala Pro Val Val Ala Pro Ala Pro
        195                 200                 205

Ala Pro Ala Pro Glu Val Gln Thr Lys His Phe Thr Leu Lys Ser Asp
    210                 215                 220

Val Leu Phe Asn Phe Asn Lys Ser Thr Leu Lys Pro Glu Gly Gln Gln
225                 230                 235                 240

Ala Leu Asp Gln Leu Tyr Ser Gln Leu Ser Asn Leu Asp Pro Lys Asp
                245                 250                 255

Gly Ser Val Val Val Leu Gly Phe Thr Asp Arg Ile Gly Ser Asp Ala
            260                 265                 270

Tyr Asn Gln Gly Leu Ser Glu Lys Arg Ala Gln Ser Val Val Asp Tyr
        275                 280                 285

Leu Ile Ser Lys Gly Ile Pro Ser Asp Lys Ile Ser Ala Arg Gly Met
    290                 295                 300

Gly Glu Ser Asn Pro Val Thr Gly Asn Thr Cys Asp Asn Val Lys Pro
305                 310                 315                 320

Arg Ala Ala Leu Ile Asp Cys Leu Ala Pro Asp Arg Arg Val Glu Ile
                325                 330                 335

Glu Val Lys Gly Val Lys Asp Val Val Thr Gln Pro Gln Ala
            340                 345                 350


<210> SEQ ID NO 31
<211> LENGTH: 350
<212> TYPE: PRT
<213> ORGANISM: Salmonella typhi

<400> SEQUENCE: 31

Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Ala Gly Ala
            20                  25                  30

Lys Leu Gly Trp Ser Gln Tyr His Asp Thr Gly Phe Ile His Asn Asp
        35                  40                  45

Gly Pro Thr His Glu Asn Gln Leu Gly Ala Gly Ala Phe Gly Gly Tyr
    50                  55                  60

Gln Val Asn Pro Tyr Val Gly Phe Glu Met Gly Tyr Asp Trp Leu Gly
65                  70                  75                  80

Arg Met Pro Tyr Lys Gly Asp Asn Thr Asn Gly Ala Tyr Lys Ala Gln
                85                  90                  95

Gly Val Gln Leu Thr Ala Lys Leu Gly Tyr Pro Ile Thr Asp Asp Leu
            100                 105                 110

Asp Val Tyr Thr Arg Leu Gly Gly Met Val Trp Arg Ala Asp Thr Lys
        115                 120                 125

Ser Asn Val Pro Gly Gly Ala Ser Thr Lys Asp His Asp Thr Gly Val
    130                 135                 140
```

```
Ser Pro Val Phe Ala Gly Gly Ile Glu Tyr Ala Ile Thr Pro Glu Ile
145                 150                 155                 160

Ala Thr Arg Leu Glu Tyr Gln Trp Thr Asn Asn Ile Gly Asp Ala Asn
                165                 170                 175

Thr Ile Gly Thr Arg Pro Asp Asn Gly Leu Leu Ser Val Gly Val Ser
            180                 185                 190

Tyr Arg Phe Gly Gln Gln Glu Ala Ala Pro Val Val Ala Pro Ala Pro
        195                 200                 205

Ala Pro Ala Pro Glu Val Gln Thr Lys His Phe Thr Leu Lys Ser Asp
    210                 215                 220

Val Leu Phe Asn Phe Asn Lys Ser Thr Leu Lys Pro Glu Gly Gln Gln
225                 230                 235                 240

Ala Leu Asp Gln Leu Tyr Ser Gln Leu Ser Asn Leu Asp Pro Lys Asp
                245                 250                 255

Gly Ser Val Val Val Leu Gly Phe Thr Asp Arg Ile Gly Ser Asp Ala
            260                 265                 270

Tyr Asn Gln Gly Leu Ser Glu Lys Arg Ala Gln Ser Val Val Asp Tyr
        275                 280                 285

Leu Ile Ser Lys Gly Ile Pro Ser Asp Lys Ile Ser Ala Arg Gly Met
    290                 295                 300

Gly Glu Ser Asn Pro Val Thr Gly Asn Thr Cys Asp Asn Val Lys Pro
305                 310                 315                 320

Arg Ala Ala Leu Ile Asp Cys Leu Ala Pro Asp Arg Arg Val Glu Ile
                325                 330                 335

Glu Val Lys Gly Val Lys Asp Val Val Thr Gln Pro Gln Ala
            340                 345                 350


<210> SEQ ID NO 32
<211> LENGTH: 346
<212> TYPE: PRT
<213> ORGANISM: Escherichia coli

<400> SEQUENCE: 32

Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Thr Gly Ala
            20                  25                  30

Lys Leu Gly Trp Ser Gln Tyr His Asp Thr Gly Phe Ile Asn Asn Asn
        35                  40                  45

Gly Pro Thr His Glu Asn Gln Leu Gly Ala Gly Ala Phe Gly Gly Tyr
    50                  55                  60

Gln Val Asn Pro Tyr Val Gly Phe Glu Met Gly Tyr Asp Trp Leu Gly
65                  70                  75                  80

Arg Met Pro Tyr Lys Gly Ser Val Glu Asn Gly Ala Tyr Lys Ala Gln
                85                  90                  95

Gly Val Gln Leu Thr Ala Lys Leu Gly Tyr Pro Ile Thr Asp Asp Leu
            100                 105                 110

Asp Ile Tyr Thr Arg Leu Gly Gly Met Val Trp Arg Ala Asp Thr Lys
        115                 120                 125

Ser Asn Val Tyr Gly Lys Asn His Asp Thr Gly Val Ser Pro Val Phe
    130                 135                 140

Ala Gly Gly Val Glu Tyr Ala Ile Thr Pro Glu Ile Ala Thr Arg Leu
145                 150                 155                 160

Glu Tyr Gln Trp Thr Asn Asn Ile Gly Asp Ala His Thr Ile Gly Thr
                165                 170                 175
```

```
Arg Pro Asp Asn Gly Met Leu Ser Leu Gly Val Ser Tyr Arg Phe Gly
            180                 185                 190

Gln Gly Glu Ala Ala Pro Val Val Ala Pro Ala Pro Ala Pro Ala Pro
        195                 200                 205

Glu Val Gln Thr Lys His Phe Thr Leu Lys Ser Asp Val Leu Phe Asn
    210                 215                 220

Phe Asn Lys Ala Thr Leu Lys Pro Glu Gly Gln Ala Ala Leu Asp Gln
225                 230                 235                 240

Leu Tyr Ser Gln Leu Ser Asn Leu Asp Pro Lys Asp Gly Ser Val Val
                245                 250                 255

Val Leu Gly Tyr Thr Asp Arg Ile Gly Ser Asp Ala Tyr Asn Gln Gly
            260                 265                 270

Leu Ser Glu Arg Arg Ala Gln Ser Val Val Asp Tyr Leu Ile Ser Lys
        275                 280                 285

Gly Ile Pro Ala Asp Lys Ile Ser Ala Arg Gly Met Gly Glu Ser Asn
    290                 295                 300

Pro Val Thr Gly Asn Thr Cys Asp Asn Val Lys Gln Arg Ala Ala Leu
305                 310                 315                 320

Ile Asp Cys Leu Ala Pro Asp Arg Arg Val Glu Ile Glu Val Lys Gly
                325                 330                 335

Ile Lys Asp Val Val Thr Gln Pro Gln Ala
            340                 345


<210> SEQ ID NO 33
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Xaa can be any naturally occurring amino acid

<400> SEQUENCE: 33

Met Ala Thr Val Lys Phe Thr Tyr Gln Gly Glu Glu Lys Gln Val Asp
1               5                   10                  15

Ile Ser Lys Ile Lys Xaa Val Lys Arg Asp Gly Gln Ser Ile Tyr Phe
            20                  25                  30

Trp Tyr Asp Glu Gly Gly Gly Ala Ile Gly Ala Gly His Val Ser Glu
        35                  40                  45

Lys Asp Ala Pro Lys Glu Leu Leu Glu Lys Gln
    50                  55


<210> SEQ ID NO 34
<211> LENGTH: 59
<212> TYPE: PRT
<213> ORGANISM: Artificial Sequence
<220> FEATURE:
<223> OTHER INFORMATION: Synthetic

<400> SEQUENCE: 34

Met Ala Thr Val Lys Phe Thr Tyr Gln Gly Glu Glu Lys Gln Val Asp
1               5                   10                  15

Ile Ser Lys Ile Lys Ser Val Ser Arg Arg Gly Gln Gly Ile Ala Phe
            20                  25                  30

Ser Tyr Asp Glu Gly Gly Gly Ala Arg Gly Tyr Gly His Val Ser Glu
        35                  40                  45
```

```
Lys Asp Ala Pro Lys Glu Leu Leu Glu Lys Gln
    50                  55


<210> SEQ ID NO 35
<211> LENGTH: 59
<212> TYPE: PRT
<213> ORGANISM: Artificial Sequence
<220> FEATURE:
<223> OTHER INFORMATION: Synthetic

<400> SEQUENCE: 35

Met Ala Thr Val Lys Phe Thr Tyr Gln Gly Glu Glu Lys Gln Val Asp
1               5                   10                  15

Ile Ser Lys Ile Lys Ile Val Ala Arg Ala Gly Gln Trp Ile Trp Phe
            20                  25                  30

Trp Tyr Asp Glu Gly Gly Gly Ala His Gly Arg Gly Gly Val Ser Glu
        35                  40                  45

Lys Asp Ala Pro Lys Glu Leu Leu Glu Lys Gln
    50                  55


<210> SEQ ID NO 36
<211> LENGTH: 59
<212> TYPE: PRT
<213> ORGANISM: Artificial Sequence
<220> FEATURE:
<223> OTHER INFORMATION: Synthetic

<400> SEQUENCE: 36

Met Ala Thr Val Lys Phe Thr Tyr Gln Gly Glu Glu Lys Gln Val Asp
1               5                   10                  15

Ile Ser Lys Ile Lys Gly Val Trp Arg Trp Gly Gln Trp Ile Trp Phe
            20                  25                  30

Trp Tyr Asp Glu Gly Gly Gly Ala Ala Gly Arg Gly Tyr Val Ser Glu
        35                  40                  45

Lys Asp Ala Pro Lys Glu Leu Leu Glu Lys Gln
    50                  55


<210> SEQ ID NO 37
<211> LENGTH: 59
<212> TYPE: PRT
<213> ORGANISM: Artificial Sequence
<220> FEATURE:
<223> OTHER INFORMATION: Synthetic

<400> SEQUENCE: 37

Met Ala Thr Val Lys Phe Thr Tyr Gln Gly Glu Glu Lys Gln Val Asp
1               5                   10                  15

Ile Ser Lys Ile Lys Trp Val Ile Arg His Gly Gln Gly Ile Tyr Phe
            20                  25                  30

Ser Tyr Asp Glu Gly Gly Gly Ala Ile Gly Gly Gly Ser Val Ser Glu
        35                  40                  45

Lys Asp Ala Pro Lys Glu Leu Leu Glu Lys Gln
    50                  55


<210> SEQ ID NO 38
<211> LENGTH: 59
<212> TYPE: PRT
<213> ORGANISM: Artificial Sequence
<220> FEATURE:
<223> OTHER INFORMATION: Synthetic

<400> SEQUENCE: 38
```

```
Met Ala Thr Val Lys Phe Thr Tyr Gln Gly Glu Glu Lys Gln Val Asp
1               5                   10                  15

Ile Ser Lys Ile Lys Trp Val His Arg His Gly Gln Trp Ile Gly Phe
            20                  25                  30

Asp Tyr Asp Glu Gly Gly Gly Ala Ile Gly Asp Gly Ser Val Ser Glu
        35                  40                  45

Lys Asp Ala Pro Lys Glu Leu Leu Glu Lys Gln
    50                  55


<210> SEQ ID NO 39
<211> LENGTH: 59
<212> TYPE: PRT
<213> ORGANISM: Artificial Sequence
<220> FEATURE:
<223> OTHER INFORMATION: Synthetic

<400> SEQUENCE: 39

Met Ala Thr Val Lys Phe Thr Tyr Gln Gly Glu Glu Lys Gln Val Asp
1               5                   10                  15

Ile Ser Lys Ile Lys Trp Val Ile Arg Ser Gly Gln Arg Ile Asn Phe
            20                  25                  30

Ala Tyr Asp Glu Gly Gly Gly Ala Gly Gly Tyr Gly Gly Val Ser Glu
        35                  40                  45

Lys Asp Ala Pro Lys Glu Leu Leu Glu Lys Gln
    50                  55


<210> SEQ ID NO 40
<211> LENGTH: 59
<212> TYPE: PRT
<213> ORGANISM: Artificial Sequence
<220> FEATURE:
<223> OTHER INFORMATION: Synthetic

<400> SEQUENCE: 40

Met Ala Thr Val Lys Phe Thr Tyr Gln Gly Glu Glu Lys Gln Val Asp
1               5                   10                  15

Ile Ser Lys Ile Lys Tyr Val Ser Arg Gly Gly Gln Asp Ile Ser Phe
            20                  25                  30

Arg Tyr Asp Glu Gly Gly Gly Ala Ile Gly Ile Gly Tyr Val Ser Glu
        35                  40                  45

Lys Asp Ala Pro Lys Glu Leu Leu Glu Lys Gln
    50                  55


<210> SEQ ID NO 41
<211> LENGTH: 59
<212> TYPE: PRT
<213> ORGANISM: Artificial Sequence
<220> FEATURE:
<223> OTHER INFORMATION: Synthetic

<400> SEQUENCE: 41

Met Ala Thr Val Lys Phe Thr Tyr Gln Gly Glu Glu Lys Gln Val Asp
1               5                   10                  15

Ile Ser Lys Ile Lys His Val Asn Arg His Gly Gln Asn Ile Asp Phe
            20                  25                  30

Arg Tyr Asp Glu Gly Gly Gly Ala Asn Gly Arg Gly Ile Val Ser Glu
        35                  40                  45

Lys Asp Ala Pro Lys Glu Leu Leu Glu Lys Gln
    50                  55
```

<210> SEQ ID NO 42
<211> LENGTH: 59
<212> TYPE: PRT
<213> ORGANISM: Artificial Sequence
<220> FEATURE:
<223> OTHER INFORMATION: Synthetic

<400> SEQUENCE: 42

```
Met Ala Thr Val Lys Phe Thr Tyr Gln Gly Glu Glu Lys Gln Val Asp
1               5                   10                  15

Ile Ser Lys Ile Lys Gly Val Tyr Arg Ala Gly Gln His Ile Lys Phe
            20                  25                  30

Arg Tyr Asp Glu Gly Gly Gly Ala Gly Gly His Gly Gly Val Ser Glu
        35                  40                  45

Lys Asp Ala Pro Lys Glu Leu Leu Glu Lys Gln
    50                  55
```

<210> SEQ ID NO 43
<211> LENGTH: 59
<212> TYPE: PRT
<213> ORGANISM: Artificial Sequence
<220> FEATURE:
<223> OTHER INFORMATION: Synthetic

<400> SEQUENCE: 43

```
Met Ala Thr Val Lys Phe Thr Tyr Gln Gly Glu Glu Lys Gln Val Asp
1               5                   10                  15

Ile Ser Lys Ile Lys Ala Val Tyr Arg Asn Gly Gln Lys Ile Ile Phe
            20                  25                  30

Ile Tyr Asp Glu Gly Gly Gly Ala Tyr Gly His Gly His Val Ser Glu
        35                  40                  45

Lys Asp Ala Pro Lys Glu Leu Leu Glu Lys Gln
    50                  55
```

<210> SEQ ID NO 44
<211> LENGTH: 59
<212> TYPE: PRT
<213> ORGANISM: Artificial Sequence
<220> FEATURE:
<223> OTHER INFORMATION: Synthetic

<400> SEQUENCE: 44

```
Met Ala Thr Val Lys Phe Thr Tyr Gln Gly Glu Glu Lys Gln Val Asp
1               5                   10                  15

Ile Ser Lys Ile Lys His Val Tyr Arg Ala Gly Gln Tyr Ile Lys Phe
            20                  25                  30

Gly Tyr Asp Glu Gly Gly Gly Ala Ala Gly Gly Gly His Val Ser Glu
        35                  40                  45

Lys Asp Ala Pro Lys Glu Leu Leu Glu Lys Gln
    50                  55
```

<210> SEQ ID NO 45
<211> LENGTH: 59
<212> TYPE: PRT
<213> ORGANISM: Artificial Sequence
<220> FEATURE:
<223> OTHER INFORMATION: Synthetic

<400> SEQUENCE: 45

```
Met Ala Thr Val Lys Phe Thr Tyr Gln Gly Glu Glu Lys Gln Val Asp
1               5                   10                  15

Ile Ser Lys Ile Lys Asn Val Tyr Arg His Gly Gln Tyr Ile Lys Phe
```

```
            20                  25                  30

Arg Tyr Asp Glu Gly Gly Gly Ala Ser Gly Tyr Gly Ser Val Ser Glu
        35                  40                  45

Lys Asp Ala Pro Lys Glu Leu Leu Glu Lys Gln
    50                  55


<210> SEQ ID NO 46
<211> LENGTH: 59
<212> TYPE: PRT
<213> ORGANISM: Artificial Sequence
<220> FEATURE:
<223> OTHER INFORMATION: Synthetic

<400> SEQUENCE: 46

Met Ala Thr Val Lys Phe Thr Tyr Gln Gly Glu Glu Lys Gln Val Asp
1               5                   10                  15

Ile Ser Lys Ile Lys Tyr Val Ile Arg Trp Gly Gln His Ile Trp Phe
            20                  25                  30

Tyr Tyr Asp Glu Gly Gly Gly Ala Trp Gly Ser Gly Asn Val Ser Glu
        35                  40                  45

Lys Asp Ala Pro Lys Glu Leu Leu Glu Lys Gln
    50                  55


<210> SEQ ID NO 47
<211> LENGTH: 59
<212> TYPE: PRT
<213> ORGANISM: Artificial Sequence
<220> FEATURE:
<223> OTHER INFORMATION: Synthetic

<400> SEQUENCE: 47

Met Ala Thr Val Lys Phe Thr Tyr Gln Gly Glu Glu Lys Gln Val Asp
1               5                   10                  15

Ile Ser Lys Ile Lys Trp Val Ser Arg Trp Gly Gln Tyr Ile Tyr Phe
            20                  25                  30

Ser Tyr Asp Glu Gly Gly Gly Ala Ile Gly Gly Gly Gly Val Ser Glu
        35                  40                  45

Lys Asp Ala Pro Lys Glu Leu Leu Glu Lys Gln
    50                  55


<210> SEQ ID NO 48
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (33)..(33)
<223> OTHER INFORMATION: Xaa can be any naturally occurring amino acid

<400> SEQUENCE: 48

Met Ala Thr Val Lys Phe Thr Tyr Gln Gly Glu Glu Lys Gln Val Asp
1               5                   10                  15

Ile Ser Lys Ile Lys Ile Val His Arg Ala Gly Gln Trp Ile Gly Phe
            20                  25                  30

Xaa Tyr Asp Glu Gly Gly Gly Ala Trp Gly Ser Gly Ile Val Ser Glu
        35                  40                  45

Lys Asp Ala Pro Lys Glu Leu Leu Glu Lys Gln
    50                  55
```

<210> SEQ ID NO 49
<211> LENGTH: 59
<212> TYPE: PRT
<213> ORGANISM: Artificial Sequence
<220> FEATURE:
<223> OTHER INFORMATION: Synthetic

<400> SEQUENCE: 49

```
Met Ala Thr Val Lys Phe Thr Tyr Gln Gly Glu Glu Lys Gln Val Asp
1               5                   10                  15

Ile Ser Lys Ile Lys His Val Ser Arg Gly Gly Gln Trp Ile Asp Phe
            20                  25                  30

Ala Tyr Asp Glu Gly Gly Gly Ala His Gly Asp Gly Ala Val Ser Glu
        35                  40                  45

Lys Asp Ala Pro Lys Glu Leu Leu Glu Lys Gln
    50                  55
```

<210> SEQ ID NO 50
<211> LENGTH: 59
<212> TYPE: PRT
<213> ORGANISM: Artificial Sequence
<220> FEATURE:
<223> OTHER INFORMATION: Synthetic

<400> SEQUENCE: 50

```
Met Ala Thr Val Lys Phe Thr Tyr Gln Gly Glu Glu Lys Gln Val Asp
1               5                   10                  15

Ile Ser Lys Ile Lys Trp Val Ser Arg Trp Gly Gln Tyr Ile Tyr Phe
            20                  25                  30

Ser Tyr Asp Glu Gly Gly Gly Ala Ser Gly Gly Gly Ser Val Ser Glu
        35                  40                  45

Lys Asp Ala Pro Lys Glu Leu Leu Glu Lys Gln
    50                  55
```

<210> SEQ ID NO 51
<211> LENGTH: 59
<212> TYPE: PRT
<213> ORGANISM: Artificial Sequence
<220> FEATURE:
<223> OTHER INFORMATION: Synthetic

<400> SEQUENCE: 51

```
Met Ala Thr Val Lys Phe Thr Tyr Gln Gly Glu Glu Lys Gln Val Asp
1               5                   10                  15

Ile Ser Lys Ile Lys Trp Val Trp Arg Trp Gly Gln Trp Ile Lys Phe
            20                  25                  30

Tyr Tyr Asp Glu Gly Gly Gly Ala Ala Gly Trp Gly Ile Val Ser Glu
        35                  40                  45

Lys Asp Ala Pro Lys Glu Leu Leu Glu Lys Gln
    50                  55
```

<210> SEQ ID NO 52
<211> LENGTH: 59
<212> TYPE: PRT
<213> ORGANISM: Artificial Sequence
<220> FEATURE:
<223> OTHER INFORMATION: Synthetic

<400> SEQUENCE: 52

```
Met Ala Thr Val Lys Phe Thr Tyr Gln Gly Glu Glu Lys Gln Val Asp
1               5                   10                  15

Ile Ser Lys Ile Lys Tyr Val Lys Arg Trp Gly Gln Tyr Ile Trp Phe
```

```
            20                  25                  30

Ile Tyr Asp Glu Gly Gly Gly Ala Ala Gly Tyr Gly Asn Val Ser Glu
        35                  40                  45

Lys Asp Ala Pro Lys Glu Leu Leu Glu Lys Gln
    50                  55


<210> SEQ ID NO 53
<211> LENGTH: 59
<212> TYPE: PRT
<213> ORGANISM: Artificial Sequence
<220> FEATURE:
<223> OTHER INFORMATION: Synthetic

<400> SEQUENCE: 53

Met Ala Thr Val Lys Phe Thr Tyr Gln Gly Glu Glu Lys Gln Val Asp
1               5                   10                  15

Ile Ser Lys Ile Lys Trp Val Trp Arg Trp Gly Gln Tyr Ile Arg Phe
            20                  25                  30

Tyr Tyr Asp Glu Gly Gly Gly Ala Trp Gly Trp Gly Ile Val Ser Glu
        35                  40                  45

Lys Asp Ala Pro Lys Glu Leu Leu Glu Lys Gln
    50                  55


<210> SEQ ID NO 54
<211> LENGTH: 59
<212> TYPE: PRT
<213> ORGANISM: Artificial Sequence
<220> FEATURE:
<223> OTHER INFORMATION: Synthetic

<400> SEQUENCE: 54

Met Ala Thr Val Lys Phe Thr Tyr Gln Gly Glu Glu Lys Gln Val Asp
1               5                   10                  15

Ile Ser Lys Ile Lys Ile Val Trp Arg Trp Gly Gln Ala Ile Arg Phe
            20                  25                  30

Trp Tyr Asp Glu Gly Gly Gly Ala Gly Gly Arg Gly Tyr Val Ser Glu
        35                  40                  45

Lys Asp Ala Pro Lys Glu Leu Leu Glu Lys Gln
    50                  55


<210> SEQ ID NO 55
<211> LENGTH: 59
<212> TYPE: PRT
<213> ORGANISM: Artificial Sequence
<220> FEATURE:
<223> OTHER INFORMATION: Synthetic

<400> SEQUENCE: 55

Met Ala Thr Val Lys Phe Thr Tyr Gln Gly Glu Glu Lys Gln Val Asp
1               5                   10                  15

Ile Ser Lys Ile Lys Arg Val Trp Arg Trp Gly Gln Gly Ile Tyr Phe
            20                  25                  30

Trp Tyr Asp Glu Gly Gly Gly Ala Asp Gly Asn Gly Trp Val Ser Glu
        35                  40                  45

Lys Asp Ala Pro Lys Glu Leu Leu Glu Lys Gln
    50                  55


<210> SEQ ID NO 56
<211> LENGTH: 59
<212> TYPE: PRT
<213> ORGANISM: Artificial Sequence
```

<220> FEATURE:
<223> OTHER INFORMATION: Synthetic

<400> SEQUENCE: 56

Met Ala Thr Val Lys Phe Thr Tyr Gln Gly Glu Glu Lys Gln Val Asp
1               5                   10                  15

Ile Ser Lys Ile Lys Arg Val His Arg Tyr Gly Gln Trp Ile Trp Phe
            20                  25                  30

Arg Tyr Asp Glu Gly Gly Gly Ala Arg Gly His Gly His Val Ser Glu
        35                  40                  45

Lys Asp Ala Pro Lys Glu Leu Leu Glu Lys Gln
    50                  55

<210> SEQ ID NO 57
<211> LENGTH: 34
<212> TYPE: PRT
<213> ORGANISM: Artificial Sequence
<220> FEATURE:
<223> OTHER INFORMATION: Synthetic

<400> SEQUENCE: 57

Met Ala Thr Val Lys Phe Thr Tyr Gln Gly Glu Glu Lys Gln Val Asp
1               5                   10                  15

Ile Ser Lys Ile Lys His Val His Arg Trp Gly Gln Trp Ile Trp Phe
            20                  25                  30

Trp Leu

<210> SEQ ID NO 58
<211> LENGTH: 9
<212> TYPE: PRT
<213> ORGANISM: Artificial Sequence
<220> FEATURE:
<223> OTHER INFORMATION: Synthetic

<400> SEQUENCE: 58

Trp Lys Asp Ser Tyr Trp Ile Ala His
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic

<400> SEQUENCE: 59

Ser Ser Arg Gly Ala Ser Arg Tyr His
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic

<400> SEQUENCE: 60

Ile Ala Ala Trp Trp Trp His Arg Gly
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic

<400> SEQUENCE: 61

Gly Trp Trp Trp Trp Trp Ala Arg Tyr
1 5

<210> SEQ ID NO 62
<211> LENGTH: 9
<212> TYPE: PRT
<213> ORGANISM: Artificial Sequence
<220> FEATURE:
<223> OTHER INFORMATION: Synthetic

<400> SEQUENCE: 62

Trp Ile His Gly Tyr Ser Ile Gly Ser
1 5

<210> SEQ ID NO 63
<211> LENGTH: 9
<212> TYPE: PRT
<213> ORGANISM: Artificial Sequence
<220> FEATURE:
<223> OTHER INFORMATION: Synthetic

<400> SEQUENCE: 63

Trp His His Trp Gly Asp Ile Asp Ser
1 5

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Trp Ile Ser Arg Asn Ala Gly Tyr Gly
1 5

<210> SEQ ID NO 65
<211> LENGTH: 9
<212> TYPE: PRT
<213> ORGANISM: Artificial Sequence
<220> FEATURE:
<223> OTHER INFORMATION: Synthetic

<400> SEQUENCE: 65

Tyr Ser Gly Asp Ser Arg Ile Ile Tyr
1 5

<210> SEQ ID NO 66
<211> LENGTH: 9
<212> TYPE: PRT
<213> ORGANISM: Artificial Sequence
<220> FEATURE:
<223> OTHER INFORMATION: Synthetic

<400> SEQUENCE: 66

His Asn His Asn Asp Arg Asn Arg Ile
1 5

<210> SEQ ID NO 67
<211> LENGTH: 9
<212> TYPE: PRT
<213> ORGANISM: Artificial Sequence
<220> FEATURE:

<223> OTHER INFORMATION: Synthetic

<400> SEQUENCE: 67

Gly Tyr Ala His Lys Arg Gly His Gly
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic

<400> SEQUENCE: 68

Ala Tyr Asn Lys Ile Ile Tyr His His
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic

<400> SEQUENCE: 69

His Tyr Ala Tyr Lys Gly Ala Gly His
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic

<400> SEQUENCE: 70

Asn Tyr His Tyr Lys Arg Ser Tyr Ser
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic

<400> SEQUENCE: 71

Tyr Ile Trp His Trp Tyr Trp Ser Asn
1               5

<210> SEQ ID NO 72
<211> LENGTH: 59
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(22)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid
<220> FEATURE:

```
<221> NAME/KEY: misc_feature
<222> LOCATION: (29)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (45)..(45)
<223> OTHER INFORMATION: Xaa can be any naturally occurring amino acid

<400> SEQUENCE: 72

Met Ala Thr Val Lys Phe Thr Tyr Gln Gly Glu Glu Lys Gln Val Asp
1               5                   10                  15

Ile Ser Lys Ile Lys Xaa Val Xaa Arg Xaa Gly Gln Xaa Ile Xaa Phe
            20                  25                  30

Xaa Tyr Asp Glu Gly Gly Gly Ala Xaa Gly Xaa Gly Xaa Val Ser Glu
        35                  40                  45

Lys Asp Ala Pro Lys Glu Leu Leu Glu Lys Gln
    50                  55


<210> SEQ ID NO 73
<211> LENGTH: 9
<212> TYPE: PRT
<213> ORGANISM: Artificial Sequence
<220> FEATURE:
<223> OTHER INFORMATION: Synthetic

<400> SEQUENCE: 73

Trp Ser Trp Tyr Tyr Ser Ile Gly Gly
1               5


<210> SEQ ID NO 74
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 74

Ile His Ala Trp Gly Xaa Trp Ser Ile
1               5


<210> SEQ ID NO 75
<211> LENGTH: 9
<212> TYPE: PRT
<213> ORGANISM: Artificial Sequence
<220> FEATURE:
<223> OTHER INFORMATION: Synthetic

<400> SEQUENCE: 75

His Ser Gly Trp Asp Ala His Asp Ala
```

1 5

<210> SEQ ID NO 76
<211> LENGTH: 9
<212> TYPE: PRT
<213> ORGANISM: Artificial Sequence
<220> FEATURE:
<223> OTHER INFORMATION: Synthetic

<400> SEQUENCE: 76

Trp Ser Trp Tyr Tyr Ser Ser Gly Ser
1 5

<210> SEQ ID NO 77
<211> LENGTH: 9
<212> TYPE: PRT
<213> ORGANISM: Artificial Sequence
<220> FEATURE:
<223> OTHER INFORMATION: Synthetic

<400> SEQUENCE: 77

Trp Trp Trp Trp Lys Tyr Ala Trp Ile
1 5

<210> SEQ ID NO 78
<211> LENGTH: 9
<212> TYPE: PRT
<213> ORGANISM: Artificial Sequence
<220> FEATURE:
<223> OTHER INFORMATION: Synthetic

<400> SEQUENCE: 78

Tyr Lys Trp Tyr Trp Ile Ala Tyr Asn
1 5

<210> SEQ ID NO 79
<211> LENGTH: 9
<212> TYPE: PRT
<213> ORGANISM: Artificial Sequence
<220> FEATURE:
<223> OTHER INFORMATION: Synthetic

<400> SEQUENCE: 79

Trp Trp Trp Tyr Arg Tyr Trp Trp Ile
1 5

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Ile Trp Trp Ala Arg Trp Gly Arg Tyr
1 5

<210> SEQ ID NO 81
<211> LENGTH: 9
<212> TYPE: PRT
<213> ORGANISM: Artificial Sequence
<220> FEATURE:
<223> OTHER INFORMATION: Synthetic

<400> SEQUENCE: 81

Arg Trp Trp Gly Tyr Trp Asp Asn Trp
1 5

<210> SEQ ID NO 82
<211> LENGTH: 9
<212> TYPE: PRT
<213> ORGANISM: Artificial Sequence
<220> FEATURE:
<223> OTHER INFORMATION: Synthetic

<400> SEQUENCE: 82

```
Arg His Tyr Trp Trp Arg Arg His His
1               5
```

<210> SEQ ID NO 83
<211> LENGTH: 6
<212> TYPE: PRT
<213> ORGANISM: Artificial Sequence
<220> FEATURE:
<223> OTHER INFORMATION: Synthetic

<400> SEQUENCE: 83

```
His His Trp Trp Trp Trp
1               5
```

<210> SEQ ID NO 84
<211> LENGTH: 62
<212> TYPE: PRT
<213> ORGANISM: Synthetic; Nat.Omp_1

<400> SEQUENCE: 84

```
Met Ala Thr Val Lys Phe Thr Tyr Gln Gly Glu Glu Lys Gln Val Asp
1               5                   10                  15

Ile Ser Lys Ile Lys Trp Val Lys Arg Asp Gly Gln Ser Ile Tyr Phe
            20                  25                  30

Trp Tyr Asp Glu Gly Gly Gly Ala Ile Gly Ala Gly His Val Ser Glu
        35                  40                  45

Lys Asp Ala Pro Lys Glu Leu Leu Gln Met Leu Glu Lys Gln
    50                  55                  60
```

<210> SEQ ID NO 85
<211> LENGTH: 62
<212> TYPE: PRT
<213> ORGANISM: Synthetic; Nat.Omp_2

<400> SEQUENCE: 85

```
Met Ala Thr Val Lys Phe Thr Tyr Gln Gly Glu Glu Lys Gln Val Asp
1               5                   10                  15

Ile Ser Lys Ile Lys Ser Val Ser Arg Arg Gly Gln Gly Ile Ala Phe
            20                  25                  30

Ser Tyr Asp Glu Gly Gly Gly Ala Arg Gly Tyr Gly His Val Ser Glu
        35                  40                  45

Lys Asp Ala Pro Lys Glu Leu Leu Gln Met Leu Glu Lys Gln
    50                  55                  60
```

<210> SEQ ID NO 86
<211> LENGTH: 62
<212> TYPE: PRT
<213> ORGANISM: Synthetic; Nat.Omp_3

<400> SEQUENCE: 86

```
Met Ala Thr Val Lys Phe Thr Tyr Gln Gly Glu Glu Lys Gln Val Asp
1               5                   10                  15

Ile Ser Lys Ile Lys Ile Val Ala Arg Ala Gly Gln Trp Ile Trp Phe
```

```
            20                  25                  30

Trp Tyr Asp Glu Gly Gly Gly Ala His Gly Arg Gly Gly Val Ser Glu
        35                  40                  45

Lys Asp Ala Pro Lys Glu Leu Leu Gln Met Leu Glu Lys Gln
    50                  55                  60


<210> SEQ ID NO 87
<211> LENGTH: 62
<212> TYPE: PRT
<213> ORGANISM: Synthetic; Nat.Omp_4

<400> SEQUENCE: 87

Met Ala Thr Val Lys Phe Thr Tyr Gln Gly Glu Glu Lys Gln Val Asp
1               5                   10                  15

Ile Ser Lys Ile Lys Gly Val Trp Arg Trp Gly Gln Trp Ile Trp Phe
            20                  25                  30

Trp Tyr Asp Glu Gly Gly Gly Ala Ala Gly Arg Gly Tyr Val Ser Glu
        35                  40                  45

Lys Asp Ala Pro Lys Glu Leu Leu Gln Met Leu Glu Lys Gln
    50                  55                  60


<210> SEQ ID NO 88
<211> LENGTH: 62
<212> TYPE: PRT
<213> ORGANISM: Synthetic; Nat.Omp_5

<400> SEQUENCE: 88

Met Ala Thr Val Lys Phe Thr Tyr Gln Gly Glu Glu Lys Gln Val Asp
1               5                   10                  15

Ile Ser Lys Ile Lys Trp Val Ile Arg His Gly Gln Gly Ile Tyr Phe
            20                  25                  30

Ser Tyr Asp Glu Gly Gly Gly Ala Ile Gly Gly Gly Ser Val Ser Glu
        35                  40                  45

Lys Asp Ala Pro Lys Glu Leu Leu Gln Met Leu Glu Lys Gln
    50                  55                  60


<210> SEQ ID NO 89
<211> LENGTH: 62
<212> TYPE: PRT
<213> ORGANISM: Synthetic; Nat.Omp_6

<400> SEQUENCE: 89

Met Ala Thr Val Lys Phe Thr Tyr Gln Gly Glu Glu Lys Gln Val Asp
1               5                   10                  15

Ile Ser Lys Ile Lys Trp Val His Arg His Gly Gln Trp Ile Gly Phe
            20                  25                  30

Asp Tyr Asp Glu Gly Gly Gly Ala Ile Gly Asp Gly Ser Val Ser Glu
        35                  40                  45

Lys Asp Ala Pro Lys Glu Leu Leu Gln Met Leu Glu Lys Gln
    50                  55                  60


<210> SEQ ID NO 90
<211> LENGTH: 62
<212> TYPE: PRT
<213> ORGANISM: Synthetic; Nat.Omp_7

<400> SEQUENCE: 90

Met Ala Thr Val Lys Phe Thr Tyr Gln Gly Glu Glu Lys Gln Val Asp
1               5                   10                  15
```

Ile Ser Lys Ile Lys Trp Val Ile Arg Ser Gly Gln Arg Ile Asn Phe
20 25 30

Ala Tyr Asp Glu Gly Gly Gly Ala Gly Gly Tyr Gly Gly Val Ser Glu
35 40 45

Lys Asp Ala Pro Lys Glu Leu Leu Gln Met Leu Glu Lys Gln
50 55 60

<210> SEQ ID NO 91
<211> LENGTH: 62
<212> TYPE: PRT
<213> ORGANISM: Synthetic; Nat.Omp_8

<400> SEQUENCE: 91

Met Ala Thr Val Lys Phe Thr Tyr Gln Gly Glu Glu Lys Gln Val Asp
1 5 10 15

Ile Ser Lys Ile Lys Tyr Val Ser Arg Gly Gly Gln Asp Ile Ser Phe
20 25 30

Arg Tyr Asp Glu Gly Gly Gly Ala Ile Gly Ile Gly Tyr Val Ser Glu
35 40 45

Lys Asp Ala Pro Lys Glu Leu Leu Gln Met Leu Glu Lys Gln
50 55 60

<210> SEQ ID NO 92
<211> LENGTH: 62
<212> TYPE: PRT
<213> ORGANISM: Synthetic; Nat.Omp_9

<400> SEQUENCE: 92

Met Ala Thr Val Lys Phe Thr Tyr Gln Gly Glu Glu Lys Gln Val Asp
1 5 10 15

Ile Ser Lys Ile Lys His Val Asn Arg His Gly Gln Asn Ile Asp Phe
20 25 30

Arg Tyr Asp Glu Gly Gly Gly Ala Asn Gly Arg Gly Ile Val Ser Glu
35 40 45

Lys Asp Ala Pro Lys Glu Leu Leu Gln Met Leu Glu Lys Gln
50 55 60

<210> SEQ ID NO 93
<211> LENGTH: 62
<212> TYPE: PRT
<213> ORGANISM: Synthetic; Nat.Omp_10

<400> SEQUENCE: 93

Met Ala Thr Val Lys Phe Thr Tyr Gln Gly Glu Glu Lys Gln Val Asp
1 5 10 15

Ile Ser Lys Ile Lys Gly Val Tyr Arg Ala Gly Gln His Ile Lys Phe
20 25 30

Arg Tyr Asp Glu Gly Gly Gly Ala Gly Gly His Gly Gly Val Ser Glu
35 40 45

Lys Asp Ala Pro Lys Glu Leu Leu Gln Met Leu Glu Lys Gln
50 55 60

<210> SEQ ID NO 94
<211> LENGTH: 62
<212> TYPE: PRT
<213> ORGANISM: Synthetic; Nat.Omp_11

<400> SEQUENCE: 94

Met Ala Thr Val Lys Phe Thr Tyr Gln Gly Glu Glu Lys Gln Val Asp
1 5 10 15

```
Ile Ser Lys Ile Lys Ala Val Tyr Arg Asn Gly Gln Lys Ile Ile Phe
            20                  25                  30

Ile Tyr Asp Glu Gly Gly Gly Ala Tyr Gly His Gly His Val Ser Glu
        35                  40                  45

Lys Asp Ala Pro Lys Glu Leu Leu Gln Met Leu Glu Lys Gln
    50                  55                  60


<210> SEQ ID NO 95
<211> LENGTH: 62
<212> TYPE: PRT
<213> ORGANISM: Synthetic; Nat.Omp_12

<400> SEQUENCE: 95

Met Ala Thr Val Lys Phe Thr Tyr Gln Gly Glu Glu Lys Gln Val Asp
1               5                   10                  15

Ile Ser Lys Ile Lys His Val Tyr Arg Ala Gly Gln Tyr Ile Lys Phe
            20                  25                  30

Gly Tyr Asp Glu Gly Gly Gly Ala Ala Gly Gly Gly His Val Ser Glu
        35                  40                  45

Lys Asp Ala Pro Lys Glu Leu Leu Gln Met Leu Glu Lys Gln
    50                  55                  60


<210> SEQ ID NO 96
<211> LENGTH: 62
<212> TYPE: PRT
<213> ORGANISM: Synthetic; Nat.Omp_13

<400> SEQUENCE: 96

Met Ala Thr Val Lys Phe Thr Tyr Gln Gly Glu Glu Lys Gln Val Asp
1               5                   10                  15

Ile Ser Lys Ile Lys Asn Val Tyr Arg His Gly Gln Tyr Ile Lys Phe
            20                  25                  30

Arg Tyr Asp Glu Gly Gly Gly Ala Ser Gly Tyr Gly Ser Val Ser Glu
        35                  40                  45

Lys Asp Ala Pro Lys Glu Leu Leu Gln Met Leu Glu Lys Gln
    50                  55                  60


<210> SEQ ID NO 97
<211> LENGTH: 62
<212> TYPE: PRT
<213> ORGANISM: Synthetic; Nat.Omp_13

<400> SEQUENCE: 97

Met Ala Thr Val Lys Phe Thr Tyr Gln Gly Glu Glu Lys Gln Val Asp
1               5                   10                  15

Ile Ser Lys Ile Lys Tyr Val Ile Arg Trp Gly Gln His Ile Trp Phe
            20                  25                  30

Tyr Tyr Asp Glu Gly Gly Gly Ala Trp Gly Ser Gly Asn Val Ser Glu
        35                  40                  45

Lys Asp Ala Pro Lys Glu Leu Leu Gln Met Leu Glu Lys Gln
    50                  55                  60


<210> SEQ ID NO 98
<211> LENGTH: 62
<212> TYPE: PRT
<213> ORGANISM: Synthetic; OmpW.PF2-1

<400> SEQUENCE: 98

Met Ala Thr Val Lys Phe Thr Tyr Gln Gly Glu Glu Lys Gln Val Asp
```

```
1               5                   10                  15

Ile Ser Lys Ile Lys Trp Val Ser Arg Trp Gly Gln Tyr Ile Tyr Phe
            20                  25                  30

Ser Tyr Asp Glu Gly Gly Gly Ala Ile Gly Gly Gly Gly Val Ser Glu
        35                  40                  45

Lys Asp Ala Pro Lys Glu Leu Leu Gln Met Leu Glu Lys Gln
    50                  55                  60


<210> SEQ ID NO 99
<211> LENGTH: 62
<212> TYPE: PRT
<213> ORGANISM: Synthetic; OmpW.PF2-2
<220> FEATURE:
<221> NAME/KEY: misc_feature
<222> LOCATION: (33)..(33)
<223> OTHER INFORMATION: Xaa can be any naturally occurring amino acid

<400> SEQUENCE: 99

Met Ala Thr Val Lys Phe Thr Tyr Gln Gly Glu Glu Lys Gln Val Asp
1               5                   10                  15

Ile Ser Lys Ile Lys Ile Val His Arg Ala Gly Gln Trp Ile Gly Phe
            20                  25                  30

Xaa Tyr Asp Glu Gly Gly Gly Ala Trp Gly Ser Gly Ile Val Ser Glu
        35                  40                  45

Lys Asp Ala Pro Lys Glu Leu Leu Gln Met Leu Glu Lys Gln
    50                  55                  60


<210> SEQ ID NO 100
<211> LENGTH: 62
<212> TYPE: PRT
<213> ORGANISM: Synthetic; OmpW.PF2-4

<400> SEQUENCE: 100

Met Ala Thr Val Lys Phe Thr Tyr Gln Gly Glu Glu Lys Gln Val Asp
1               5                   10                  15

Ile Ser Lys Ile Lys His Val Ser Arg Gly Gly Gln Trp Ile Asp Phe
            20                  25                  30

Ala Tyr Asp Glu Gly Gly Gly Ala His Gly Asp Gly Ala Val Ser Glu
        35                  40                  45

Lys Asp Ala Pro Lys Glu Leu Leu Gln Met Leu Glu Lys Gln
    50                  55                  60


<210> SEQ ID NO 101
<211> LENGTH: 62
<212> TYPE: PRT
<213> ORGANISM: Synthetic; OmpW.PF2-6

<400> SEQUENCE: 101

Met Ala Thr Val Lys Phe Thr Tyr Gln Gly Glu Glu Lys Gln Val Asp
1               5                   10                  15

Ile Ser Lys Ile Lys Trp Val Ser Arg Trp Gly Gln Tyr Ile Tyr Phe
            20                  25                  30

Ser Tyr Asp Glu Gly Gly Gly Ala Ser Gly Gly Gly Ser Val Ser Glu
        35                  40                  45

Lys Asp Ala Pro Lys Glu Leu Leu Gln Met Leu Glu Lys Gln
    50                  55                  60


<210> SEQ ID NO 102
<211> LENGTH: 62
<212> TYPE: PRT
```

<213> ORGANISM: Synthetic; OmpW.PF3-1

<400> SEQUENCE: 102

```
Met Ala Thr Val Lys Phe Thr Tyr Gln Gly Glu Glu Lys Gln Val Asp
1               5                   10                  15

Ile Ser Lys Ile Lys Trp Val Trp Arg Trp Gly Gln Trp Ile Lys Phe
            20                  25                  30

Tyr Tyr Asp Glu Gly Gly Gly Ala Ala Gly Trp Gly Ile Val Ser Glu
        35                  40                  45

Lys Asp Ala Pro Lys Glu Leu Leu Gln Met Leu Glu Lys Gln
    50                  55                  60
```

<210> SEQ ID NO 103
<211> LENGTH: 62
<212> TYPE: PRT
<213> ORGANISM: Synthetic; OmpW.PF3-2

<400> SEQUENCE: 103

```
Met Ala Thr Val Lys Phe Thr Tyr Gln Gly Glu Glu Lys Gln Val Asp
1               5                   10                  15

Ile Ser Lys Ile Lys Tyr Val Lys Arg Trp Gly Gln Tyr Ile Trp Phe
            20                  25                  30

Ile Tyr Asp Glu Gly Gly Gly Ala Ala Gly Tyr Gly Asn Val Ser Glu
        35                  40                  45

Lys Asp Ala Pro Lys Glu Leu Leu Gln Met Leu Glu Lys Gln
    50                  55                  60
```

<210> SEQ ID NO 104
<211> LENGTH: 62
<212> TYPE: PRT
<213> ORGANISM: Synthetic; OmpW.PF3-3

<400> SEQUENCE: 104

```
Met Ala Thr Val Lys Phe Thr Tyr Gln Gly Glu Glu Lys Gln Val Asp
1               5                   10                  15

Ile Ser Lys Ile Lys Trp Val Trp Arg Trp Gly Gln Tyr Ile Arg Phe
            20                  25                  30

Tyr Tyr Asp Glu Gly Gly Gly Ala Trp Gly Trp Gly Ile Val Ser Glu
        35                  40                  45

Lys Asp Ala Pro Lys Glu Leu Leu Gln Met Leu Glu Lys Gln
    50                  55                  60
```

<210> SEQ ID NO 105
<211> LENGTH: 62
<212> TYPE: PRT
<213> ORGANISM: Synthetic; OmpW.PF3-7

<400> SEQUENCE: 105

```
Met Ala Thr Val Lys Phe Thr Tyr Gln Gly Glu Glu Lys Gln Val Asp
1               5                   10                  15

Ile Ser Lys Ile Lys Ile Val Trp Arg Trp Gly Gln Ala Ile Arg Phe
            20                  25                  30

Trp Tyr Asp Glu Gly Gly Gly Ala Gly Gly Arg Gly Tyr Val Ser Glu
        35                  40                  45

Lys Asp Ala Pro Lys Glu Leu Leu Gln Met Leu Glu Lys Gln
    50                  55                  60
```

<210> SEQ ID NO 106
<211> LENGTH: 62

```
<212> TYPE: PRT
<213> ORGANISM: Synthetic; OmpA.PF2-2

<400> SEQUENCE: 106

Met Ala Thr Val Lys Phe Thr Tyr Gln Gly Glu Glu Lys Gln Val Asp
1               5                   10                  15

Ile Ser Lys Ile Lys Arg Val Trp Arg Trp Gly Gln Gly Ile Tyr Phe
            20                  25                  30

Trp Tyr Asp Glu Gly Gly Gly Ala Asp Gly Asn Gly Trp Val Ser Glu
        35                  40                  45

Lys Asp Ala Pro Lys Glu Leu Leu Gln Met Leu Glu Lys Gln
    50                  55                  60


<210> SEQ ID NO 107
<211> LENGTH: 62
<212> TYPE: PRT
<213> ORGANISM: Synthetic; OmpA.PF2-3

<400> SEQUENCE: 107

Met Ala Thr Val Lys Phe Thr Tyr Gln Gly Glu Glu Lys Gln Val Asp
1               5                   10                  15

Ile Ser Lys Ile Lys Arg Val His Arg Tyr Gly Gln Trp Ile Trp Phe
            20                  25                  30

Arg Tyr Asp Glu Gly Gly Gly Ala Arg Gly His Gly His Val Ser Glu
        35                  40                  45

Lys Asp Ala Pro Lys Glu Leu Leu Gln Met Leu Glu Lys Gln
    50                  55                  60


<210> SEQ ID NO 108
<211> LENGTH: 34
<212> TYPE: PRT
<213> ORGANISM: Artificial Sequence
<220> FEATURE:
<223> OTHER INFORMATION: Synthetic; OmpA.PF2-1

<400> SEQUENCE: 108

Met Ala Thr Val Lys Phe Thr Tyr Gln Gly Glu Glu Lys Gln Val Asp
1               5                   10                  15

Ile Ser Lys Ile Lys His Val His Arg Trp Gly Gln Trp Ile Trp Phe
            20                  25                  30

Trp Leu
```